US012662550B2

(12) United States Patent
Meyvis et al.

(10) Patent No.: US 12,662,550 B2
(45) Date of Patent: Jun. 23, 2026

(54) STABLE FORMULATIONS OF IMMUNOGLOBULIN SINGLE VARIABLE DOMAINS

(71) Applicant: Ablynx N.V., Ghent-Zwijnaarde (BE)

(72) Inventors: Yves Meyvis, Ghent (BE); Veronique De Brabandere, Ghent (BE); Hans Ulrichts, Kortrijk (BE); Ann Brige, Ertvelde (BE); Filip Callewaert, Zulte (BE)

(73) Assignee: Ablynx NV, Zwijnaarde (BE)

( * ) Notice: Subject to any disclaimer, the term of this patent is extended or adjusted under 35 U.S.C. 154(b) by 796 days.

(21) Appl. No.: 16/008,103

(22) Filed: Jun. 14, 2018

(65) Prior Publication Data

US 2019/0010249 A1 Jan. 10, 2019

Related U.S. Application Data

(63) Continuation of application No. 14/891,441, filed as application No. PCT/EP2014/060107 on May 16, 2014, now Pat. No. 10,035,862.

(60) Provisional application No. 61/824,523, filed on May 17, 2013.

(51) Int. Cl.

| | |
|---|---|
| *C07K 16/36* | (2006.01) |
| *A61K 9/00* | (2006.01) |
| *A61K 9/08* | (2006.01) |
| *A61K 9/19* | (2006.01) |
| *A61K 39/395* | (2006.01) |

(52) U.S. Cl.
CPC ............ *C07K 16/36* (2013.01); *A61K 9/0019* (2013.01); *A61K 9/08* (2013.01); *A61K 9/19* (2013.01); *A61K 39/39591* (2013.01); *C07K 2317/22* (2013.01); *C07K 2317/569* (2013.01); *C07K 2317/94* (2013.01)

(58) Field of Classification Search
CPC .......... A61K 39/3955; A61K 39/39591; A61K 9/0019; A61K 9/08; A61K 2039/505; A61P 7/02; A61P 7/04; A61P 9/10; C07K 16/36; C07K 2317/22; C07K 2317/94; C07K 2317/569
See application file for complete search history.

(56) References Cited

U.S. PATENT DOCUMENTS

| | | | |
|---|---|---|---|
| 2009/0214535 A1 | 8/2009 | Igawa | |
| 2009/0226530 A1* | 9/2009 | Lassner ................... | A61P 25/04 |
| | | | 424/490 |
| 2010/0137213 A1 | 6/2010 | Fernandez | |
| 2010/0260766 A1 | 10/2010 | Srivastava et al. | |
| 2011/0158996 A1 | 6/2011 | Holz et al. | |
| 2012/0225072 A1 | 9/2012 | Meyvis et al. | |

FOREIGN PATENT DOCUMENTS

| | | | |
|---|---|---|---|
| EP | 2196476 A1 | 6/2010 | |
| JP | 2016-513387 A | 5/2016 | |
| RU | 2006100306 A | 6/2006 | |
| RU | 2295329 C2 | 3/2007 | |
| WO | WO 2009/115614 A2 | 9/2009 | |
| WO | WO 2010/077422 A2 | 7/2010 | |
| WO | WO 2014/118665 A1 | 8/2014 | |

OTHER PUBLICATIONS

Redetzki et al ( Proc Soc Exp Biol Med. Jan. 1972;139(1):315-8) (Year: 1972).*

Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25.) (Year: 2002).*

Callewaert et al., Evaluation of efficacy and safety of the anti-VWF Nanobody ALX-0681 in a preclinical baboon model of acquired thrombotic thrombocytopeniaurpura. Blood. Oct. 25, 2012;120(17):3603-10. doi:10.1182/blood-2012-04-420943. Epub Sep. 4, 2012.

Carpenter et al., Potential inaccurate quantitation and sizing of protein aggregates by size exclusion chromatography: essential need to use orthogonal methods to assure the quality of therapeutic protein products. J Pharm Sci. May 2010;99(5):2200-8. doi:10.1002/jps.21989.

Daugherty et al., Formulation and delivery issues for monoclonal antibody therapeutics. Adv Drug Deliv Rev. Aug. 7, 2006;58(5-6):686-706. Epub May 22, 2006.

Decherchi et al., Implicit solvent methods for free energy estimation. Eur J Med Chem. Feb. 16, 2015;91:27-42. doi:10.1016/j.ejmech.2014.08.064. Epub Aug. 25, 2014.

Gil et al., Strategies to stabilize compact folding and minimize aggregation of antibody-based fragments. Adv Biosci Biotechnol. Apr. 2013;4(4a):73-84.

Gokarn et al., Excipients for Protein Drugs. CRC Press. 2006;291-331.

Harmsen et al., Llama heavy-chain V regions consist of at least four distinct subfamilies revealing novel sequence features. Mol Immunol. Aug. 2000;37(10):579-90.

(Continued)

*Primary Examiner* — Brian Gangle
*Assistant Examiner* — Andrea K McCollum
(74) *Attorney, Agent, or Firm* — Wolf, Greenfield & Sacks, P.C.

(57) ABSTRACT

The present invention relates to stable formulations of polypeptides, e.g. immunoglobulin single variable domains, in particular immunoglobulin single variable domains directed against von Willebrand Factor (vWF).

The invention provides formulations which are stable upon storage for prolonged periods of time and over a broad range of temperatures. The formulations of the invention ensure a high stability of the polypeptide, allowing multiple freeze-thaw cycles without chemical or physical deterioration, and provide stability in relation to mechanical stress, such as shake, shear or stir stress. They are suitable for pharmaceutical and diagnostic preparations and compatible with pharmaceutically acceptable diluents.

19 Claims, 13 Drawing Sheets

Specification includes a Sequence Listing.

(56)  References Cited

OTHER PUBLICATIONS

Hawe et al., Forced degradation of therapeutic proteins. J Pharm Sci. Mar. 2012;101(3):895-913. doi:10.1002/jps.22812. Epub Nov. 14, 2011.

Nieba et al., Disrupting the hydrophobic patches at the antibody variable/constant domain interface: improved in vivo folding and physical characterization of an engineered scFv fragment. Protein Eng. Apr. 1997;10(4):435-44.

Ulrichts et al., Antithrombotic drug candidate ALX-0081 shows superior preclinical efficacy and safety compared with currently marketed antiplatelet drugs. Blood. Jul. 21, 2011;118(3):757-65. doi: 10.1182/blood-2010-11-317859. Epub May 16, 2011.

Yamagishi et al., A new set of atomic radii for accurate estimation of solvation free energy by Poisson-Boltzmann solvent model. J Comput Chem. Nov. 5, 2014;35(29):2132-9. doi: 10.1002/jcc. 23728. Epub Sep. 15, 2014.

Zhou et al., Variational implicit solvation with Poisson-Boltzmann theory. J Chem Theory Comput. Apr. 8, 2014;10(4):1454-1467. Epub Feb. 21, 2014.

* cited by examiner

SEQUENCE LISTING

<160> NUMBER OF SEQ ID NOS: 20

<210> SEQ ID NO 1
<211> LENGTH: 259
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
        195                 200                 205

```
Met Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 2
<211> LENGTH: 259
<212> TYPE: PRT
<213> ORGANISM: Artificial Sequence
<220> FEATURE:
<223> OTHER INFORMATION: Nanobody sequence

<400> SEQUENCE: 2

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
    130                 135                 140

Ala Gly Gly Ala Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Glu Arg
                165                 170                 175

Asp Leu Val Ala Ala Ile Ser Arg Thr Gly Gly Ser Thr Tyr Tyr Pro
                180                 185                 190

Asp Ser Val Glu Gly Arg Phe Thr Ile Ser Arg Asp Asn Ala Lys Arg
            195                 200                 205

Met Val Tyr Leu Gln Met Asn Asn Leu Lys Pro Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 3
<211> LENGTH: 265
<212> TYPE: PRT
<213> ORGANISM: Artificial Sequence
<220> FEATURE:
<223> OTHER INFORMATION: Nanobody sequence
```

```
<400> SEQUENCE: 3

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
                20                  25                  30

Pro Met Gly Trp Phe Arg Gln Ala Pro Gly Lys Glu Arg Asp Leu Val
            35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Gly Gly Gly Gly Ser Gly Gly Gly Ser Glu Val Gln Leu Val Glu Ser
    130                 135                 140

Gly Gly Gly Leu Val Gln Ala Gly Gly Ala Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Glu Arg Asp Leu Val Ala Ala Ile Ser Arg Thr Gly
            180                 185                 190

Gly Ser Thr Tyr Tyr Pro Asp Ser Val Glu Gly Arg Phe Thr Ile Ser
            195                 200                 205

Arg Asp Asn Ala Lys Arg Met Val Tyr Leu Gln Met Asn Asn Leu Lys
    210                 215                 220

Pro Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Thr Phe Trp Gly
            245                 250                 255

Gln Gly Thr Gln Val Thr Val Ser Ser
            260                 265

<210> SEQ ID NO 4
<211> LENGTH: 286
<212> TYPE: PRT
<213> ORGANISM: Artificial Sequence
<220> FEATURE:
<223> OTHER INFORMATION: Nanobody sequence

<400> SEQUENCE: 4

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
                20                  25                  30

Pro Met Gly Trp Phe Arg Gln Ala Pro Gly Lys Glu Arg Asp Leu Val
            35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
```

-continued

```
            85                90                95

Ala Ala Ala Gly Val Arg Ala Glu Asp Gly Arg Val Arg Thr Leu Pro
            100               105               110

Ser Glu Tyr Thr Phe Trp Gly Gln Gly Thr Gln Val Thr Val Ser Ser
            115               120               125

Gly Gly Gly Gly Ser Gly Gly Gly Ser Gly Gly Gly Gly Ser Gly
            130               135               140

Gly Gly Gly Ser Gly Gly Gly Gly Ser Gly Gly Gly Ser Glu Val
145                   150               155               160

Gln Leu Val Glu Ser Gly Gly Gly Leu Val Gln Ala Gly Gly Ala Leu
                165               170               175

Arg Leu Ser Cys Ala Ala Ser Gly Arg Thr Phe Ser Tyr Asn Pro Met
                180               185               190

Gly Trp Phe Arg Gln Ala Pro Gly Lys Glu Arg Asp Leu Val Ala Ala
                195               200               205

Ile Ser Arg Thr Gly Gly Ser Thr Tyr Tyr Pro Asp Ser Val Glu Gly
            210               215               220

Arg Phe Thr Ile Ser Arg Asp Asn Ala Lys Arg Met Val Tyr Leu Gln
225                   230               235               240

Met Asn Asn Leu Lys Pro Glu Gly Thr Ala Val Tyr Tyr Cys Ala Ala
                245               250               255

Ala Gly Val Arg Ala Glu Asp Gly Arg Val Arg Thr Leu Pro Ser Glu
                260               265               270

Tyr Thr Phe Trp Gly Gln Gly Thr Gln Val Thr Val Ser Ser
            275               280               285
```

```
<210> SEQ ID NO 5
<211> LENGTH: 247
<212> TYPE: PRT
<213> ORGANISM: Artificial Sequence
<220> FEATURE:
<223> OTHER INFORMATION: Nanobody sequence

<400> SEQUENCE: 5

Ala Val Gln Leu Val Glu Ser Gly Gly Gly Leu Val Gln Pro Gly Gly
1               5                10                15

Ser Leu Arg Leu Ser Cys Leu Ala Ser Gly Arg Ile Phe Ser Ile Gly
            20                25                30

Ala Met Gly Met Tyr Arg Gln Ala Pro Gly Lys Gln Arg Glu Leu Val
            35                40                45

Ala Thr Ile Thr Ser Gly Gly Ser Thr Asn Tyr Ala Asp Pro Val Lys
            50                55                60

Gly Arg Phe Thr Ile Ser Arg Asp Gly Pro Lys Asn Thr Val Tyr Leu
65                   70                75                80

Gln Met Asn Ser Leu Lys Pro Glu Asp Thr Ala Val Tyr Tyr Cys Tyr
                85                90                95

Ala Asn Leu Lys Gln Gly Ser Tyr Gly Tyr Arg Phe Asn Asp Tyr Trp
            100               105               110

Gly Gln Gly Thr Gln Val Thr Val Ser Ser Ala Ala Ala Glu Val Gln
            115               120               125

Leu Val Glu Ser Gly Gly Gly Leu Val Gln Pro Gly Gly Ser Leu Arg
            130               135               140

Leu Ser Cys Leu Ala Ser Gly Arg Ile Phe Ser Ile Gly Ala Met Gly
145               150               155               160

Met Tyr Arg Gln Ala Pro Gly Lys Gln Arg Glu Leu Val Ala Thr Ile
```

-continued

```
                  165                 170                 175
Thr Ser Gly Gly Ser Thr Asn Tyr Ala Asp Pro Val Lys Gly Arg Phe
            180                 185                 190

Thr Ile Ser Arg Asp Gly Pro Lys Asn Thr Val Tyr Leu Gln Met Asn
        195                 200                 205

Ser Leu Lys Pro Glu Asp Thr Ala Val Tyr Tyr Cys Tyr Ala Asn Leu
    210                 215                 220

Lys Gln Gly Ser Tyr Gly Tyr Arg Phe Asn Asp Tyr Trp Gly Gln Gly
225                 230                 235                 240

Thr Gln Val Thr Val Ser Ser
            245
```

```
<210> SEQ ID NO 6
<211> LENGTH: 253
<212> TYPE: PRT
<213> ORGANISM: Artificial Sequence
<220> FEATURE:
<223> OTHER INFORMATION: Nanobody sequence

<400> SEQUENCE: 6

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Met Tyr Arg Gln Ala Pro Gly Lys Gln Arg Glu Leu Val
        35                  40                  45

Ala Thr Ile Thr Ser Gly Gly Ser Thr Asn Tyr Ala Asp Pro Val Lys
    50                  55                  60

Gly Arg Phe Thr Ile Ser Arg Asp Gly Pro Lys Asn Thr Val Tyr Leu
65                  70                  75                  80

Gln Met Asn Ser Leu Lys Pro Glu Asp Thr Ala Val Tyr Tyr Cys Tyr
            85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Leu Ala Ser Gly Arg Ile Phe
145                 150                 155                 160

Ser Ile Gly Ala Met Gly Met Tyr Arg Gln Ala Pro Gly Lys Gln Arg
            165                 170                 175

Glu Leu Val Ala Thr Ile Thr Ser Gly Gly Ser Thr Asn Tyr Ala Asp
        180                 185                 190

Pro Val Lys Gly Arg Phe Thr Ile Ser Arg Asp Gly Pro Lys Asn Thr
        195                 200                 205

Val Tyr Leu Gln Met Asn Ser Leu Lys Pro Glu Asp Thr Ala Val Tyr
    210                 215                 220

Tyr Cys Tyr Ala Asn Leu Lys Gln Gly Ser Tyr Gly Tyr Arg Phe Asn
225                 230                 235                 240

Asp Tyr Trp Gly Gln Gly Thr Gln Val Thr Val Ser Ser
            245                 250
```

```
<210> SEQ ID NO 7
<211> LENGTH: 274
<212> TYPE: PRT
```

<213> ORGANISM: Artificial Sequence
<220> FEATURE:
<223> OTHER INFORMATION: Nanobody sequence

<400> SEQUENCE: 7

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Met Tyr Arg Gln Ala Pro Gly Lys Gln Arg Glu Leu Val
            35                  40                  45

Ala Thr Ile Thr Ser Gly Gly Ser Thr Asn Tyr Ala Asp Pro Val Lys
        50                  55                  60

Gly Arg Phe Thr Ile Ser Arg Asp Gly Pro Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
                100                 105                 110

Gly Gln Gly Thr Gln Val Thr Val Ser Ser Gly Gly Gly Gly Ser Gly
            115                 120                 125

Gly Gly Gly Ser Gly Gly Gly Ser Gly Gly Gly Gly Ser Gly Gly
        130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Leu Ala
                165                 170                 175

Ser Gly Arg Ile Phe Ser Ile Gly Ala Met Gly Met Tyr Arg Gln Ala
                180                 185                 190

Pro Gly Lys Gln Arg Glu Leu Val Ala Thr Ile Thr Ser Gly Gly Ser
                195                 200                 205

Thr Asn Tyr Ala Asp Pro Val Lys Gly Arg Phe Thr Ile Ser Arg Asp
            210                 215                 220

Gly Pro Lys Asn Thr Val Tyr Leu Gln Met Asn Ser Leu Lys Pro Glu
225                 230                 235                 240

Asp Thr Ala Val Tyr Tyr Cys Tyr Ala Asn Leu Lys Gln Gly Ser Tyr
                245                 250                 255

Gly Tyr Arg Phe Asn Asp Tyr Trp Gly Gln Gly Thr Gln Val Thr Val
                260                 265                 270

Ser Ser

<210> SEQ ID NO 8
<211> LENGTH: 259
<212> TYPE: PRT
<213> ORGANISM: Artificial Sequence
<220> FEATURE:
<223> OTHER INFORMATION: Nanobody sequence

<400> SEQUENCE: 8

Gln Val Gln Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Val Val
            35                  40                  45

Ala Ala Ile Ser Arg Thr Gly Gly Ser Thr Tyr Tyr Ala Arg Ser Val

-continued

```
          50              55              60

Glu Gly Arg Phe Thr Ile Ser Arg Asp Asn Ala Lys Arg Met Val Tyr
65              70              75              80

Leu Gln Met Asn Ala Leu Lys Pro Glu Asp Thr Ala Val Tyr Tyr Cys
            85              90              95

Ala Ala Ala Gly Val Arg Ala Glu Asp Gly Arg Val Arg Thr Leu Pro
            100             105             110

Ser Glu Tyr Asn Phe Trp Gly Gln Gly Thr Gln Val Thr Val Ser Ser
            115             120             125

Ala Ala Ala Glu Val Gln Leu Val Glu Ser Gly Gly Gly Leu Val Gln
            130             135             140

Ala Gly Gly Ala Leu Arg Leu Ser Cys Ala Ala Ser Gly Arg Thr Phe
145             150             155             160

Ser Tyr Asn Pro Met Gly Trp Phe Arg Gln Ala Pro Gly Lys Glu Arg
                165             170             175

Asp Val Val Ala Ala Ile Ser Arg Thr Gly Gly Ser Thr Tyr Tyr Ala
            180             185             190

Arg Ser Val Glu Gly Arg Phe Thr Ile Ser Arg Asp Asn Ala Lys Arg
            195             200             205

Met Val Tyr Leu Gln Met Asn Ala Leu Lys Pro Glu Asp Thr Ala Val
            210             215             220

Tyr Tyr Cys Ala Ala Ala Gly Val Arg Ala Glu Asp Gly Arg Val Arg
225             230             235             240

Thr Leu Pro Ser Glu Tyr Asn Phe Trp Gly Gln Gly Thr Gln Val Thr
                245             250             255

Val Ser Ser
```

<210> SEQ ID NO 9
<211> LENGTH: 265
<212> TYPE: PRT
<213> ORGANISM: Artificial Sequence
<220> FEATURE:
<223> OTHER INFORMATION: Nanobody sequence

<400> SEQUENCE: 9

```
Gln Val Gln Leu Val Glu Ser Gly Gly Gly Leu Val Gln Ala Gly Gly
1               5               10              15

Ala Leu Arg Leu Ser Cys Ala Ala Ser Gly Arg Thr Phe Ser Tyr Asn
            20              25              30

Pro Met Gly Trp Phe Arg Gln Ala Pro Gly Lys Glu Arg Asp Val Val
            35              40              45

Ala Ala Ile Ser Arg Thr Gly Gly Ser Thr Tyr Tyr Ala Arg Ser Val
            50              55              60

Glu Gly Arg Phe Thr Ile Ser Arg Asp Asn Ala Lys Arg Met Val Tyr
65              70              75              80

Leu Gln Met Asn Ala Leu Lys Pro Glu Asp Thr Ala Val Tyr Tyr Cys
            85              90              95

Ala Ala Ala Gly Val Arg Ala Glu Asp Gly Arg Val Arg Thr Leu Pro
            100             105             110

Ser Glu Tyr Asn Phe Trp Gly Gln Gly Thr Gln Val Thr Val Ser Ser
            115             120             125

Gly Gly Gly Gly Ser Gly Gly Gly Ser Glu Val Gln Leu Val Glu Ser
            130             135             140

Gly Gly Gly Leu Val Gln Ala Gly Gly Ala Leu Arg Leu Ser Cys Ala
145             150             155             160
```

Ala Ser Gly Arg Thr Phe Ser Tyr Asn Pro Met Gly Trp Phe Arg Gln
            165                 170                 175

Ala Pro Gly Lys Glu Arg Asp Val Val Ala Ala Ile Ser Arg Thr Gly
            180                 185                 190

Gly Ser Thr Tyr Tyr Ala Arg Ser Val Glu Gly Arg Phe Thr Ile Ser
            195                 200                 205

Arg Asp Asn Ala Lys Arg Met Val Tyr Leu Gln Met Asn Ala Leu Lys
            210                 215                 220

Pro Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Asn Phe Trp Gly
            245                 250                 255

Gln Gly Thr Gln Val Thr Val Ser Ser
            260                 265

<210> SEQ ID NO 10
<211> LENGTH: 286
<212> TYPE: PRT
<213> ORGANISM: Artificial Sequence
<220> FEATURE:
<223> OTHER INFORMATION: Nanobody sequence

<400> SEQUENCE: 10

Gln Val Gln Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Val Val
            35                  40                  45

Ala Ala Ile Ser Arg Thr Gly Gly Ser Thr Tyr Tyr Ala Arg Ser Val
            50                  55                  60

Glu Gly Arg Phe Thr Ile Ser Arg Asp Asn Ala Lys Arg Met Val Tyr
65                  70                  75                  80

Leu Gln Met Asn Ala Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
            115                 120                 125

Gly Gly Gly Gly Ser Gly Gly Gly Gly Ser Gly Gly Gly Gly Ser Gly
            130                 135                 140

Gly Gly Gly Ser Gly Gly Gly Gly Ser Gly Gly Gly Gly Ser Glu Val
145                 150                 155                 160

Gln Leu Val Glu Ser Gly Gly Gly Leu Val Gln Ala Gly Gly Ala Leu
            165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Glu Arg Asp Val Val Ala Ala
            195                 200                 205

Ile Ser Arg Thr Gly Gly Ser Thr Tyr Tyr Ala Arg Ser Val Glu Gly
            210                 215                 220

Arg Phe Thr Ile Ser Arg Asp Asn Ala Lys Arg Met Val Tyr Leu Gln
225                 230                 235                 240

Met Asn Ala Leu Lys Pro Glu Asp Thr Ala Val Tyr Tyr Cys Ala Ala
            245                 250                 255

-continued

```
Ala Gly Val Arg Ala Glu Asp Gly Arg Val Arg Thr Leu Pro Ser Glu
            260                 265                 270

Tyr Asn Phe Trp Gly Gln Gly Thr Gln Val Thr Val Ser Ser
            275                 280                 285

<210> SEQ ID NO 11
<211> LENGTH: 259
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
            35                  40                  45

Ala Ala Ile Ser Arg Thr Gly Gly Ser Thr Tyr Tyr Pro Asp Ser Val
            50                  55                  60

Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
            130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
                180                 185                 190

Asp Ser Val Glu Gly Arg Phe Thr Ile Ser Arg Asp Asn Ala Lys Arg
                195                 200                 205

Ser Val Tyr Leu Gln Met Asn Ser Leu Arg Ala Glu Asp Thr Ala Val
            210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 12
<211> LENGTH: 259
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Arg Thr Phe Ser Tyr Asn
        20              25              30

Pro Met Gly Trp Phe Arg Gln Ala Pro Gly Lys Gly Arg Glu Val Val
        35              40              45

Ala Ala Ile Ser Arg Thr Gly Gly Ser Thr Tyr Tyr Ala Arg Ser Val
    50              55              60

Glu Gly Arg Phe Thr Ile Ser Arg Asp Asn Ala Lys Arg Met Val Tyr
65              70              75              80

Leu Gln Met Asn Ser Leu Arg Ala Glu Asp Thr Ala Val Tyr Tyr Cys
                85              90              95

Ala Ala Ala Gly Val Arg Ala Glu Asp Gly Arg Val Arg Thr Leu Pro
            100             105             110

Ser Glu Tyr Asn Phe Trp Gly Gln Gly Thr Gln Val Thr Val Ser Ser
        115             120             125

Ala Ala Ala Glu Val Gln Leu Val Glu Ser Gly Gly Gly Leu Val Gln
    130             135             140

Pro Gly Gly Ser Leu Arg Leu Ser Cys Ala Ala Ser Gly Arg Thr Phe
145             150             155             160

Ser Tyr Asn Pro Met Gly Trp Phe Arg Gln Ala Pro Gly Lys Gly Arg
                165             170             175

Glu Val Val Ala Ala Ile Ser Arg Thr Gly Gly Ser Thr Tyr Tyr Ala
            180             185             190

Arg Ser Val Glu Gly Arg Phe Thr Ile Ser Arg Asp Asn Ala Lys Arg
        195             200             205

Met Val Tyr Leu Gln Met Asn Ser Leu Arg Ala Glu Asp Thr Ala Val
    210             215             220

Tyr Tyr Cys Ala Ala Ala Gly Val Arg Ala Glu Asp Gly Arg Val Arg
225             230             235             240

Thr Leu Pro Ser Glu Tyr Asn Phe Trp Gly Gln Gly Thr Gln Val Thr
                245             250             255

Val Ser Ser

<210> SEQ ID NO 13
<211> LENGTH: 265
<212> TYPE: PRT
<213> ORGANISM: Artificial Sequence
<220> FEATURE:
<223> OTHER INFORMATION: Nanobody sequence

<400> SEQUENCE: 13

Glu Val Gln Leu Val Glu Ser Gly Gly Gly Leu Val Gln Pro Gly Gly
1               5               10              15

Ser Leu Arg Leu Ser Cys Ala Ala Ser Gly Arg Thr Phe Ser Tyr Asn
        20              25              30

Pro Met Gly Trp Phe Arg Gln Ala Pro Gly Lys Gly Arg Glu Leu Val
        35              40              45

Ala Ala Ile Ser Arg Thr Gly Gly Ser Thr Tyr Tyr Pro Asp Ser Val
    50              55              60

Glu Gly Arg Phe Thr Ile Ser Arg Asp Asn Ala Lys Arg Met Val Tyr
65              70              75              80

Leu Gln Met Asn Ser Leu Arg Ala Glu Asp Thr Ala Val Tyr Tyr Cys
                85              90              95

Ala Ala Ala Gly Val Arg Ala Glu Asp Gly Arg Val Arg Thr Leu Pro
            100             105             110
```

-continued

```
Ser Glu Tyr Thr Phe Trp Gly Gln Gly Thr Gln Val Thr Val Ser Ser
        115                 120                 125

Gly Gly Gly Gly Ser Gly Gly Gly Ser Glu Val Gln Leu Val Glu Ser
        130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Gly Arg Glu Leu Val Ala Ala Ile Ser Arg Thr Gly
                180                 185                 190

Gly Ser Thr Tyr Tyr Pro Asp Ser Val Glu Gly Arg Phe Thr Ile Ser
                195                 200                 205

Arg Asp Asn Ala Lys Arg Met Val Tyr Leu Gln Met Asn Ser Leu Arg
        210                 215                 220

Ala Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Thr Phe Trp Gly
                245                 250                 255

Gln Gly Thr Gln Val Thr Val Ser Ser
        260                 265
```

<210> SEQ ID NO 14
<211> LENGTH: 265
<212> TYPE: PRT
<213> ORGANISM: Artificial Sequence
<220> FEATURE:
<223> OTHER INFORMATION: Nanobody sequence

<400> SEQUENCE: 14

```
Glu Val Gln Leu Val Glu Ser Gly Gly Gly Leu Val Gln Pro Gly Gly
1                   5                   10                  15

Ser Leu Arg Leu Ser Cys Ala Ala Ser Gly Arg Thr Phe Ser Tyr Asn
                20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
        50                  55                  60

Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
                100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Glu Val Gln Leu Val Glu Ser
        130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Gly Arg Glu Leu Val Ala Ala Ile Ser Arg Thr Gly
                180                 185                 190

Gly Ser Thr Tyr Tyr Pro Asp Ser Val Glu Gly Arg Phe Thr Ile Ser
                195                 200                 205
```

-continued

```
Arg Asp Asn Ala Lys Arg Ser Val Tyr Leu Gln Met Asn Ser Leu Arg
    210             215                 220

Ala Glu Asp Thr Ala Val Tyr Tyr Cys Ala Ala Ala Gly Val Arg Ala
225             230                 235                 240

Glu Asp Gly Arg Val Arg Thr Leu Pro Ser Glu Tyr Thr Phe Trp Gly
            245                 250                 255

Gln Gly Thr Gln Val Thr Val Ser Ser
            260                 265

<210> SEQ ID NO 15
<211> LENGTH: 265
<212> TYPE: PRT
<213> ORGANISM: Artificial Sequence
<220> FEATURE:
<223> OTHER INFORMATION: Nanobody sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Val Val
            35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
            115                 120                 125

Gly Gly Gly Gly Ser Gly Gly Gly Ser Glu Val Gln Leu Val Glu Ser
            130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Gly Arg Glu Val Val Ala Ala Ile Ser Arg Thr Gly
            180                 185                 190

Gly Ser Thr Tyr Tyr Ala Arg Ser Val Glu Gly Arg Phe Thr Ile Ser
            195                 200                 205

Arg Asp Asn Ala Lys Arg Met Val Tyr Leu Gln Met Asn Ser Leu Arg
    210             215                 220

Ala Glu Asp Thr Ala Val Tyr Tyr Cys Ala Ala Ala Gly Val Arg Ala
225             230                 235                 240

Glu Asp Gly Arg Val Arg Thr Leu Pro Ser Glu Tyr Asn Phe Trp Gly
            245                 250                 255

Gln Gly Thr Gln Val Thr Val Ser Ser
            260                 265

<210> SEQ ID NO 16
<211> LENGTH: 286
<212> TYPE: PRT
<213> ORGANISM: Artificial Sequence
<220> FEATURE:
```

<223> OTHER INFORMATION: Nanobody sequence

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Gly Gly Gly Gly Ser Gly Gly Gly Gly Ser Gly Gly Gly Gly Ser Gly
    130                 135                 140

Gly Gly Gly Ser Gly Gly Gly Gly Ser Gly Gly Gly Gly Ser Glu Val
145                 150                 155                 160

Gln Leu Val Glu Ser Gly Gly Gly Leu Val Gln Pro Gly Gly Ser Leu
            165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Gly Arg Glu Leu Val Ala Ala
        195                 200                 205

Ile Ser Arg Thr Gly Gly Ser Thr Tyr Tyr Pro Asp Ser Val Glu Gly
    210                 215                 220

Arg Phe Thr Ile Ser Arg Asp Asn Ala Lys Arg Met Val Tyr Leu Gln
225                 230                 235                 240

Met Asn Ser Leu Arg Ala Glu Asp Thr Ala Val Tyr Tyr Cys Ala Ala
                245                 250                 255

Ala Gly Val Arg Ala Glu Asp Gly Arg Val Arg Thr Leu Pro Ser Glu
            260                 265                 270

Tyr Thr Phe Trp Gly Gln Gly Thr Gln Val Thr Val Ser Ser
        275                 280                 285
```

<210> SEQ ID NO 17
<211> LENGTH: 286
<212> TYPE: PRT
<213> ORGANISM: Artificial Sequence
<220> FEATURE:
<223> OTHER INFORMATION: Nanobody sequence

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60
```

```
Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Gly Gly Gly Gly Ser Gly Gly Gly Ser Gly Gly Gly Ser Gly
            130                 135                 140

Gly Gly Gly Ser Gly Gly Gly Ser Gly Gly Gly Ser Glu Val
145                 150                 155                 160

Gln Leu Val Glu Ser Gly Gly Gly Leu Val Gln Pro Gly Gly Ser Leu
                165                 170                 175

Arg Leu Ser Cys Ala Ala Ser Gly Arg Thr Phe Ser Tyr Asn Pro Met
                180                 185                 190

Gly Trp Phe Arg Gln Ala Pro Gly Lys Gly Arg Glu Leu Val Ala Ala
            195                 200                 205

Ile Ser Arg Thr Gly Gly Ser Thr Tyr Tyr Pro Asp Ser Val Glu Gly
            210                 215                 220

Arg Phe Thr Ile Ser Arg Asp Asn Ala Lys Arg Ser Val Tyr Leu Gln
225                 230                 235                 240

Met Asn Ser Leu Arg Ala Glu Asp Thr Ala Val Tyr Tyr Cys Ala Ala
                245                 250                 255

Ala Gly Val Arg Ala Glu Asp Gly Arg Val Arg Thr Leu Pro Ser Glu
            260                 265                 270

Tyr Thr Phe Trp Gly Gln Gly Thr Gln Val Thr Val Ser Ser
            275                 280                 285
```

```
<210> SEQ ID NO 18
<211> LENGTH: 286
<212> TYPE: PRT
<213> ORGANISM: Artificial Sequence
<220> FEATURE:
<223> OTHER INFORMATION: Nanobody sequence

<400> SEQUENCE: 18
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Val Val
            35                  40                  45

Ala Ala Ile Ser Arg Thr Gly Gly Ser Thr Tyr Tyr Ala Arg Ser Val
            50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
            115                 120                 125

Gly Gly Gly Gly Ser Gly Gly Gly Gly Ser Gly Gly Gly Gly Ser Gly
            130                 135                 140
```

-continued

```
Gly Gly Gly Ser Gly Gly Gly Ser Gly Gly Gly Ser Glu Val
145             150             155             160

Gln Leu Val Glu Ser Gly Gly Gly Leu Val Gln Pro Gly Gly Ser Leu
            165             170             175

Arg Leu Ser Cys Ala Ala Ser Gly Arg Thr Phe Ser Tyr Asn Pro Met
            180             185             190

Gly Trp Phe Arg Gln Ala Pro Gly Lys Gly Arg Glu Val Val Ala Ala
            195             200             205

Ile Ser Arg Thr Gly Gly Ser Thr Tyr Tyr Ala Arg Ser Val Glu Gly
    210             215             220

Arg Phe Thr Ile Ser Arg Asp Asn Ala Lys Arg Met Val Tyr Leu Gln
225             230             235             240

Met Asn Ser Leu Arg Ala Glu Asp Thr Ala Val Tyr Tyr Cys Ala Ala
            245             250             255

Ala Gly Val Arg Ala Glu Asp Gly Arg Val Arg Thr Leu Pro Ser Glu
            260             265             270

Tyr Asn Phe Trp Gly Gln Gly Thr Gln Val Thr Val Ser Ser
    275             280             285
```

```
<210> SEQ ID NO 19
<211> LENGTH: 128
<212> TYPE: PRT
<213> ORGANISM: Artificial Sequence
<220> FEATURE:
<223> OTHER INFORMATION: Nanobody sequence

<400> SEQUENCE: 19

Glu Val Gln Leu Val Glu Ser Gly Gly Gly Leu Val Gln Pro Gly Gly
1               5               10              15

Ser Leu Arg Leu Ser Cys Ala Ala Ser Gly Arg Thr Phe Ser Tyr Asn
            20              25              30

Pro Met Gly Trp Phe Arg Gln Ala Pro Gly Lys Gly Arg Glu Leu Val
            35              40              45

Ala Ala Ile Ser Arg Thr Gly Gly Ser Thr Tyr Tyr Pro Asp Ser Val
    50              55              60

Glu Gly Arg Phe Thr Ile Ser Arg Asp Asn Ala Lys Arg Met Val Tyr
65              70              75              80

Leu Gln Met Asn Ser Leu Arg Ala Glu Asp Thr Ala Val Tyr Tyr Cys
            85              90              95

Ala Ala Ala Gly Val Arg Ala Glu Asp Gly Arg Val Arg Thr Leu Pro
            100             105             110

Ser Glu Tyr Thr Phe Trp Gly Gln Gly Thr Gln Val Thr Val Ser Ser
    115             120             125
```

```
<210> SEQ ID NO 20
<211> LENGTH: 2804
<212> TYPE: PRT
<213> ORGANISM: Homo sapiens

<400> SEQUENCE: 20

Met Ile Pro Ala Arg Phe Ala Gly Val Leu Leu Ala Leu Ala Leu Ile
1               5               10              15

Leu Pro Gly Thr Leu Cys Ala Glu Gly Thr Arg Gly Arg Ser Ser Thr
            20              25              30

Ala Arg Cys Ser Leu Phe Gly Ser Asp Phe Val Asn Thr Phe Asp Gly
            35              40              45
```

```
Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
                100                 105                 110

Tyr Ala Ser Lys Gly Leu Tyr Leu Glu Thr Glu Ala Gly Tyr Tyr Lys
                115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
                180                 185                 190

Leu Ser Ser Gly Glu Gln Trp Cys Glu Arg Ala Ser Pro Pro Ser Ser
    195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
    275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
                340                 345                 350

Ser Gly Lys Arg Tyr Pro Pro Gly Thr Ser Leu Ser Arg Asp Cys Asn
    355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
                420                 425                 430

Ala Asp Asp Arg Asp Ala Val Cys Thr Arg Ser Val Thr Val Arg Leu
                435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
```

-continued

```
465               470               475               480
Arg Ile Gln His Thr Val Thr Ala Ser Val Arg Leu Ser Tyr Gly Glu
            485               490               495

Asp Leu Gln Met Asp Trp Asp Gly Arg Gly Arg Leu Leu Val Lys Leu
            500               505               510

Ser Pro Val Tyr Ala Gly Lys Thr Cys Gly Leu Cys Gly Asn Tyr Asn
            515               520               525

Gly Asn Gln Gly Asp Asp Phe Leu Thr Pro Ser Gly Leu Ala Glu Pro
    530               535               540

Arg Val Glu Asp Phe Gly Asn Ala Trp Lys Leu His Gly Asp Cys Gln
545               550               555               560

Asp Leu Gln Lys Gln His Ser Asp Pro Cys Ala Leu Asn Pro Arg Met
            565               570               575

Thr Arg Phe Ser Glu Glu Ala Cys Ala Val Leu Thr Ser Pro Thr Phe
            580               585               590

Glu Ala Cys His Arg Ala Val Ser Pro Leu Pro Tyr Leu Arg Asn Cys
            595               600               605

Arg Tyr Asp Val Cys Ser Cys Ser Asp Gly Arg Glu Cys Leu Cys Gly
    610               615               620

Ala Leu Ala Ser Tyr Ala Ala Ala Cys Ala Gly Arg Gly Val Arg Val
625               630               635               640

Ala Trp Arg Glu Pro Gly Arg Cys Glu Leu Asn Cys Pro Lys Gly Gln
            645               650               655

Val Tyr Leu Gln Cys Gly Thr Pro Cys Asn Leu Thr Cys Arg Ser Leu
            660               665               670

Ser Tyr Pro Asp Glu Glu Cys Asn Glu Ala Cys Leu Glu Gly Cys Phe
    675               680               685

Cys Pro Pro Gly Leu Tyr Met Asp Glu Arg Gly Asp Cys Val Pro Lys
    690               695               700

Ala Gln Cys Pro Cys Tyr Tyr Asp Gly Glu Ile Phe Gln Pro Glu Asp
705               710               715               720

Ile Phe Ser Asp His His Thr Met Cys Tyr Cys Glu Asp Gly Phe Met
            725               730               735

His Cys Thr Met Ser Gly Val Pro Gly Ser Leu Leu Pro Asp Ala Val
            740               745               750

Leu Ser Ser Pro Leu Ser His Arg Ser Lys Arg Ser Leu Ser Cys Arg
            755               760               765

Pro Pro Met Val Lys Leu Val Cys Pro Ala Asp Asn Leu Arg Ala Glu
    770               775               780

Gly Leu Glu Cys Thr Lys Thr Cys Gln Asn Tyr Asp Leu Glu Cys Met
785               790               795               800

Ser Met Gly Cys Val Ser Gly Cys Leu Cys Pro Pro Gly Met Val Arg
            805               810               815

His Glu Asn Arg Cys Val Ala Leu Glu Arg Cys Pro Cys Phe His Gln
            820               825               830

Gly Lys Glu Tyr Ala Pro Gly Glu Thr Val Lys Ile Gly Cys Asn Thr
            835               840               845

Cys Val Cys Arg Asp Arg Lys Trp Asn Cys Thr Asp His Val Cys Asp
    850               855               860

Ala Thr Cys Ser Thr Ile Gly Met Ala His Tyr Leu Thr Phe Asp Gly
865               870               875               880

Leu Lys Tyr Leu Phe Pro Gly Glu Cys Gln Tyr Val Leu Val Gln Asp
            885               890               895
```

```
Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
            915                 920                 925

Val Glu Gly Gly Glu Ile Glu Leu Phe Asp Gly Glu Val Asn Val Lys
        930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
    1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
    1145                1150                1155

His Pro  Glu Pro Leu Ala Cys  Pro Val Gln Cys Val  Glu Gly Cys
    1160                1165                1170

His Ala  His Cys Pro Pro Gly  Lys Ile Leu Asp Glu  Leu Leu Gln
    1175                1180                1185

Thr Cys  Val Asp Pro Glu Asp  Cys Pro Val Cys Glu  Val Ala Gly
    1190                1195                1200

Arg Arg  Phe Ala Ser Gly Lys  Lys Val Thr Leu Asn  Pro Ser Asp
    1205                1210                1215

Pro Glu  His Cys Gln Ile Cys  His Cys Asp Val Val  Asn Leu Thr
    1220                1225                1230

Cys Glu  Ala Cys Gln Glu Pro  Gly Gly Leu Val Val  Pro Pro Thr
    1235                1240                1245

Asp Ala  Pro Val Ser Pro Thr  Thr Leu Tyr Val Glu  Asp Ile Ser
    1250                1255                1260

Glu Pro  Pro Leu His Asp Phe  Tyr Cys Ser Arg Leu  Leu Asp Leu
    1265                1270                1275

Val Phe  Leu Leu Asp Gly Ser  Ser Arg Leu Ser Glu  Ala Glu Phe
    1280                1285                1290
```

-continued

```
Glu Val Leu Lys Ala Phe Val Val Asp Met Met Glu Arg Leu Arg
    1295             1300             1305

Ile Ser Gln Lys Trp Val Arg Val Ala Val Val Glu Tyr His Asp
    1310             1315             1320

Gly Ser His Ala Tyr Ile Gly Leu Lys Asp Arg Lys Arg Pro Ser
    1325             1330             1335

Glu Leu Arg Arg Ile Ala Ser Gln Val Lys Tyr Ala Gly Ser Gln
    1340             1345             1350

Val Ala Ser Thr Ser Glu Val Leu Lys Tyr Thr Leu Phe Gln Ile
    1355             1360             1365

Phe Ser Lys Ile Asp Arg Pro Glu Ala Ser Arg Ile Ala Leu Leu
    1370             1375             1380

Leu Met Ala Ser Gln Glu Pro Gln Arg Met Ser Arg Asn Phe Val
    1385             1390             1395

Arg Tyr Val Gln Gly Leu Lys Lys Lys Lys Val Ile Val Ile Pro
    1400             1405             1410

Val Gly Ile Gly Pro His Ala Asn Leu Lys Gln Ile Arg Leu Ile
    1415             1420             1425

Glu Lys Gln Ala Pro Glu Asn Lys Ala Phe Val Leu Ser Ser Val
    1430             1435             1440

Asp Glu Leu Glu Gln Gln Arg Asp Glu Ile Val Ser Tyr Leu Cys
    1445             1450             1455

Asp Leu Ala Pro Glu Ala Pro Pro Pro Thr Leu Pro Pro His Met
    1460             1465             1470

Ala Gln Val Thr Val Gly Pro Gly Leu Arg Asn Ser Met Val Leu
    1475             1480             1485

Asp Val Ala Phe Val Leu Glu Gly Ser Asp Lys Ile Gly Glu Ala
    1490             1495             1500

Asp Phe Asn Arg Ser Lys Glu Phe Met Glu Glu Val Ile Gln Arg
    1505             1510             1515

Met Asp Val Gly Gln Asp Ser Ile His Val Thr Val Leu Gln Tyr
    1520             1525             1530

Ser Tyr Met Val Thr Val Glu Tyr Pro Phe Ser Glu Ala Gln Ser
    1535             1540             1545

Lys Gly Asp Ile Leu Gln Arg Val Arg Glu Ile Arg Tyr Gln Gly
    1550             1555             1560

Gly Asn Arg Thr Asn Thr Gly Leu Ala Leu Arg Tyr Leu Ser Asp
    1565             1570             1575

His Ser Phe Leu Val Ser Gln Gly Asp Arg Glu Gln Ala Pro Asn
    1580             1585             1590

Leu Val Tyr Met Val Thr Gly Asn Pro Ala Ser Asp Glu Ile Lys
    1595             1600             1605

Arg Leu Pro Gly Asp Ile Gln Val Val Pro Ile Gly Val Gly Pro
    1610             1615             1620

Asn Ala Asn Val Gln Glu Leu Glu Arg Ile Gly Trp Pro Asn Ala
    1625             1630             1635

Pro Ile Leu Ile Gln Asp Phe Glu Thr Leu Pro Arg Glu Ala Pro
    1640             1645             1650

Asp Leu Val Leu Gln Arg Cys Cys Ser Gly Glu Gly Leu Gln Ile
    1655             1660             1665

Pro Thr Leu Ser Pro Ala Pro Asp Cys Ser Gln Pro Leu Asp Val
    1670             1675             1680

Ile Leu Leu Leu Asp Gly Ser Ser Ser Phe Pro Ala Ser Tyr Phe
```

```
           1685                 1690                 1695

Asp Glu  Met Lys Ser Phe Ala  Lys Ala Phe Ile Ser  Lys Ala Asn
    1700                 1705                 1710

Ile Gly  Pro Arg Leu Thr Gln  Val Ser Val Leu Gln  Tyr Gly Ser
    1715                 1720                 1725

Ile Thr  Thr Ile Asp Val Pro  Trp Asn Val Val Pro  Glu Lys Ala
    1730                 1735                 1740

His Leu  Leu Ser Leu Val Asp  Val Met Gln Arg Glu  Gly Gly Pro
    1745                 1750                 1755

Ser Gln  Ile Gly Asp Ala Leu  Gly Phe Ala Val Arg  Tyr Leu Thr
    1760                 1765                 1770

Ser Glu  Met His Gly Ala Arg  Pro Gly Ala Ser Lys  Ala Val Val
    1775                 1780                 1785

Ile Leu  Val Thr Asp Val Ser  Val Asp Ser Val Asp  Ala Ala Ala
    1790                 1795                 1800

Asp Ala  Ala Arg Ser Asn Arg  Val Thr Val Phe Pro  Ile Gly Ile
    1805                 1810                 1815

Gly Asp  Arg Tyr Asp Ala Ala  Gln Leu Arg Ile Leu  Ala Gly Pro
    1820                 1825                 1830

Ala Gly  Asp Ser Asn Val Val  Lys Leu Gln Arg Ile  Glu Asp Leu
    1835                 1840                 1845

Pro Thr  Met Val Thr Leu Gly  Asn Ser Phe Leu His  Lys Leu Cys
    1850                 1855                 1860

Ser Gly  Phe Val Arg Ile Cys  Met Asp Glu Asp Gly  Asn Glu Lys
    1865                 1870                 1875

Arg Pro  Gly Asp Val Trp Thr  Leu Pro Asp Gln Cys  His Thr Val
    1880                 1885                 1890

Thr Cys  Gln Pro Asp Gly Gln  Thr Leu Leu Lys Ser  His Arg Val
    1895                 1900                 1905

Asn Cys  Asp Arg Gly Leu Arg  Pro Ser Cys Pro Asn  Ser Gln Ser
    1910                 1915                 1920

Pro Val  Lys Val Glu Glu Thr  Cys Gly Cys Arg Trp  Thr Cys Pro
    1925                 1930                 1935

Cys Val  Cys Thr Gly Ser Ser  Thr Arg His Ile Val  Thr Phe Asp
    1940                 1945                 1950

Gly Gln  Asn Phe Lys Leu Thr  Gly Ser Cys Ser Tyr  Val Leu Phe
    1955                 1960                 1965

Gln Asn  Lys Glu Gln Asp Leu  Glu Val Ile Leu His  Asn Gly Ala
    1970                 1975                 1980

Cys Ser  Pro Gly Ala Arg Gln  Gly Cys Met Lys Ser  Ile Glu Val
    1985                 1990                 1995

Lys His  Ser Ala Leu Ser Val  Glu Leu His Ser Asp  Met Glu Val
    2000                 2005                 2010

Thr Val  Asn Gly Arg Leu Val  Ser Val Pro Tyr Val  Gly Gly Asn
    2015                 2020                 2025

Met Glu  Val Asn Val Tyr Gly  Ala Ile Met His Glu  Val Arg Phe
    2030                 2035                 2040

Asn His  Leu Gly His Ile Phe  Thr Phe Thr Pro Gln  Asn Asn Glu
    2045                 2050                 2055

Phe Gln  Leu Gln Leu Ser Pro  Lys Thr Phe Ala Ser  Lys Thr Tyr
    2060                 2065                 2070

Gly Leu  Cys Gly Ile Cys Asp  Glu Asn Gly Ala Asn  Asp Phe Met
    2075                 2080                 2085
```

```
Leu Arg Asp Gly Thr Val Thr  Thr Asp Trp Lys Thr  Leu Val Gln
    2090             2095             2100

Glu Trp Thr Val Gln Arg Pro  Gly Gln Thr Cys Gln  Pro Ile Leu
    2105             2110             2115

Glu Glu Gln Cys Leu Val Pro  Asp Ser Ser His Cys  Gln Val Leu
    2120             2125             2130

Leu Leu Pro Leu Phe Ala Glu  Cys His Lys Val Leu  Ala Pro Ala
    2135             2140             2145

Thr Phe Tyr Ala Ile Cys Gln  Gln Asp Ser Cys His  Gln Glu Gln
    2150             2155             2160

Val Cys Glu Val Ile Ala Ser  Tyr Ala His Leu Cys  Arg Thr Asn
    2165             2170             2175

Gly Val Cys Val Asp Trp Arg  Thr Pro Asp Phe Cys  Ala Met Ser
    2180             2185             2190

Cys Pro Pro Ser Leu Val Tyr  Asn His Cys Glu His  Gly Cys Pro
    2195             2200             2205

Arg His Cys Asp Gly Asn Val  Ser Ser Cys Gly Asp  His Pro Ser
    2210             2215             2220

Glu Gly Cys Phe Cys Pro Pro  Asp Lys Val Met Leu  Glu Gly Ser
    2225             2230             2235

Cys Val Pro Glu Glu Ala Cys  Thr Gln Cys Ile Gly  Glu Asp Gly
    2240             2245             2250

Val Gln His Gln Phe Leu Glu  Ala Trp Val Pro Asp  His Gln Pro
    2255             2260             2265

Cys Gln Ile Cys Thr Cys Leu  Ser Gly Arg Lys Val  Asn Cys Thr
    2270             2275             2280

Thr Gln Pro Cys Pro Thr Ala  Lys Ala Pro Thr Cys  Gly Leu Cys
    2285             2290             2295

Glu Val Ala Arg Leu Arg Gln  Asn Ala Asp Gln Cys  Cys Pro Glu
    2300             2305             2310

Tyr Glu Cys Val Cys Asp Pro  Val Ser Cys Asp Leu  Pro Pro Val
    2315             2320             2325

Pro His Cys Glu Arg Gly Leu  Gln Pro Thr Leu Thr  Asn Pro Gly
    2330             2335             2340

Glu Cys Arg Pro Asn Phe Thr  Cys Ala Cys Arg Lys  Glu Glu Cys
    2345             2350             2355

Lys Arg Val Ser Pro Pro Ser  Cys Pro Pro His Arg  Leu Pro Thr
    2360             2365             2370

Leu Arg Lys Thr Gln Cys Cys  Asp Glu Tyr Glu Cys  Ala Cys Asn
    2375             2380             2385

Cys Val Asn Ser Thr Val Ser  Cys Pro Leu Gly Tyr  Leu Ala Ser
    2390             2395             2400

Thr Ala Thr Asn Asp Cys Gly  Cys Thr Thr Thr Cys  Leu Pro
    2405             2410             2415

Asp Lys Val Cys Val His Arg  Ser Thr Ile Tyr Pro  Val Gly Gln
    2420             2425             2430

Phe Trp Glu Glu Gly Cys Asp  Val Cys Thr Cys Thr  Asp Met Glu
    2435             2440             2445

Asp Ala Val Met Gly Leu Arg  Val Ala Gln Cys Ser  Gln Lys Pro
    2450             2455             2460

Cys Glu Asp Ser Cys Arg Ser  Gly Phe Thr Tyr Val  Leu His Glu
    2465             2470             2475
```

-continued

```
Gly Glu Cys Cys Gly Arg Cys  Leu Pro Ser Ala Cys  Glu Val Val
    2480                2485                2490

Thr Gly Ser Pro Arg Gly Asp  Ser Gln Ser Ser Trp  Lys Ser Val
    2495                2500                2505

Gly Ser Gln Trp Ala Ser Pro  Glu Asn Pro Cys Leu  Ile Asn Glu
    2510                2515                2520

Cys Val Arg Val Lys Glu Glu  Val Phe Ile Gln Gln  Arg Asn Val
    2525                2530                2535

Ser Cys Pro Gln Leu Glu Val  Pro Val Cys Pro Ser  Gly Phe Gln
    2540                2545                2550

Leu Ser Cys Lys Thr Ser Ala  Cys Cys Pro Ser Cys  Arg Cys Glu
    2555                2560                2565

Arg Met Glu Ala Cys Met Leu  Asn Gly Thr Val Ile  Gly Pro Gly
    2570                2575                2580

Lys Thr Val Met Ile Asp Val  Cys Thr Thr Cys Arg  Cys Met Val
    2585                2590                2595

Gln Val Gly Val Ile Ser Gly  Phe Lys Leu Glu Cys  Arg Lys Thr
    2600                2605                2610

Thr Cys Asn Pro Cys Pro Leu  Gly Tyr Lys Glu Glu  Asn Asn Thr
    2615                2620                2625

Gly Glu Cys Cys Gly Arg Cys  Leu Pro Thr Ala Cys  Thr Ile Gln
    2630                2635                2640

Leu Arg Gly Gly Gln Ile Met  Thr Leu Lys Arg Asp  Glu Thr Leu
    2645                2650                2655

Gln Asp Gly Cys Asp Thr His  Phe Cys Lys Val Asn  Glu Arg Gly
    2660                2665                2670

Glu Tyr Phe Trp Glu Lys Arg  Val Thr Gly Cys Pro  Pro Phe Asp
    2675                2680                2685

Glu His Lys Cys Leu Ala Glu  Gly Gly Lys Ile Met  Lys Ile Pro
    2690                2695                2700

Gly Thr Cys Cys Asp Thr Cys  Glu Glu Pro Glu Cys  Asn Asp Ile
    2705                2710                2715

Thr Ala Arg Leu Gln Tyr Val  Lys Val Gly Ser Cys  Lys Ser Glu
    2720                2725                2730

Val Glu Val Asp Ile His Tyr  Cys Gln Gly Lys Cys  Ala Ser Lys
    2735                2740                2745

Ala Met Tyr Ser Ile Asp Ile  Asn Asp Val Gln Asp  Gln Cys Ser
    2750                2755                2760

Cys Cys Ser Pro Thr Arg Thr  Glu Pro Met Gln Val  Ala Leu His
    2765                2770                2775

Cys Thr Asn Gly Ser Val Val  Tyr His Glu Val Leu  Asn Ala Met
    2780                2785                2790

Glu Cys Lys Cys Ser Pro Arg  Lys Cys Ser Lys
    2795                2800
```

STABLE FORMULATIONS OF IMMUNOGLOBULIN SINGLE VARIABLE DOMAINS

RELATED APPLICATIONS

This application is a continuation of U.S. application Ser. No. 14/891,441, filed Nov. 16, 2015 and now issued as U.S. Pat. No. 10,035,862, which is a national stage filing under 35 U.S.C. § 371 of international application PCT/EP2014/ 060107, filed May 16, 2014, which was published under PCT Article 21(2) in English, and claims the benefit under 35 U.S.C. § 119(e) of U.S. provisional application Ser. No. 61/824,523, filed May 17, 2013, the disclosures of which are incorporated by reference herein in their entireties.

FIELD OF THE INVENTION

The present invention relates to stable formulations of polypeptides, e.g. immunoglobulin single variable domains, in particular immunoglobulin single variable domains directed against von Willebrand Factor (vWF), such as immunoglobulin single variable domains according to SEQ ID NO:s 1-19, specifically SEQ ID NO: 1, i.e. the Nanobody ALX-0081.

The invention provides formulations which are stable upon storage for prolonged periods of time and over a broad range of temperatures. The formulations of the invention ensure a high stability of the polypeptide, allowing multiple freeze-thaw cycles without chemical or physical deterioration, and provide stability in relation to mechanical stress, such as shake, shear or stir stress. They are suitable for pharmaceutical and diagnostic preparations and compatible with pharmaceutically acceptable diluents, such as saline, Ringer's solution or glucose/dextrose solution.

The present invention also relates to methods of preparation, methods for storage and uses of the formulations. The invention further relates to dosage unit forms, kits and medical uses of the formulations.

BACKGROUND OF THE INVENTION

Immunoglobulin single variable domains, such as camelid VHH domains, camelized VH domains or humanized VHH domains, represent a rapidly growing class of antibody therapeutics. For example, immunoglobulin single variable domains against vWF have been described in WO2004/ 015425, WO2004/062551, WO2006/074947, WO2006/ 122825, WO2009/115614, and WO2011/067160.

Proteins such as immunoglobulin single variable domains (ISVDs) typically must be stored and transported between initial manufacture and use, e.g. administration to a patient. Transport, manufacture, storage and delivery processes can exert manifold stresses on the immunoglobulin single variable domain, such as chemical and physical stresses. During storage chemical modifications can occur such as, for instance, deamidation, racemization, hydrolysis, oxidation, isomerization, beta-elimination or disulfide exchange. Physical stresses can cause denaturation and unfolding, aggregation, particulate formation, precipitation, opalescence or adsorption.

There remains a need for providing formulations for immunoglobulin single variable domains, e.g. as defined herein, which enhance stability, preserve the active agent against chemical and/or mechanical stress, and hence allow storage and temperature changes without significant physical or chemical deterioration, remain stable for prolonged periods of time, and/or are patient friendly, e.g. in which the active agent is soluble at high concentration.

SUMMARY OF THE INVENTION

It is known that the above mentioned stresses can affect the physicochemical integrity of protein therapeutics, e.g. antibody therapeutics. For example, aggregation, deamidation and oxidation have been described as most common causes of antibody degradation (Cleland et al., 1993, Crit. Rev. Ther. Drug Carrier Systems 10, 307-377). At the same time it is instrumental that formulations are provided which preserve chemical and physical integrity of the immunoglobulin single variable domains. Chemical and physical integrity are required for use as e.g. a therapeutic agent, and typically are also associated with biological activity. Although our knowledge of protein stability is increasing, optimizing formulation conditions to completely suppress or minimize these manifold stresses and ensure a prolonged shelf-life remains a major challenge.

Little is known about suitable formulations of immunoglobulin single variable domains. WO2010/077422 describes a formulation of a TNF binding Nanobody comprising a lyoprotectant, surfactant and a buffer chosen from histidine buffer and Tris-HCl buffer at a pH between 5.0 to 7.5.

Specific vWF binders, and in particular immunoglobulin single variable domains with high affinity to vWF such as ALX-0081 [INN: caplacizumab], have been tested as adjunctive therapy for patients with acute coronary syndrome (ACS) undergoing percutaneous coronary intervention (PCI) and are developed as treatment of thrombotic thrombocytopenic purpura (TTP). Phase I clinical trials have been completed successfully and testing in Phase II trials is currently on-going. Thus far, ALX-0081 has been presented as a phosphate based liquid formulation containing 5 mg/mL of the active pharmaceutical ingredient (API) in D-PBS, 200 mM glycine and 0.02% Tween-80 (v/v).

Although this formulation proved to be effective, it may be improved in several manners. First, the current concentration would probably necessitate multiple subcutaneous injections (assuming the volume per subcutaneous injection is restricted to about 1 mL) thus reducing patient friendliness and convenience. Secondly, the storage stability and shelf-life of the current formulation of ALX-0081 (hereinafter also referred to as contemporaneous ALX-0081) can be improved at elevated temperatures. The stability in the present formulation at high temperatures is mainly determined by chemical modifications on the polypeptide. Chemical modifications may be linked with potency loss. Although a practicable shelf-life can be achieved by storing the product at −20° C., this is, however, not considered to be a favourable option for most practical purposes.

Freeze-drying is a commonly employed technique for preserving proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage (Arakawa et al. Pharm. Res. 8(3):285-291 (1991)).

The present invention relates to a formulation comprising a von Willebrand Factor (vWF) binder and a citrate or phosphate buffer, preferably a citrate buffer, with a pH in the range of 5.0 to 7.5. In particular, the present invention relates to a formulation as described herein, wherein said vWF binder comprises at least one immunoglobulin single variable domain binding to SEQ ID NO: 20.

Said immunoglobulin single variable domain comprises or essentially consists of, but is not limited to, an immunoglobulin single variable domain that is a heavy chain variable domain sequence, more specifically an immunoglobulin single variable domain which is a heavy chain variable domain sequence which is derived from a conventional four-chain antibody or a heavy chain variable domain sequence which is derived from a heavy chain antibody, or a Nanobody (including but not limited to a VHH sequence), preferably a Nanobody.

In addition, the present invention relates to a formulation as described herein, wherein said vWF binder comprises at least one of SEQ ID NO:s 1-19. Moreover, the present invention relates to a formulation as described herein, wherein said vWF binder is a single chain polypeptide comprising one or more immunoglobulin single variable domains, preferably wherein said vWF-binder is monovalent or multivalent, wherein said vWF-binder is monospecific or multispecific and/or wherein one or more immunoglobulin single variable domains are CDR-grafted, humanized, camelized, de-immunized, and/or in vitro generated (e.g. selected by phage display). The present invention also relates to a formulation as described herein, wherein said vWF binder comprises an amino acid sequence which is at least 90% identical to SEQ ID NO: 1. The present invention relates also to a formulation as described herein, wherein said vWF binder has a concentration in the range of 0.1 to 80 mg/mL, and/or wherein said buffer has a concentration in the range of 5-200 mM.

Additionally, the present invention relates to a formulation as described herein, further comprising an excipient, preferably said excipient has a concentration in the range of 10-500 mM, more preferably, wherein said excipient is selected from the list consisting of sucrose, glycine, mannitol, trehalose and NaCl, even more preferably, wherein said sucrose has a concentration in the range of 1-15%, preferably 2-12%, preferably 4-10%, e.g. 4, 5, 6, 7, 8 or 9% (w/v), most preferably 7%.

The present invention also relates to a formulation as described herein, wherein the buffer is selected from a citrate buffer, preferably said citrate buffer has a pH between 6.0 and 7.0, more preferably 6.5; and a phosphate buffer, preferably said phosphate buffer has a pH in the range of 6.5 to 7.5, preferably 7.1.

In addition, the present invention relates to a formulation as described herein, further comprising a non-ionic detergent, such as Tween-80, preferably in a concentration between 0.001 and 0.5% (v/v), more preferably 0.01-0.02% (v/v).

Furthermore, the present invention relates to a formulation as described herein, wherein said buffer is a citrate buffer at pH 6.5±0.5, e.g. 6.2, 6.3, 6.4, 6.5, 6.6, 6.7 or 6.8, more specifically 6.5, and wherein said formulation further comprises sucrose having a concentration in the range of 1-15%, preferably 2-12%, preferably 4-10%, e.g. 4, 5, 6, 7, 8 or 9% (w/v), most preferably 7%, and preferably further comprises a non-ionic detergent such as Tween-80, preferably at a concentration of 0.01% (v/v).

Also, the present invention relates to a formulation as described herein, wherein said formulation has an osmolality in the range of 290±60 mOsm/kg, more preferably in the range of 290±20 mOsm/kg.

The present invention further relates to a formulation comprising:

(a) a vWF binder at a concentration from about 0.1 mg/mL to about 80 mg/mL;

(b) an excipient chosen from sucrose, glycine, mannitol, trehalose or NaCl at a concentration of about 1% to about 15% (w/v);

(c) Tween-80 at a concentration of about 0.001% to 0.5% (v/v); and (d) a buffer chosen from citrate buffer at a concentration of about 5 mM to about 200 mM such that the pH of the formulation is about 6.0 to 7.0 and a phosphate buffer at a concentration of about 10 mM to about 50 mM such that the pH of the formulation is about 6.5 to 7.5, wherein the vWF binder in the formulation retains at least about 80% of its stability after storage for at least 12 months at 5° C. or even 24 months at 5° C.

The invention also relates to a formulation which has less than 5% of high molecular weight (HMW) species after storage for at least 12 months at 5° C. or even 24 months at 5° C.; and/or less than 5% of low molecular weight (LMW) species after storage for at least 12 months at 5° C. or even 24 months at 5° C.

The invention further relates to a formulation wherein at least 80%, preferably at least 90%, more preferably at least 95% or even at least 99% of the vWF binder retains it binding activity after storage compared to the binding activity prior to storage, said binding activity as measured by ELISA and/or Biacore.

In addition, the invention relates to a formulation as described herein, wherein said formulation is in a liquid, lyophilized, spray-dried, reconstituted lyophilized or frozen form, more specifically the invention pertains to a liquid or reconstituted lyophilized formulation comprising:

(a) a vWF binder at a concentration from about 0.1 mg/mL to about 80 mg/mL;

(b) sucrose at a concentration of about 1% to about 15% (w/v);

(c) Tween-80 at a concentration of about 0.001%-0.5% (v/v); and (d) a citrate buffer at a concentration of about 5 mM to about 200 mM, such that the pH of the formulation is about 6.0 to 7.0.

The lyophilized formulation can then be reconstituted as needed by mixing the lyophilized form with a suitable diluent (e.g. water) to resolubilize the original formulation components to a desired concentration.

The present invention also relates to a formulation as described herein, wherein said formulation is a bulk storage formulation comprising:

(a) a vWF binder at a concentration from about 0.1 mg/mL to about 80 mg/mL;

(b) sucrose at a concentration of about 1% to about 15%;

(c) Tween-80 at a concentration of about 0.001%-0.5% (w/v); and (d) a citrate buffer at a concentration of about 5 mM to about 200 mM, such that the pH of the formulation is about 6.0 to 7.0, wherein at least 100 liters of the formulation are stored at below freezing conditions.

In addition, the present invention relates to a formulation, wherein said formulation is suitable for parenteral administration to a subject, e.g., a human subject (e.g. a patient having a vWF-related disorder). The formulation can be administered to the subject by injection (e.g., intravenous, subcutaneous, intramuscular or intraperitoneal).

Also, the present invention provides a formulation as described herein, for use in a method of treating a human or animal subject, preferably for use in treating vWF-related disorders, such as e.g. acute coronary syndrome (ACS), transient cerebral ischemic attack, unstable or stable angina pectoris, stroke, myocardial infarction or thrombotic thrombocytopenic purpura (TTP), most preferably for use in treating TTP or ACS. Moreover, the present invention pertains to a method or process of preparing the formulation as described herein. The method or process includes expressing the vWF binder in a cell culture; purifying the vWF binder, e.g., by passing the vWF binder through at least one of a chromatography purification step, an ultrafiltration/diafiltration steps; adjusting the concentration of the vWF binder, e.g., to about 0.1 to 80 mg/mL in a formulation containing a lyoprotectant, a surfactant and a buffer as described herein, e.g., sucrose at a concentration of about 1% to about 15%; Tween-80 at a concentration of about 0.001% to about 0.5% (w/v); and a citrate buffer at a concentration of about 5 mM to about 200 mM, such that the pH of the formulation is about 6.0 to 7.0; and optionally comprising a step of confectioning the formulation in a dosage unit form.

The invention also features a method or process for preparing a reconstituted formulation containing a vWF binder, e.g., ALX-0081 as described herein. The method includes: lyophilizing a mixture of a vWF binder, a lyoprotectant, a surfactant and a buffer, thereby forming a lyophilized mixture; and reconstituting the lyophilized mixture in a diluent, thereby preparing a formulation as described herein. In particular, the formulation includes (a) a vWF binder, e.g., ALX-0081 at a concentration of about 0.1 to about 80 mg/mL; (b) sucrose at a concentration of about 1% to about 15% (w/v); (c) Tween-80 at a concentration of about 0.001% to about 0.5% (v/v); and (d) a citrate buffer at a concentration of about 5 to about 200 mM, such that the pH of the formulation is about 6 to 7.0; and optionally comprising a step of confectioning the formulation in a dosage unit form.

The present invention further relates to a method for stabilizing a vWF binder, preferably a polypeptide comprising at least one of SEQ ID NOs: 1-19 for storage, comprising preparing a formulation as defined herein.

In addition, the invention relates to a method for storing a vWF binder, preferably a polypeptide comprising at least one of SEQ ID NOs: 1-19, comprising preparing a formulation as defined herein.

Also provided are pharmaceutical or diagnostic compositions comprising any of the formulations described herein or obtainable by the methods described herein.

Further, the invention features a method of analyzing a product or a process, e.g., a manufacturing process. The method includes providing a formulation of a vWF binder, e.g., ALX-0081 as described herein, and assessing a parameter of the formulation, such as color, clarity, viscosity or an amount of one or more HMW, LMW species, as described herein. The evaluation can include an assessment of one or more parameters, such as determining whether the parameter meets a preselected criterion, e.g., determining whether the preselected criterion is present, or is present in a preselected range, thereby analyzing the process. For example, evaluation of the process includes a measure of the stability of the vWF binder formulation. Stability of the ALX-0081 formulation can be measured, for example, by aggregate formation, which is assayed, e.g., by size exclusion high pressure liquid chromatography (SE-HPLC), by color, clarity, or viscosity as described herein.

In addition, the method may further comprise comparing two or more sample formulations in a method of monitoring or controlling batch-to-batch variation, comparing a preparation to a reference standard, classifying, selecting, accepting or discarding, releasing or withholding, processing into a drug product, shipping, moving to a different location, formulating, labelling, or packaging the formulation, based upon the comparison. Also, the method may further comprise providing a record which includes data relating to the assessed parameter of the formulation and optionally includes an identifier for a batch of the formulation; submitting said record to a decision-maker; optionally, receiving a communication from said decision maker; optionally, deciding whether to release or market the batch of formulation based on the communication from the decision maker.

Also provided are kits or articles of manufacture comprising the formulation of the invention and instructions for use by, e.g., a healthcare professional. The kits or articles of manufacture may include a vial or a syringe containing the formulation of the invention as described herein. Preferably, the vial or syringe is composed of glass, plastic, or a polymeric material chosen from a cyclic olefin polymer or copolymer. Furthermore, the formulation can also be present in an injectable device (e.g., an injectable syringe, e.g. a prefilled injectable syringe).

The invention further provides pharmaceutical unit dosage forms comprising the stable formulations of the invention which are suited for parenteral administration (e.g., intradermally, intramuscularly, intraperitoneally, intravenously and subcutaneously) of the formulation of the invention to a human patient.

Moreover, the formulations of the invention can be used for storage of a vWF binder, preferably a polypeptide comprising at least one of SEQ ID NO:s 1-19, such as ALX-0081 as described herein, wherein said storage is 1-36 months, such as 1, 1.5, 3, 6, 9, 12, 18, 24, 30 or 36 months, preferably at least 12 months, e.g. at a temperature between −70° C. and +40° C., such as −70° C., −20° C., +5° C., +25° C. or +40° C., preferably a temperature between −70° C. and +25° C.

The present invention also relates to a method of treating or preventing a vWF-related disorder, such as e.g. acute coronary syndrome (ACS), transient cerebral ischemic attack, unstable or stable angina pectoris, stroke, myocardial infarction or thrombotic thrombocytopenic purpura (TTP); said method comprising administering to a subject a pharmaceutical composition comprising the formulation of the invention, thereby reducing one or more symptoms associated with said vWF-related disorder. In particular, said vWF-related disorder is UP.

Figure 4A:
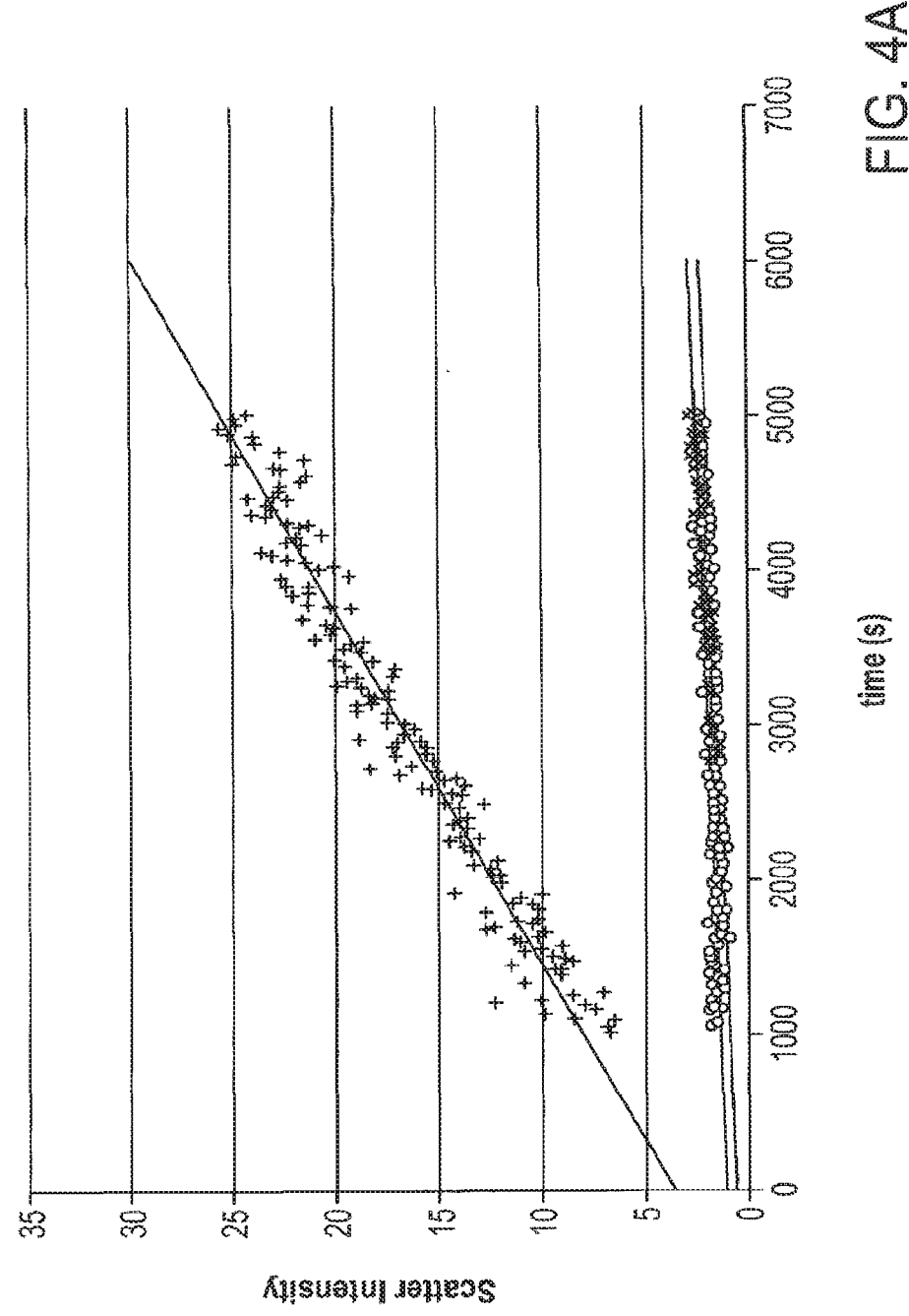

FIG. 4A Scatter intensity of stirred ALX-0081 samples in 50 mM citrate pH 6.0, 50 mM citrate pH 6.0+0.01% Tween-80 (v/v) and 50 mM citrate pH 6.0+0.02% Tween-80 (v/v) at +25° C. '+' represent samples in 50 mM citrate pH 10 6.0 (y=0.0044x+3.5962, $R^2$=0.9549); 'o' represent samples in 50 mM citrate pH 6.0+0.02% Tween-80 (v/v) (y=0.0002x+1.0447, $R^2$=0.4673); '×' represent samples in 50 mM citrate pH 6.0+0.01% Tween-80 (v/v) (y=0.0004x+ 0.5125, $R^2$=0.6804); (x-axis=time in seconds; y-axis=scatter 15 intensity).

Figure 4B:
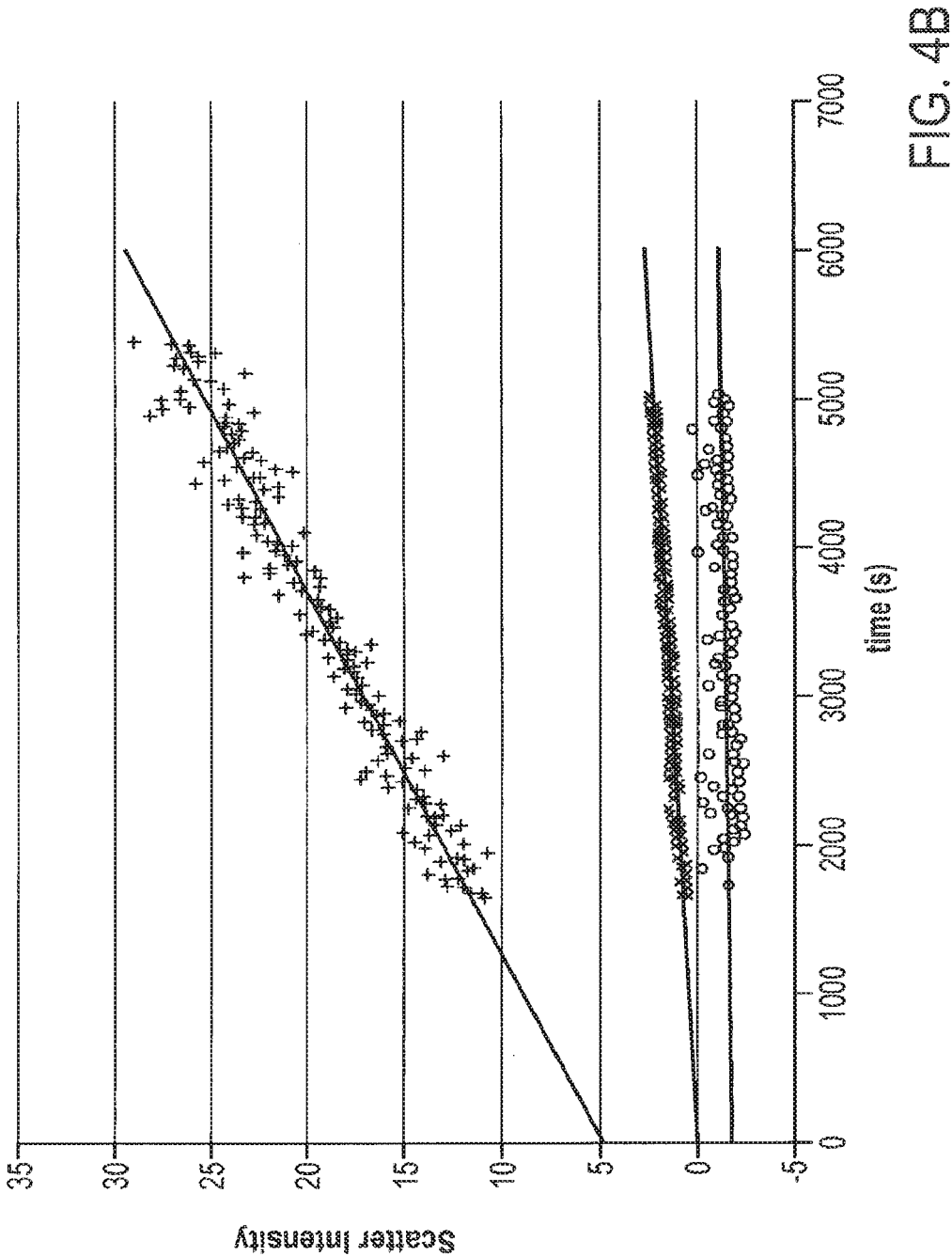

FIG. 4B Scatter intensity of stirred ALX-0081 samples in 50 mM citrate pH 6.5, 50 mM citrate pH 6.5+0.01% Tween-80 (v/v) and 50 mM citrate pH 6.5+0.02% Tween-80 (v/v) at +25° C. '+' represent samples in 50 mM citrate pH 20 6.5 (y=0.0041x+4.7667, $R^2$=0.9431); 'o' represent samples in 50 mM citrate pH 6.5+0.02% Tween-80 (v/v) (y=0.0004x−0.0208, $R^2$=0.9391); '×' represent samples in 50 mM citrate pH 6.5+0.01% Tween-80 (v/v) (y=0.0001x− 1.8853, $R^2$=0.0376); (x-axis=time in seconds; y-axis=scatter 25 intensity).

Figure 5:
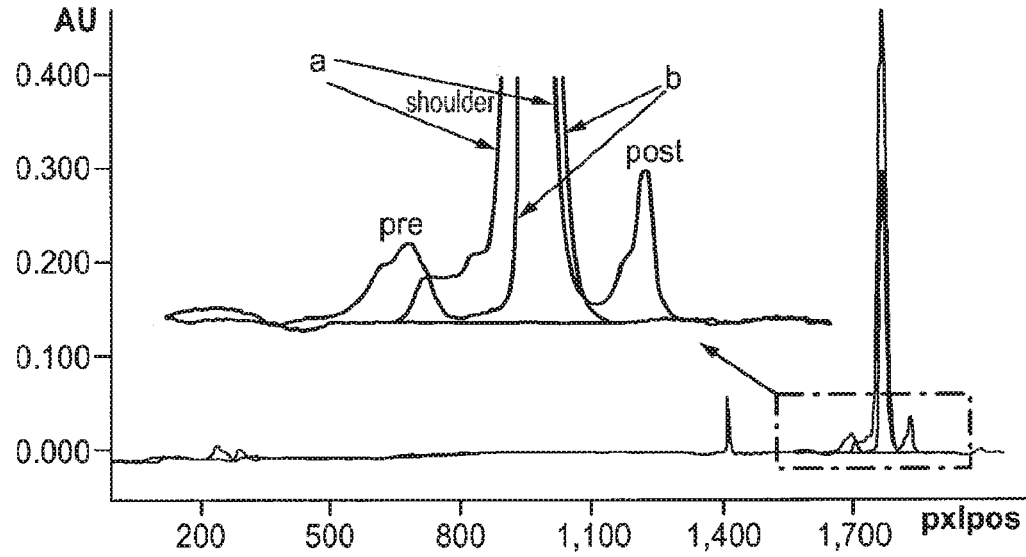

FIG. 5 Overlay of the cIEF profiles of ALX-0081 at 5 mg/mL in D-PBS+200 mM glycine+0.01% Tween-80 after 1 month storage at +40° C. (a) and −70° C. (b); (λ=280 nm). AU: absorbance unit; pxlpos: pixelposition.

Figure 6A:
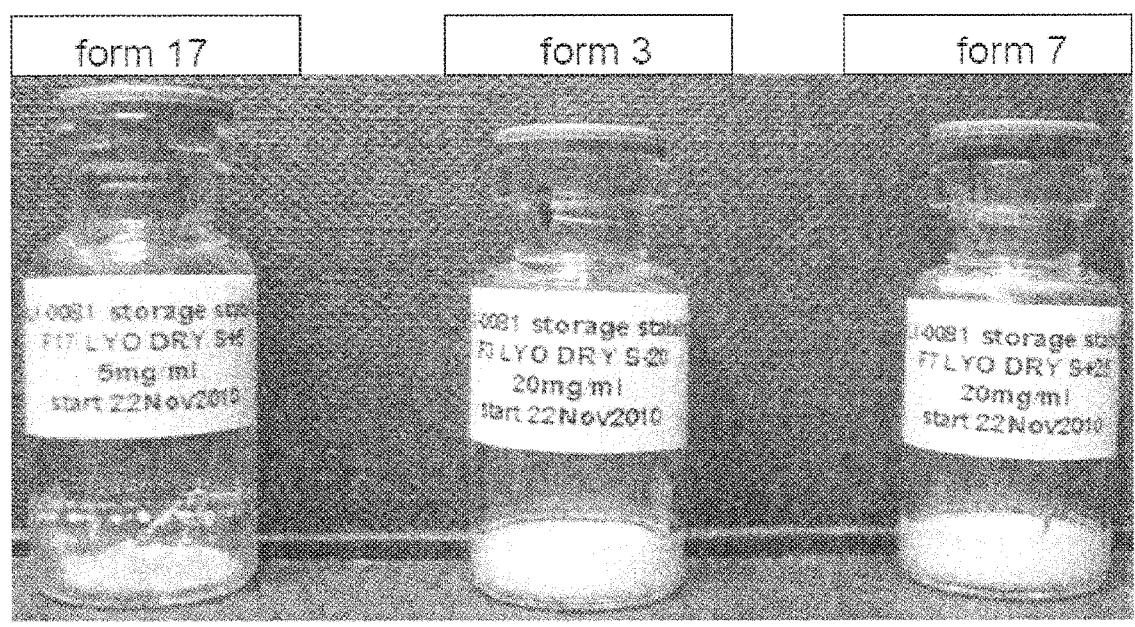
Figure 6B:
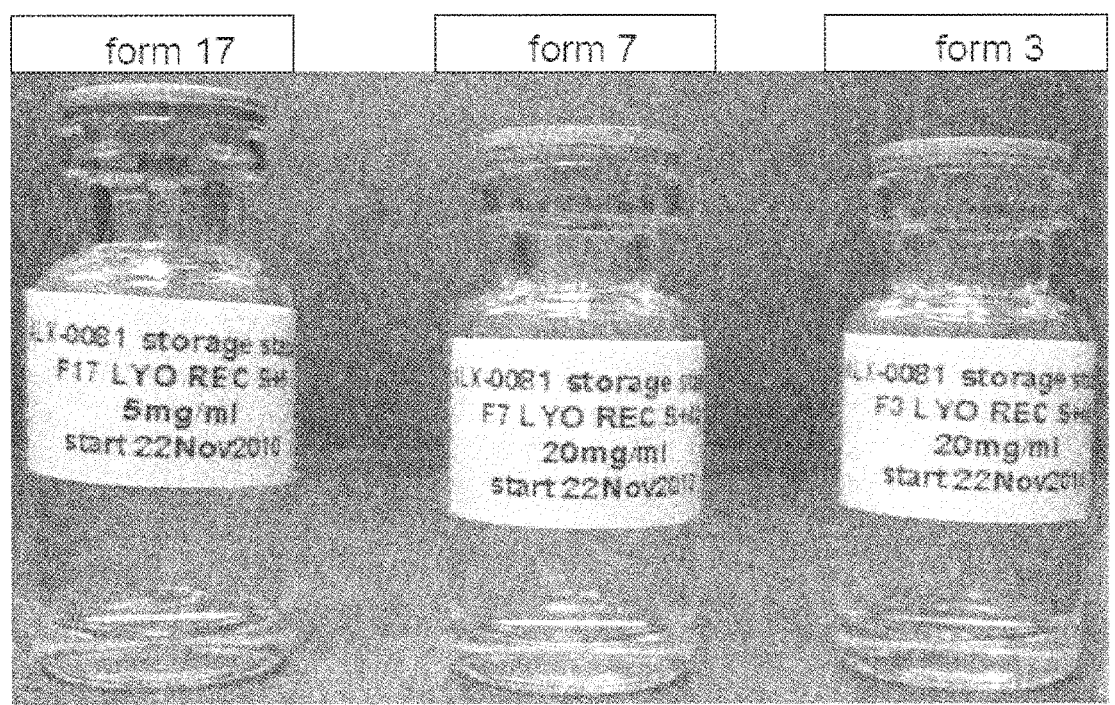

FIGS. 6A-6B Picture of lyophilized ALX-0081 formulations (form 3=citrate/sucrose pH 6.0; form 7=citrate/sucrose pH 6.5; form 17=D-PBS/glycine) before (FIG. 6A) and after reconstitution with Milli-Q water (FIG. 6B).

Figure 7:
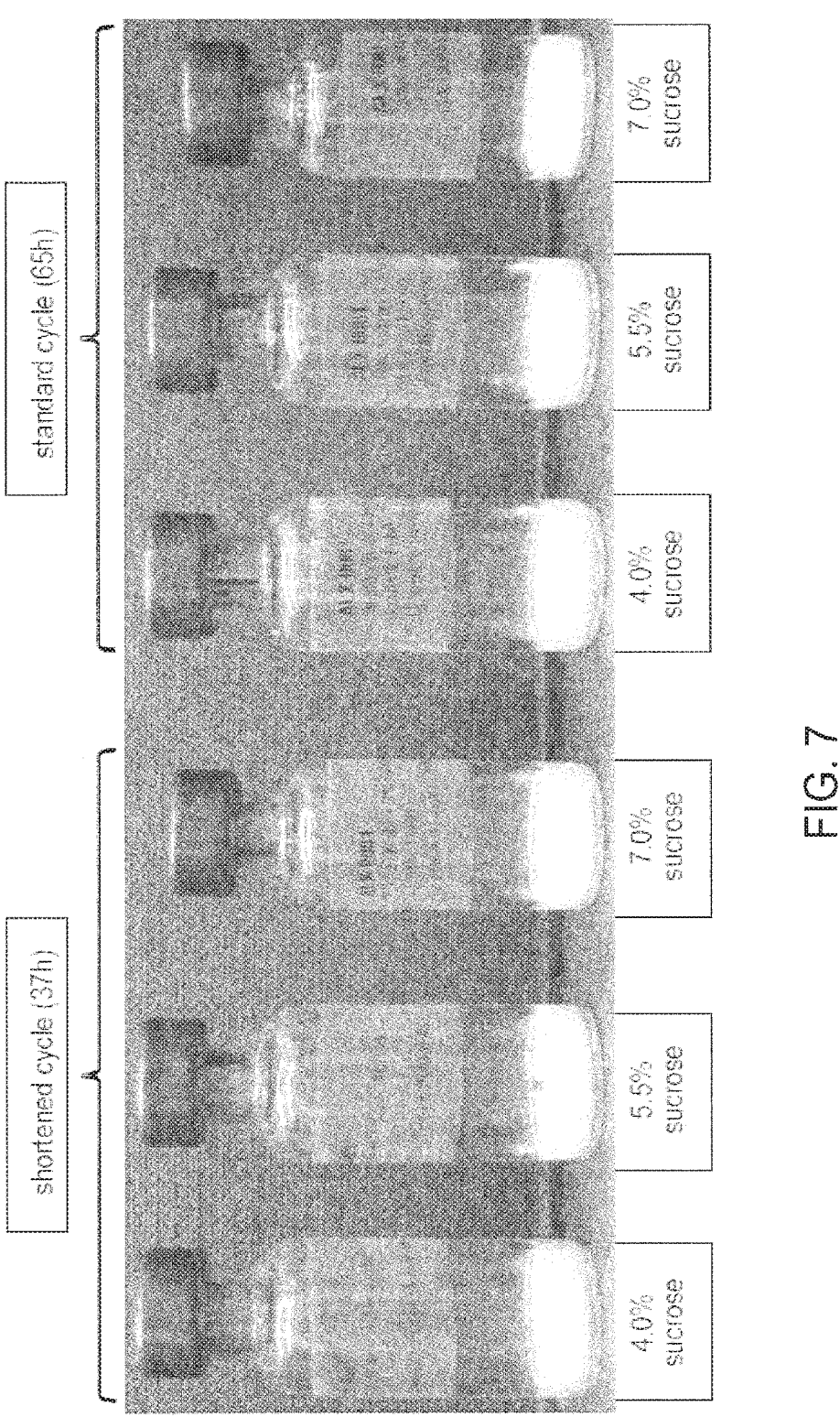

FIG. 7 Picture of lyophilized ALX-0081 citrate/sucrose 35 based formulations.

Figure 8A:
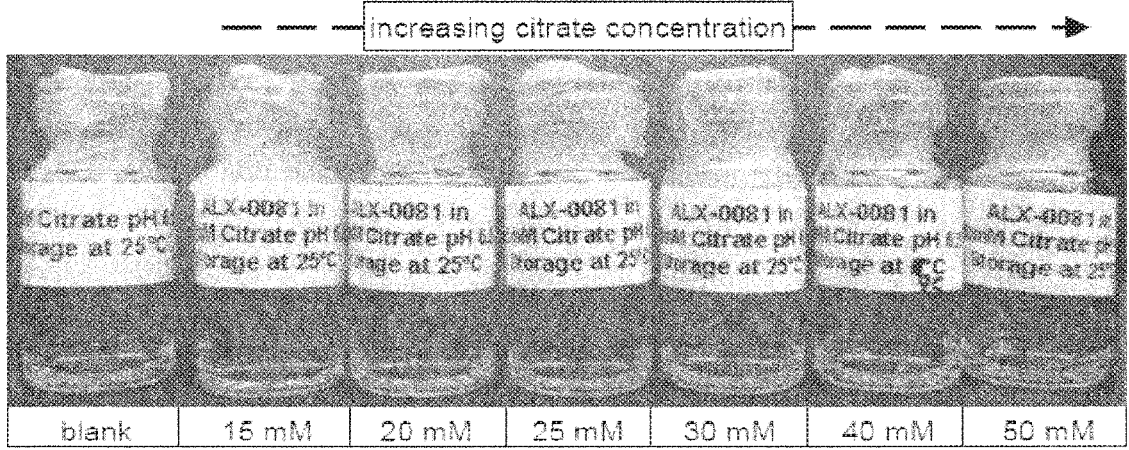
Figure 8B:
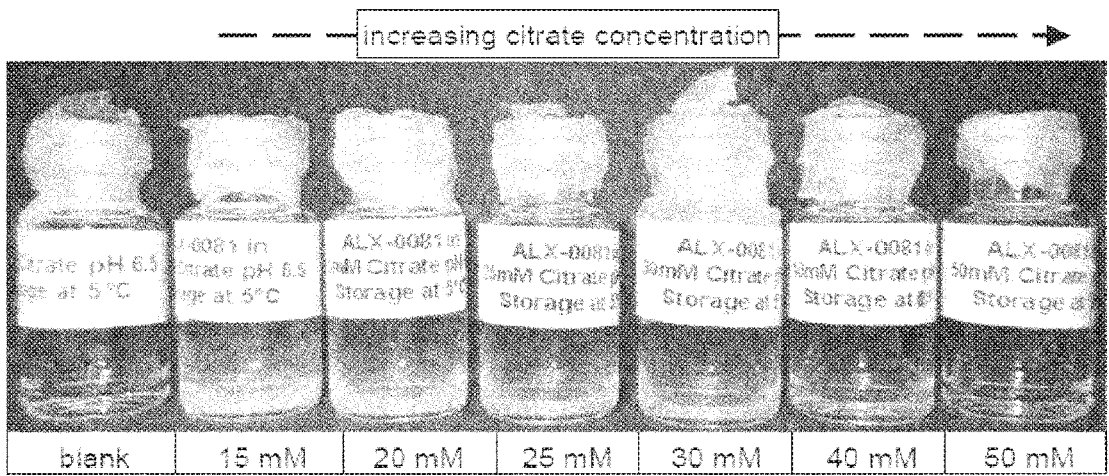

FIGS. 8A-8B Pictures of liquid ALX-0081 formulations at 28 mg/mL containing 15, 20, 25, 30, 40, and 50 mM citrate pH 6.5 after 4 days storage at +25° C. (FIG. 8A) or +5° C. (FIG. 8B). Blank citrate buffer (50 mM) is included 40 as reference.

Figure 9A:
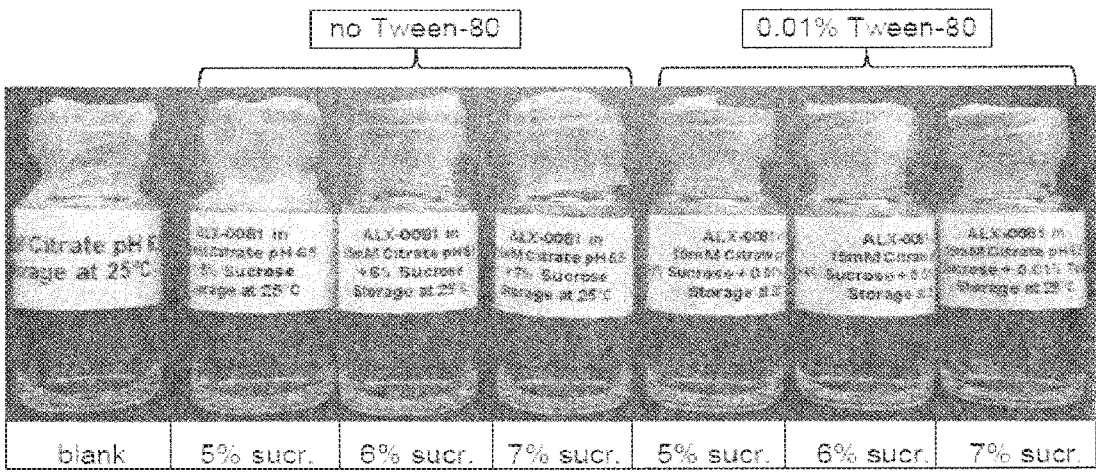
Figure 9B:
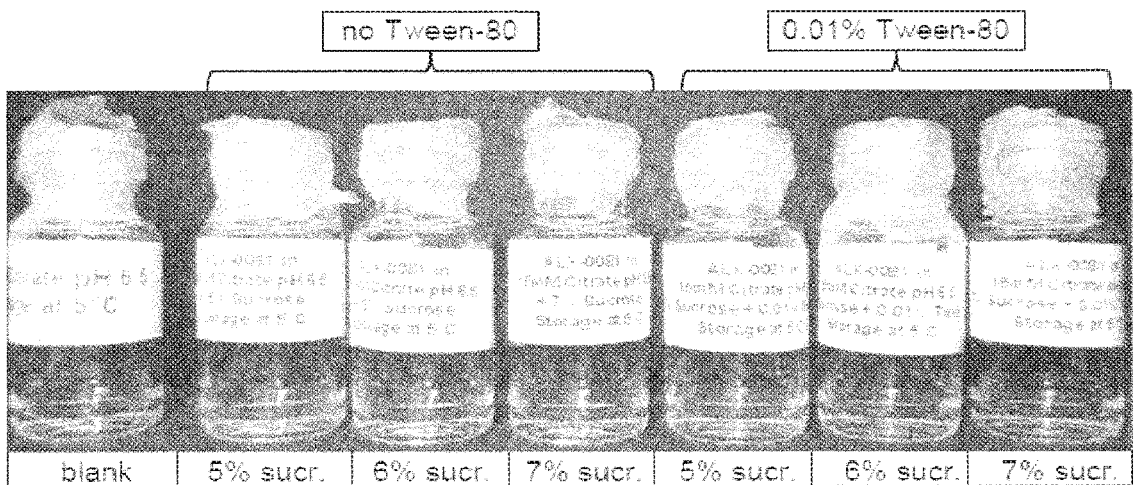

FIGS. 9A-9B Pictures of liquid ALX-0081 formulations at 20 mg/mL containing 15 mM citrate pH 6.5 and different amounts of sucrose and Tween-80 after 4 days storage at +25° C. (FIG. 9A) or +5° C. (FIG. 9B). Blank citrate buffer 45 (50 mM) is included as reference.

Figure 10:
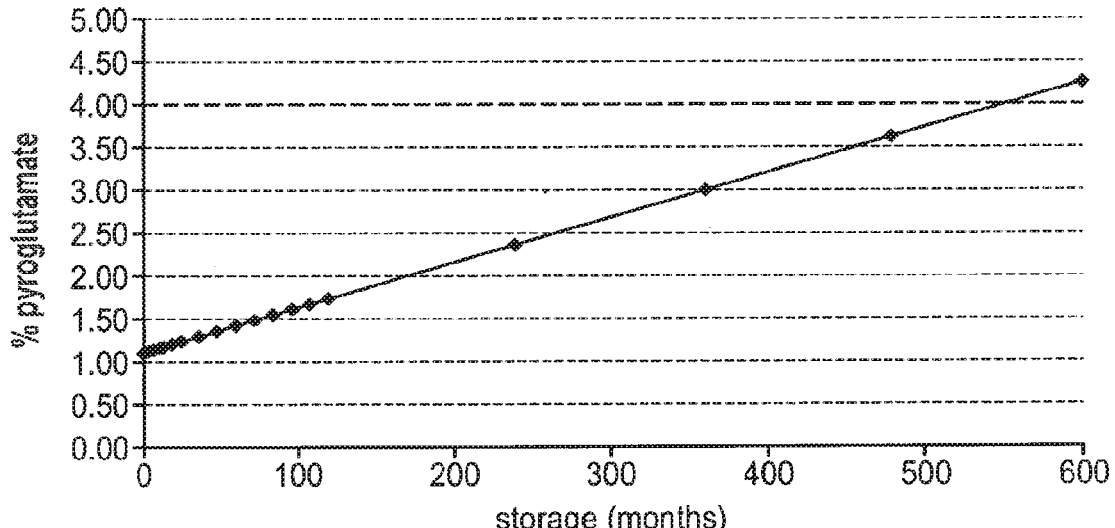

FIG. 10 Prediction of the percentage of pyroglutamate in lyophilized ALX-0081 drug product as function of time when stored at +5° C.

Figure 11:
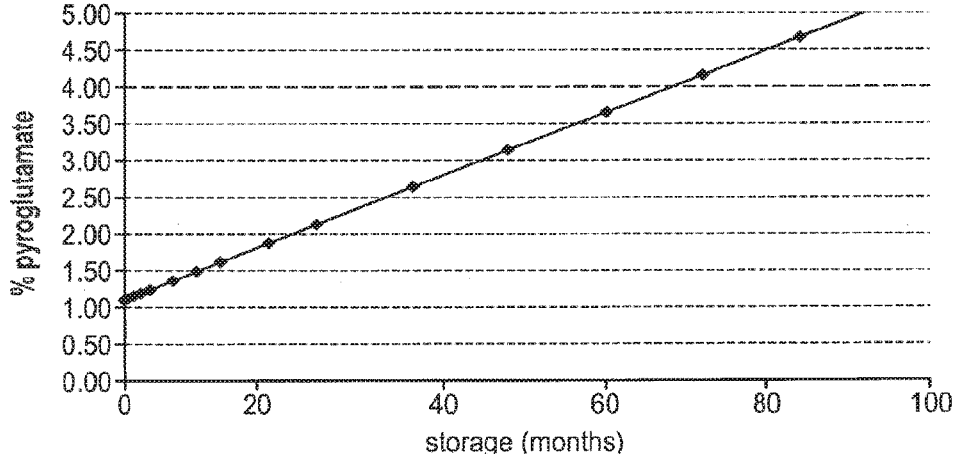

FIG. 11 Prediction of the percentage of pyroglutamate in 50 lyophilized ALX-0081 drug product as function of time when stored at +25° C.

DETAILED DESCRIPTION OF THE INVENTION

Unless indicated otherwise, all methods, steps, techniques and manipulations that are not specifically described in detail can be performed and have been performed in a manner known per se, as will be clear to the skilled person. 60 Reference is for example again made to the standard handbooks and the general background art mentioned herein and to the further references cited therein; as well as to for example the following reviews: Presta, Adv. Drug Deliv. Rev. 2006, 58 (5-6): 640-56; Levin and Weiss, Mol. Biosyst. 65 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

It has now surprisingly been found that vWF binders, and in particular ALX-0081 (SEQ ID NO: 1), can be administered in particular dosing regimens in humans. The vWF binders, and in particular ALX-0081, have been found to produce a pharmacodynamic effect, with a fast onset of action immediately at the end of dosing and maintains its efficacy for up to about 12-24 h. Additionally, vWF binders, and in particular ALX-0081 (SEQ ID NO: 1), have been found to be well tolerated and safe in healthy male volunteers. These results indicate that vWF binders and in particular ALX-0081 (SEQ ID NO: 1) are suitable for acute treatment in patients with stable angina undergoing elective percutaneous coronary intervention (hereinafter also "PCI") and treatment in patients with thrombotic thrombocytopenic purpura (hereinafter also "TTP").

Nevertheless, the current formulations of the vWF binders and in particular ALX-0081 (SEQ ID NO: 1) administered to human recipients were amenable to improvement.

The reformulation invention for the vWF binders, and in particular ALX-0081, described herein rendered a new citrate/sucrose based formulation with increased solubility (up to 80 mg/mL) and significantly improved liquid storage stability (e.g. less oxidation occurs when storing the new formulation to the original formulation in its liquid state). Also, in the lyophilized form, essentially no oxidation or asp-isomerisation could be detected after 12 months storage at +40° C. or even 24 months storage at +40° C. A residual formation of small amounts of pyroglutamate was still observed. Further optimization of the citrate and sucrose concentration resulted in a reduction of the moisture content of the lyophilized product, thereby minimizing the rate of residual pyroglutamate formation.

Accordingly the present invention provides stable liquid and lyophilized formulations of anti-vWF binders (e.g. ALX-0081) and uses thereof for treating or preventing vWF-related disorders.

Polypeptide(s) of the Invention

The vWF binders used in the present invention are typically proteins or polypeptides that bind to human von Willebrand Factor (vWF, SEQ ID NO: 20). Preferably, the vWF binders are proteins or polypeptides comprising or consisting of at least one immunoglobulin sequences, such as an immunoglobulin single variable domain (ISVD). Even more preferably, the vWF binders of the present invention are proteins or polypeptides comprising or consisting of SEQ ID NOs: 1-19, and most preferably SEQ ID NO: 1. The vWF binders may be used as adjunctive therapy for patients with ACS undergoing PCI or as treatment of thrombotic thrombocytopenic purpura (TTP). The terms "protein", "polypeptide" and "amino acid sequence" are used interchangeably herein. Thus, an amino acid sequence of the invention is a vWF binder.

Thus, for example, suitable vWF binders for use in the invention may include the compounds in Table A-1, e.g. SEQ ID NO: 1-19, or a compound having 80% or more, more preferably 85% or more, most preferred 90%, 95%, 96%, 97%, 98%, 99% or more, amino acid sequence identity to a compound in Table A-1 (see Definition section for "sequence identity").

Preferably the vWF binders for use in the invention are 12A02H1-like compounds. For the purposes of the present description a 12A02H1-like compound is a compound which comprises 12A02H1 (i.e. SEQ ID NO: 19) or a compound having 80% or more, more preferably 85% or more, most preferably 90%, 95%, 96%, 97%, 98%, 99% or more, amino acid sequence identity (as further defined herein) to 12A02H1 (SEQ ID NO: 19). A particularly preferred vWF binder is ALX-0081 (SEQ ID NO: 1).

All the vWF binders mentioned above are well known from the literature. This includes their manufacture (see in particular e.g. WO2006/122825 but also WO2004/062551). For example, ALX-0081 is prepared as described e.g. in WO2006/122825 or WO2009/115614.

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecule or antigen-binding protein are used interchangeably with immunoglobulin sequence, and include immunoglobulin single variable domains, such as Nanobodies®.

Embodiments of the invention relate to immunoglobulin sequences that are immunoglobulin single variable domains, such as light chain variable domain sequences (e.g. a $V_L$-sequence), or heavy chain variable domain sequences (e.g. a $V_H$-sequence); more specifically, heavy chain variable domain sequences that are derived from a conventional four-chain antibody or heavy chain variable domain sequences that are derived from a heavy chain antibody (e.g. a $V_{HH}$-sequence).

The term "immunoglobulin single variable domain" defines molecules wherein the antigen binding site is present on, and formed by, a single immunoglobulin domain or suitable fragments thereof. This sets immunoglobulin single variable domains apart from "conventional" immunoglobulins or their fragments, wherein two immunoglobulin domains, in particular two variable domains interact to form an antigen binding site. Typically, in conventional immunoglobulins, a heavy chain variable domain ($V_H$) and a light chain variable domain ($V_L$) interact to form an antigen binding site. In this case, the complementarity determining regions (CDRs) of both $V_H$ and $V_L$ will contribute to the antigen binding site, i.e. a total of 6 CDRs will be involved in antigen binding site formation.

In contrast, the antigen binding site of an immunoglobulin single variable domain is formed by a single $V_H$ or $V_L$ domain. Hence, the antigen binding site of an immunoglobulin single variable domain is formed by no more than three CDRs, e.g. one, two or three CDRs.

The term "immunoglobulin single variable domain" hence does not comprise conventional immunoglobulins or their fragments which require interaction of at least two variable domains for the formation of an antigen binding site. This is also the case for embodiments of the invention which "comprise" or "contain" an immunoglobulin single variable domain. In the context of the present invention, such embodiments exclude conventional immunoglobulins or their fragments. Thus, a composition that "comprises" or "contains" an immunoglobulin single variable domain may relate to e.g. constructs comprising more than one immunoglobulin single variable domain.

Alternatively, there may be further constituents other than the immunoglobulin single variable domains, e.g. auxiliary agents of different kinds, protein tags, colorants, dyes, etc. However, these terms do comprise fragments of conventional immunoglobulins wherein the antigen binding site is formed by a single variable domain.

According to the invention, the polypeptide of the invention, more specifically the immunoglobulin sequences, can consist of, or comprise one or more of the following: domain antibodies, or amino acid sequences that are suitable for use as domain antibodies, single domain antibodies, or amino acid sequences that are suitable for use as single domain antibodies, "dAbs", or amino acid sequences that are suitable for use as dAbs, or Nanobodies®, including but not limited to $V_{HH}$ sequences, such as humanized $V_{HH}$ sequences or camelized VH sequences, and preferably are Nanobodies®.

The present invention encompasses suitable fragments of immunoglobulin single variable domains. "Suitable fragments" of immunoglobulin single variable domains relate to polypeptides which contain fewer amino acids than a native immunoglobulin single variable domain, but still show antigen binding activity (which will then usually contain at least some of the amino acid residues that form at least one of the CDR's, as further described herein). Such immunoglobulin single variable domains and fragments most preferably comprise an immunoglobulin fold or are capable for forming, under suitable conditions, an immunoglobulin fold. More specifically, immunoglobulin single variable domains and their fragments are such that they are capable of binding to the target antigen. As such, the immunoglobulin single variable domain may for example comprise a light chain variable domain sequence (e.g. a $V_L$-sequence) or a suitable fragment thereof; or a heavy chain variable domain sequence (e.g. a $V_H$-sequence or $V_{HH}$-sequence) or a suitable fragment thereof; as long as it is capable of forming a single antigen binding unit (i.e. a functional antigen binding unit that essentially consists of the immunoglobulin single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain).

The immunoglobulin sequences of the invention are preferably in essentially isolated form. The immunoglobulin sequences of the invention may also form part of a protein or polypeptide of the invention (as defined herein), which may comprise or essentially consist of one or more amino acid sequences of the invention and which may optionally further comprise one or more further amino acid sequences (all optionally linked via one or more suitable linkers). For example, and without limitation, the one or more amino acid sequences of the invention may be used as a binding unit in such a protein or polypeptide, which may optionally contain one or more further amino acid sequences that can serve as a binding unit, so as to provide a monovalent, multivalent or multispecific polypeptide of the invention, respectively, all as described herein. Such a protein or polypeptide may also be in essentially isolated form.

The invention relates to immunoglobulin sequences of different origin, comprising mouse, rat, rabbit, donkey, human and camelid immunoglobulin sequences. The invention also includes fully human, humanized or chimeric immunoglobulin sequences. For example, the invention comprises camelid immunoglobulin sequences and humanized camelid immunoglobulin sequences, or camelized domain antibodies, e.g. camelized dAb as described by Ward et al (see for example WO 94/04678 and Davies and Riechmann (1994 and 1996)). Moreover, the invention comprises fused immunoglobulin sequences, e.g. forming a multivalent and/or multispecific construct (for multivalent and multispecific polypeptides containing one or more $V_{HH}$ domains and their preparation, reference is also made to Conrath et al., J. Biol. Chem., Vol. 276, 7346-7350, 2001, as well as to for example WO96/34103 and WO99/23221), and immunoglobulin sequences comprising tags or other functional moieties, e.g. toxins, labels, radiochemicals, etc., which are derivable from the immunoglobulin sequences of the present invention. Immunoglobulin single variable domains have also been described in sharks (also referred to as "IgNARs", as described e.g. in WO03/014161 or Streltsov, 2005).

In a particular embodiment, the immunoglobulin single variable domains of the invention are Nanobodies®, in particular camelid $V_{HH}$ domains, humanized $V_{HH}$ domains or camelized $V_H$ domains. The skilled person is well acquainted with humanization of $V_{HH}$ and/or camelizing $V_H$ domains.

The amino acid sequence and structure of an immunoglobulin sequence, in particular a Nanobody® can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

The total number of amino acid residues in a Nanobody® can be in the region of 110-120, is preferably 112-115, and is most preferably 113. It should however be noted that parts, fragments, analogs or derivatives (as further described herein) of a Nanobody® are not particularly limited as to their length and/or size, as long as such parts, fragments, analogs or derivatives meet the further requirements outlined herein and are also preferably suitable for the purposes described herein.

Thus, generally, immunoglobulin single variable domains will be amino acid sequences that consist of, or essentially consist of 4 framework regions (FR1 to FR4 respectively) and 3 complementarity determining regions (CDR1 to CDR3 respectively). "Essentially consist" in this context means that additional elements such as e.g. tags used for purification or labelling may be present, but such additional elements are small as compared to the immunoglobulin single variable domain per se, and do not interfere with the antigen binding activity of the immunoglobulin single variable domain.

As used herein, the term "immunoglobulin sequences" or "immunoglobulin single variable domains" refers to both the nucleic acid sequences coding for the polypeptide, and the polypeptide per se. Any more limiting meaning will be apparent from the specific context.

In particular, the amino acid sequence of the invention may be a Nanobody® or a suitable fragment thereof. For a further description of $V_{HH}$'s and Nanobodies, reference is made to the review article by Muyldermans in Reviews in Molecular Biotechnology 74(2001), 277-302; as well as to the following patent applications, which are mentioned as general background art: WO94/04678, WO95/04079 and WO96/34103 of the Vrije Universiteit Brussel; WO94/25591, WO99/37681, WO00/40968, WO00/43507, WO00/

65057, WO01/40310, WO01/44301, EP1134231 and WO02/48193 of Unilever; WO97/49805, WO01/21817, WO03/035694, WO03/054016 and WO03/055527 of the Vlaams Instituut voor Biotechnologie (VIB); WO03/050531 of Algonomics N. V. and Ablynx N. V.; WO 01/90190 by the National Research Council of Canada; WO03/025020 (=EP1433793) by the Institute of Antibodies; as well as WO04/041867, WO04/041862, WO04/041865, WO04/041863, WO04/062551, WO05/044858, WO06/40153, WO06/079372, WO06/122786, WO06/122787 and WO06/122825, by Ablynx N. V. and the further published patent applications by Ablynx N. V. Reference is also made to the further prior art mentioned in these applications, and in particular to the list of references mentioned on pages 41-43 of the International application WO06/040153, of which the list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO07/104529.

The immunoglobulin single variable domains provided by the invention are preferably in isolated form or essentially isolated form. The immunoglobulin sequences of the invention may also form part of a protein or polypeptide of the invention, which may comprise or essentially consist of one or more immunoglobulin single variable domains and which may optionally further comprise one or more further amino acid sequences (all optionally linked via one or more suitable linkers). For example, and without limitation, the one or more immunoglobulin single variable domains may be used as a binding unit in such a protein or polypeptide, which may optionally contain one or more further amino acid sequences that can serve as a binding unit, so as to provide a monovalent, multivalent or multispecific polypeptide of the invention, respectively, all as described herein. Such a protein or polypeptide may also be in isolated or essentially isolated form. Thus, according to the invention, immunoglobulin single variable domains comprise constructs comprising two or more antigen binding units in the form of single domains, as outlined above. For example, two (or more) immunoglobulin single variable domains with the same or different antigen specificity can be linked to form e.g. a bivalent, trivalent or multivalent construct. By combining immunoglobulin single variable domains of two or more specificities, bispecific, trispecific etc. constructs can be formed. For example, a polypeptide according to the invention may comprise two immunoglobulin single variable domains directed against target A, and one immunoglobulin single variable domain against target B, making it bivalent for A and monovalent for B. Such constructs and modifications thereof, which the skilled person can readily envisage, are all encompassed by the present invention. In particular embodiments, the invention relates to bi-paratopic constructs comprising at least two immunoglobulin single variable domains directed to different epitopes within the same target antigen.

All these molecules are also referred to as "polypeptide of the invention", which is synonymous with "immunoglobulin sequences" or "immunoglobulin single variable domains" of the invention.

In addition, the term "sequence" as used herein (for example in terms like "immunoglobulin sequence", "antibody sequence", "variable domain sequence", "$V_{HH}$-sequence" or "protein sequence"), should generally be understood to include both the relevant amino acid sequence as well as nucleic acid sequences or nucleotide sequences encoding the same, unless the context requires a more limited interpretation.

According to one non-limiting embodiment of the invention, the immunoglobulin sequences, Nanobody® or polypeptide of the invention is glycosylated. According to another non-limiting embodiment of the invention, the immunoglobulin sequences, Nanobody® or polypeptide of the invention is non-glycosylated.

"Binding" to an Antigen

The invention relates to immunoglobulin sequences that can bind to and/or have affinity for an antigen as defined herein, e.g. von Willebrand Factor. In the context of the present invention, "binding to and/or having affinity for" a certain antigen has the usual meaning in the art as understood e.g. in the context of antibodies and their respective antigens.

In particular embodiments of the invention, the term "binds to and/or having affinity for" means that the immunoglobulin sequence specifically interacts with an antigen, and is used interchangeably with immunoglobulin sequences "against" the said antigen.

The term "specificity" refers to the number of different types of antigens or antigenic determinants to which a particular immunoglobulin sequence, antigen-binding molecule or antigen-binding protein (such as an immunoglobulin single variable domain, a Nanobody® or a polypeptide of the invention) can bind. The specificity of an antigen-binding protein can be determined based on affinity and/or avidity. The affinity, represented by the equilibrium constant for the dissociation of an antigen with an antigen-binding protein (KD), is a measure for the binding strength between an antigenic determinant and an antigen-binding site on the antigen-binding protein: the lesser the value of the KD, the stronger the binding strength between an antigenic determinant and the antigen-binding molecule (alternatively, the affinity can also be expressed as the affinity constant (KA), which is 1/KD). As will be clear to the skilled person (for example on the basis of the further disclosure herein), affinity can be determined in a manner known per se, depending on the specific antigen of interest. Avidity is the measure of the strength of binding between an antigen-binding molecule (such as an immunoglobulin single variable domain, a Nanobody® or polypeptide of the invention) and the pertinent antigen. Avidity is related to both the affinity between an antigenic determinant and its antigen binding site on the antigen-binding molecule and the number of pertinent binding sites present on the antigen-binding molecule.

Typically, immunoglobulin sequences of the present invention (such as the amino acid sequences, immunoglobulin single variable domains, Nanobodies® and/or polypeptides of the invention) will bind to their antigen with a dissociation constant (KD) of $10^{-5}$ to $10^{-12}$ moles/liter or less, and preferably $10^{-7}$ to $10^{-12}$ moles/liter or less or more preferably $10^{-8}$ to $10^{-12}$ moles/liter (i.e. with an association constant (KA) of $10^5$ to $10^{12}$ liter/moles or more, and preferably $10^7$ to $10^{12}$ liter/moles or more and more preferably $10^8$ to $10^{12}$ liter/moles), and/or bind to their antigen as defined herein with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$; and/or bind to their antigen as defined herein with a $k_{off}$ rate between 1 $s^{-1}$ (t1/2=0.69 s) and $10^{-6}$ $s^{-1}$ (providing a near irreversible complex with a t1/2 of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Any KD value greater than $10^{-4}$ M (or any KA value lower than $10^4$ $M^{-1}$) is generally considered to indicate non-specific binding.

Preferably, a monovalent immunoglobulin sequence of the invention will bind to the desired antigen with an affinity less than 500 nM, preferably less than 200 nM, more preferably less than 10 nM, such as less than 500 pM.

Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant (KD) may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more than $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant (KA), by means of the relationship [KD=1/KA].

The affinity denotes the strength or stability of a molecular interaction. The affinity is commonly given as by the KD, or dissociation constant, which has units of mol/liter (or M). The affinity can also be expressed as an association constant, KA, which equals 1/KD and has units of (mol/liter)$^{-1}$ (or $M^{-1}$). In the present specification, the stability of the interaction between two molecules (such as an amino acid sequence, immunoglobulin sequence, immunoglobulin single variable domain, Nanobody® or polypeptide of the invention and its intended target) will mainly be expressed in terms of the KD value of their interaction; it being clear to the skilled person that in view of the relation KA=1/KD, specifying the strength of molecular interaction by its KD value can also be used to calculate the corresponding KA value. The KD-value characterizes the strength of a molecular interaction also in a thermodynamic sense as it is related to the free energy (DG) of binding by the well-known relation DG=RT·ln(KD) (equivalently DG=−RT·ln(KA)), where R equals the gas constant, T equals the absolute temperature and ln denotes the natural logarithm.

The KD for biological interactions, such as the binding of the immunoglobulin sequences of the invention to vWF as defined herein, which are considered meaningful (e.g. specific) are typically in the range of $10^{-10}$ M (0.1 nM) to $10^{-5}$ M (10000 nM). The stronger an interaction is, the lower its KD is.

The KD can also be expressed as the ratio of the dissociation rate constant of a complex, denoted as $k_{off}$, to the rate of its association, denoted $k_{on}$ (so that KD=$k_{off}$/$k_{on}$ and $KA=k_{on}/k_{off}$). The off-rate $k_{off}$ has units $s^{-1}$ (where s is the SI unit notation of second). The on-rate kon has units $M^{-1}s^{-1}$.

As regards immunoglobulin sequences of the invention, the on-rate may vary between $10^2$ $M^{-1}s^{-1}$ to about $10^7$ $M^{-1}s^{-1}$, approaching the diffusion-limited association rate constant for bimolecular interactions. The off-rate is related to the half-life of a given molecular interaction by the relation $t1/2=\ln(2)/k_{off}$. The off-rate of immunoglobulin sequences of the invention may vary between $10^{-6}$ $s^{-1}$ (near irreversible complex with a t1/2 of multiple days) to 1 $s^{-1}$ (t1/2=0.69 s).

The affinity of a molecular interaction between two molecules can be measured via different techniques known per se, such as the well-known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding kon, koff measurements and hence KD (or KA) values. This can for example be performed using the well-known Biacore instruments.

It will also be clear to the skilled person that the measured KD may correspond to the apparent KD if the measuring process somehow influences the intrinsic binding affinity of the implied molecules for example by artefacts related to the coating on the biosensor of one molecule. Also, an apparent KD may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of KD may be quite labour-intensive and as consequence, often apparent KD values are determined to assess the binding strength of two molecules. It should be noted that as long as all measurements are made in a consistent way (e.g. keeping the assay conditions unchanged) apparent KD measurements can be used as an approximation of the true KD and hence in the present document KD and apparent KD should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an IC50 value is obtained corresponding to the concentration of A at which the signal measured for C in absence of A is halved. Provided KD ref, the KD of the reference molecule, is known, as well as the total concentration cref of the reference molecule, the apparent KD for the interaction A-B can be obtained from following formula: KD=IC50/(1+cref/KD ref). Note that if cref≪KD ref, KD≈IC50. Provided the measurement of the IC50 is performed in a consistent way (e.g. keeping cref fixed) for the binders that are compared, the strength or stability of a molecular interaction can be assessed by the IC50 and this measurement is judged as equivalent to KD or to apparent KD throughout this text.

Target Antigen

The immunoglobulin single variable domains of the present invention bind to and/or have affinity for vWF. In the context of the present invention, "vWF" includes, but is not limited, to cynomolgus, baboon, pig, guinea pig, mouse, and/or human vWF and most preferred human vWF, i.e. SEQ ID NO: 20 or Gen Bank entry: NP_000543.

Specific Embodiments of Immunoglobulin Sequences

The present invention relates to immunoglobulin single variable domains described in, or obtainable by, the methods as disclosed in WO2004/015425, WO2004/062551, WO2006/074947, WO2006/122825, WO2009/115614, or WO2011/067160, all in the name of the present applicant.

The invention also encompasses optimized variants of these amino acid sequences. Generally, an "optimized variant" of an amino acid sequence according to the invention is a variant that comprises one or more beneficial substitutions such as a substitutions increasing i) the degree of "humanization", ii) the chemical stability, and/or iii) the level of expression; while the potency (measured e.g. by the potency assay as described in the experimental part of WO2006/122825 remains comparable (i.e. within a 10% deviation) to the wild type 12A02 (as defined in WO2006/122825) or comparable to the variant 12A02H1 (SEQ ID NO: 19), also as defined in WO2006/122825. Preferably, compared to the wild-type sequence of 12A02, an amino acid sequence of the invention contains at least one such substitution, and preferably at least two such substitutions, and preferably at least three humanizing substitutions and preferably at least 10 such humanizing substitutions.

In a particular aspect, the amino acid sequences of the invention contain a total of between 1 and 15, preferably between 2 and 14, such as between 9 and 13, e.g. 10, 11 or 12 amino acid substitutions compared to the wild-type sequence 12A02. As mentioned, these differences preferably at least comprise one and preferably at least two, such as three, four or five or ten humanizing substitutions, and may optionally comprise one or more further substitutions (such as any one of, or any suitable combination of any two or more of, the further substitutions (a) to (c) as mentioned herein). Again, based on the disclosure herein and optionally after a limited degree of trial and error, the skilled person will be able to select (a suitable combination of) one or more such suitable humanizing and/or further substitutions.

The present invention encompasses polypeptide sequences that are highly similar to any of the specific examples provided herein, or any of the specific examples defined by reference above. Highly similar means an amino acid identity of at least 90%, e.g. 95, 97, 98 or 99%. The highly similar polypeptide sequences will have the same function as the sequence they are derived from, i.e. they will bind to vWF, more specifically bind to and inhibit interaction between vWF and platelets.

In a particular embodiment, the invention relates to sequences highly similar to any one of SEQ ID NOs: 1-19, in particular SEQ ID NO: 1. However, for each variant sequence stability in the formulation as defined herein has to be evaluated, such that the invention in particular refers to variants or highly similar sequences which are stable in the formulations as defined herein.

Methods to generate polypeptide sequences of the invention are widely known and include e.g. recombinant expression or synthesis. The skilled person is well acquainted with suitable expression technology, e.g. suitable recombinant vectors and host cells, e.g. bacterial or yeast host cells. The skilled person is also well acquainted with suitable purification techniques and protocols.

Formulations of the Invention

The present invention provides formulations of polypeptides directed against vWF, e.g. immunoglobulin single variable domains (ISVDs) or polypeptides comprising at least one immunoglobulin single variable domain, which are stable, and preferably suitable for pharmaceutical uses, comprising the preparation of medicaments.

A formulation of a vWF binder, e.g., an ISVD, includes an ISVD, a compound that can serve as a cryoprotectant and/or lyoprotectant, and a buffer. The pH of the formulation is generally pH 5-7.5. In some embodiments, a formulation is stored as a liquid. In other embodiments, a formulation is prepared as a liquid and then is dried, e.g., by lyophilization or spray-drying, prior to storage. A dried formulation (i.e. the lyophilisate) can be used as a dry compound, e.g., as an aerosol or powder, or reconstituted to its original or another concentration, e.g., using water, a buffer, or other appropriate liquid (diluent).

The vWF binder purification process is designed to permit transfer of the vWF binder into a formulation suitable for long-term storage, e.g. as a frozen liquid and/or subsequently for freeze-drying (e.g., using a citrate/sucrose formulation). The formulation is lyophilized with the protein, e.g. vWF binder at a specific concentration. The lyophilized formulation can then be reconstituted as needed with a suitable diluent (e.g., water) to resolubilize the original formulation components to a desired concentration, generally the same or higher concentration compared to the concentration prior to lyophilization. The lyophilized formulation may be reconstituted to produce a formulation that has a concentration that differs from the original concentration (i.e., before lyophilization), depending upon the amount of diluent added to the lyophilisate relative to the volume of liquid that was originally freeze-dried. Suitable formulations can be identified by assaying one or more parameters of vWF binder integrity. The assayed parameters are generally the percentage of High Molecular Weight (HMW) species or the percentage of Low Molecular Weight (LMW) species by Size Exclusion HPLC (SE-HPLC).

Accordingly, the present invention provides formulations characterized by a suitable degree of purity and at suitable concentrations as required e.g. for pharmaceutical purposes. The formulations provide the polypeptides, e.g. immunoglobulin single variable domains or polypeptides comprising at least one immunoglobulin single variable domain as defined herein in a stable form over a large range of concentrations, and a large range of storage conditions, e.g. temperatures, including stressed conditions such as elevated temperatures (e.g. +25° C. or higher), lyophilization, shaking or other forms of physical stress.

The formulation comprises an aqueous carrier. The aqueous carrier is in particular a buffer.

The invention, however, also encompasses products obtainable by further processing of a liquid formulation, such as a frozen, lyophilized or spray-dried product. Upon reconstitution, these solid products can become liquid formulations as described herein (but are not limited thereto). In its broadest sense, therefore, the term "formulation" encompasses both liquid and solid formulations. However, solid formulations are understood as derivable from the liquid formulations (e.g. by freezing, freeze-drying or spray-drying), and hence have various characteristics that are defined by the features specified for liquid formulations herein. The invention does not exclude reconstitution that leads to a composition that deviates from the original composition before e.g. freeze- or spray drying.

The formulations of the invention comprise at least one vWF binder, in particular immunoglobulin single variable domains or a polypeptide comprising at least one immunoglobulin single variable domain as defined herein. In particular embodiments, the formulation comprises one or more polypeptides selected from SEQ ID NOs: 1-19, preferably SEQ ID NO: 1. The polypeptides may in addition be half-life extended e.g. by incorporating a serum-albumin binding peptide or binding domain, which may be any suitable serum-albumin binding peptide or binding domain capable of increasing the half-life of the construct (compared to the same construct without the serum-albumin binding peptide or binding domain), and may in particular be serum albumin binding peptides as described in WO2008/068280 by applicant (and in particular WO2009/127691 and WO2011/095545, both by applicant), or a serum-albumin binding immunoglobulin single variable domain (such as a serum-albumin binding Nanobody; for example Alb-1 or a humanized version of Alb-1 such as Alb-8, for which reference is for example made to WO06/122787). Alternative means for extending half-life which are also encompassed by the present invention include e.g. pegylation (PEG) as widely known in the art, including site specific or random pegylation, preferably site specific pegylation. PEG can be used with a molecular weight above 5000, e.g. between 10.000 and 200.000, preferably in the range between 20.000 and 100.000. In any aspect of half-life extension, it is envisaged that the activity of the polypeptide as defined herein is not compromised, e.g. retains at least 75%, 80%, 85%, 90% or 95% of the activity of the same polypeptide without half-life extension. Activity can relate to e.g. binding to the target antigen, and/or potency in a bioassay. The skilled person will also ascertain that the chosen half-life extension technology is suitable in that it does not increase, or even decreases immunogenicity.

Buffer

The formulation of the invention comprises a buffer selected from at least one of citrate or phosphate buffer, preferably a citrate buffer. In a particular embodiment, the citrate buffer is prepared using citric acid monohydrate and tri-sodium citrate dehydrate, e.g. 0.2154 g/L citric acid monohydrate and 5.5805 g/L tri-sodium citrate dehydrate. As determined by measuring melting temperatures in a non-limiting example, these buffers enhance the stability of the vWF binders, compared to other tested buffers.

The formulation according to the invention comprises a citrate buffer at a concentration in the range of 5-200 mM, e.g. 5, 7.5, 10, 15, 20, 25, 30, 40, 50, 60, 70, 80, 90, 100, 110, 120, 130, 140, 150, 160, 170, 180, 190 or 200 mM, preferably 5-100 mM, more preferably 7.5-80 mM, even more preferably 10-50, e.g. 10, 15, 20, 25 or 30 mM, and most preferably 20 mM, wherein each value is understood to optionally encompass a range of ±5 mM. The formulation according to the invention may comprise a phosphate buffer at a concentration in the range of 5-200 mM, e.g. 5, 7.5, 10, 15, 20, 25, 30, 40, 50, 60, 70, 80, 90, 100, 110, 120, 130, 140, 150, 160, 170, 180, 190 or 200 mM, preferably 5-80 mM, more preferably 7.5-60 mM, even more preferably 10-40, e.g. 10, 15, 20, 25 or 30 mM, and most preferably 10 mM, wherein each value is understood to optionally encompass a range of ±5 mM. It will be understood that a lower concentration of the buffer has an effect on the final osmolality, and correspondingly on the additional solutes that may have to be added.

The pH of the formulation of the invention is in the range 5.0 to 7.5, wherein each value is understood to encompass a range of ±0.2. Specific examples of preferred pH values for formulations of the invention can be selected from the non-limiting list comprising pH of 5.0, 5.5, 5.8, 6.0, 6.2, 6.5, 6.7, 7.0, 7.1, 7.2 or 7.5, preferably 6.0 to 7.0, more preferably 6.1, 6.2, 6.3, 6.4, 6.5, 6.6, 6.7, 6.8 or 6.9, e.g. 6.5, wherein each value is understood to optionally encompass a range of ±0.2.

Unexpectedly, the citrate and phosphate buffers have overlapping pH ranges with e.g. histidine and Tris-HCl buffers, yet favour stability.

The most advantageous pH will depend on the buffer comprised in the formulation. Hence, the invention relates particularly to a formulation comprising a phosphate buffer, which preferably has a pH in the range of 6.5 to 7.5, preferably 6.9, 7.0, 7.1, e.g. 7.1.

It was shown that a formulation comprising a citrate buffer was outstandingly suitable for storage and use. However, in contrast to conventional wisdom, liquid formulations comprising a citrate buffer were most stable at a pH of about 6.0, while lyophilized formulations comprising a citrate buffer were most stable at a pH of about 6.5. Hence, the present invention relates to a formulation comprising a citrate buffer, which preferably has a pH between 6.0 and 7.0, more preferably 6.1, 6.2, 6.3, 6.4, 6.5, 6.6, 6.7, 6.8 or 6.9, e.g. 6.5, wherein each value is understood to optionally encompass a range of ±0.2.

Concentration

The formulations of the invention comprise the vWF binders as defined herein, in particular the immunoglobulin single variable domains or polypeptides comprising at least one immunoglobulin single variable domain at a concentration that is suitable for clinical purposes, which includes concentrations used in stock solutions for dilution prior to use on the patient. Apart from improved stabilization, the formulations of the invention enable higher concentrations of the vWF binders, e.g. ISVDs or polypeptides. In particular, the formulations of the invention remained physically stable, i.e. the absence of turbidity and/or small particle formation, as confirmed by visual inspection, microscopy, SE-HPLC and DLS. Storage at elevated temperatures for prolonged times and repeated freeze-thaw cycles did apparently not affect the physical stability of the vWF binders in these formulations.

Typical concentrations of the active agent, e.g. vWF binders or the polypeptides of the invention, in formulations of the invention comprise the non-limiting examples of concentrations in the range of 0.1 to 80 mg/mL, preferably 1-70 mg/mL, 5-60 mg/mL, 7.5-50 mg/mL, or 10-40 mg/mL, such as 5, 7.5, 10, 12.5, 15, 17.5, 20, 25, 30, 35, 40, 45, 50 or 60 mg/mL, preferably 12.5 mg/mL or 10 mg/mL, wherein each value is understood to optionally encompass a range of ±20% (e.g. a value of 10 optionally encompasses a range of 8 to 12 mg/mL).

Excipients

The formulations according to the invention may also optionally comprise one or more excipients. The term "excipient" as used herein refers to an inert substance which is commonly used as a diluent, vehicle, preservative, lyoprotectant, binder or stabilizing agent for compounds which impart a beneficial physical property to a formulation. The skilled person is familiar with excipients suitable for pharmaceutical purposes, which may have particular functions in the formulation, such as lyoprotection, stabilization, preservation, etc. Commonly used stabilizers and preservatives are well known to the skilled person (see e.g. WO2010/077422). Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat. In advantageous embodiments, the excipient may be one or more selected from the list consisting of NaCl, trehalose, sucrose, mannitol or glycine.

In appreciating the invention, the skilled person can readily determine suitable concentrations of the excipients to be added to the formulations. In exemplary embodiments, NaCl has a concentration in the range of 10-500 mM, such as 25, 30, 40, 50, 60, 70, 100, 150, 250 or 500 mM, preferably 50-150 mM, e.g. 75 or 140 mM, wherein each value is understood to optionally encompass a range of ±5 mM; and/or mannitol has a concentration of 1-10%, preferably 2-4%, e.g. 2, 3 or 4% (w/w), wherein each value is understood to optionally encompass a range of ±0.5%; and/or sucrose has a concentration of 1-15%, preferably 2-12% or 4-10%, e.g. 4, 5, 6, 7, 8 or 9% (w/w), and most preferably 7%, wherein each value is understood to optionally encompass a range of ±0.5%; and/or glycine has a concentration in the range of 10-500 mM, such as 25, 30, 40, 50, 60, 70, 75, 100, 150, 250 or 500 mM, preferably 50-400 mM, 75-300 mM, 100-250 mM, e.g. 140 or 200 mM, wherein each value is understood to optionally encompass a range of ±5 mM; and/or trehalose has a concentration in the range of 10-500 mM, such as 25, 30, 40, 50, 60, 70, 75, 100, 150, 250 or 500 mM, preferably 100-300 mM, 150-280 mM, e.g. 160 mM or 260 mM, wherein each value is understood to optionally encompass a range of ±5 mM.

In a preferred embodiment, the formulations according to any aspect of the invention are isotonic in relation to human blood. Isotonic solutions possess the same osmotic pressure as blood plasma, and so can be intravenously infused into a subject without changing the osmotic pressure of the subject's blood plasma. Tonicity can be expressed in terms of osmolality, which can be a theoretical osmolality, or preferably an experimentally determined osmolality. Typically, osmolality will be in the range of 290±60 mOsm/kg, preferably 290±20 mOsm/kg.

Thus, in the selection of excipients (if any) the skilled person will consider buffer concentration and the concentrations of the one or more excipients and preferably arrive at a formulation with an osmolality in the ranges as specified above. The skilled person is familiar with calculations to estimate osmolality (see e.g. WO2010/077422). If required, the skilled person can also further include a compound to adjust the osmolality of the formulation. Exemplary compounds include, but are not limited to the above mentioned excipients, and/or one or more of sorbitol, methionine, dextrose, inositol, arginine, or arginine hydrochloride.

It has been shown that a formulation comprising sucrose was particularly suited for maintaining the physical stability, during e.g. storage and freeze-thawing, of the polypeptides. Accordingly, the present invention relates to formulations comprising about 5-9% more preferably 6-8% and even more preferably 7% sucrose, wherein each value is understood to optionally encompass a range of ±0.5%.

The formulations of the invention may also comprise compounds that are specifically useful for protecting the polypeptide of the invention during freeze-drying. Such compounds are also known as lyoprotectants, and are well known to the skilled person. Specific examples include, but are not limited to sugars like sucrose, sorbitol or trehalose; amino acids such as glutamate, in particular monosodium glutamate or histidine; betain, magnesium sulfate, sugar alcohols, propylene glycol, polyethylene glycols and combinations thereof. By appreciating the invention, the required amount of such a compound to be added can readily be determined by the skilled person under consideration of stability of the formulation in liquid form and when undergoing lyophilization.

Formulations that are particularly suitable for freeze-drying may furthermore comprise bulking agents. Suitable agents are widely known to the skilled person. It has been shown that a formulation comprising sucrose was not only particularly suited for maintaining the physical stability, during e.g. storage and freeze-thawing, of the vWF binders, but also as lyoprotectant.

Detergent

In a further embodiment of the invention, the formulation according to any aspect of the invention may further comprise a detergent or surfactant. Suitable detergents or surfactants for use with the invention include, but are not limited to, polyoxyethylene sorbitan fatty acid esters e.g. polysorbate-20, -40, -60, -65, -80 or -85. Common brand names for polysorbates include Alkest, Canarcel and Tween. The skilled person knows further non-limiting examples of detergents, such as those listed e.g. in WO2010/077422. In a preferred embodiment, the detergent is a non-ionic detergent. More specifically, the detergent is polysorbate-80, also designated Tween-80 hereafter. The skilled person can readily determine a suitable concentration of detergent for a formulation of the invention. Typically, the concentration will be as low as possible, whilst maintaining the beneficial effects of the detergents, e.g. a stabilizing effect under conditions of shear stress, e.g. stirring, which reduces aggregation of the formulated vWF binders. In exemplary, non-limiting embodiments, the concentration of the detergent may be in the range of 0.001 to 0.5%, e.g. 0.001%, 0.002%, 0.003%, 0.004%, 0.005%, 0.01%, 0.015%, 0.02%, 0.025%, 0.03%, 0.035%, 0.04%, 0.045%, 0.05%, 0.1%, 0.2%, 0.3%, 0.4% or 0.5%, preferably in a concentration between 0.01 and 0.05%, more preferably between 0.01 and 0.02%, e.g. 0.01% (v/v).

Combinations

The various embodiments as described above in Sections 5.5.1 to 5.5.4 can be combined in formulations of the invention without limitations. For example, ranges of values using a combination of any of the above recited values as upper and/or lower limits are intended to be included. However, preferable non-limiting examples of formulations include formulations wherein the buffer is a citrate buffer at about pH 6.5, preferably at a concentration of 20 mM, and the formulation further comprises sucrose, preferably at a concentration of about 7% (w/v), and optionally further comprises a non-ionic detergent such as Tween-80, preferably at a concentration of 0.01% (v/v).

Further Processing

As outlined, any of the above formulations can be further processed e.g. by lyophilization, spray-drying or freezing, e.g. bulk freezing. The resulting processed product has characteristics derived from the liquid starting formulation, as defined above. Where necessary, additional agents may be included for further processing, such as, for instance, lyoprotectants, etc.

Freezing

In some cases, formulations containing vWF binders are frozen for storage. Accordingly, it is desirable that the formulation be relatively stable under such conditions, such as freeze-thaw (FT) cycles. One method of determining the suitability of a formulation is to subject a sample formulation to at least two, e.g., three, four, five, eight, ten, or more cycles of freezing (at, for example −20° C. or −70° C.) and thawing (for example by fast thaw in a 25° C. water bath or slow thaw at +2° C. to +8° C.), determining the mass recovery of the original product and the presence and/or amount of LMW species and/or HMW species that accumulate after the FT cycles and comparing it to the amount of LMW species or HMW species present in the sample prior to the FT procedure, e.g. by SE-HPLC. An increase in the LMW or HMW species indicates decreased stability.

Lyophilization

Formulations can be stored after lyophilization. Therefore, testing a formulation for the stability of the polypeptide component of the formulation after lyophilization is useful for determining the suitability of a formulation. The method is similar to that described, supra, for freezing, except that the sample formulation is lyophilized instead of frozen, reconstituted to its original volume, and tested for the presence of LMW species and/or HMW species. The lyophilized sample formulation is compared to a corresponding sample formulation that was not lyophilized. An increase in LMW or HMW species in the lyophilized sample compared to the corresponding sample indicates decreased stability in the lyophilized sample. In general, a lyophilization protocol includes loading a sample into a lyophilizer or freeze-dryer, a pre-cooling period, freezing, vacuum initiation, ramping to the primary drying temperature, primary drying, ramping to the secondary drying temperature, secondary drying, and stoppering of the sample. Although the process of freeze-drying is well known in the art, various factors determine the freeze-drying characteristics of a sample, including: the glass transition temperature (Tg') and collapse temperature (Tc). Additional parameters that can be selected for a lyophilization protocol include vacuum (e.g., in microns) and condenser temperature.

Suitable ramp rates for temperature are between about 0.1° C./min. to 2° C./min., for example 0.1° C./min. to 1.0° C./min., 0.1° C./min. to 0.5° C./min., 0.2° C./min. to 0.5° C./min., 0.1° C./min., 0.2° C./min., 0.3° C./min., 0.4° C./min., 0.5° C./min., 0.6° C./min., 0.7° C./min., 0.8° C./min., 0.9° C./min., and 1.0° C./min. Suitable shelf temperatures during freezing for a lyophilization cycle are generally from about −55° C. to −5° C., −25° C. to −5° C., −20° C. to −5° C., −15° C. to −5° C., −10 C to −5° C., −10° C., −11° C., −12° C., −13° C., −14° C., −15° C., −16° C., −17° C., −18° C., −19° C., −20° C., −21° C., −22° C., −23° C., −24° C., or −25° C. Shelf temperatures can be different for primary drying and secondary drying, for example, primary drying can be performed at a lower temperature than secondary drying. In a non-limiting example, primary drying can be executed at 0° C. or alternatively at +5° C. and the secondary drying at +25° C. In some cases, an annealing protocol is used during freezing and prior to vacuum initiation. In such cases, the annealing time must be selected and the temperature is generally above the glass transition temperature of the composition. In general, the annealing time is about 2 to 20 hours, about 3 to 19 hours, about 2 to 10 hours, about 3 to 5 hours, about 3 to 4 hours, about 2 hours, about 3 hours, about 5 hours, about 8 hours, about 10 hours, about 12 hours, about 15 hours or about 19 hours. The temperature for annealing is generally from about –35° C. to about –5° C., for example from about –25° C. to about –8° C., about –20° C. to about –10° C., about –25° C., about –20° C., about –15° C., about 0° C., or about –5° C. In some cases, the annealing temperature is generally from –35° C. to +5° C., for example from –25° C. to –8° C., –20° C. to –10° C., –25° C., –20° C., –15° C., 0° C., +5° C.

The stability of the formulations described herein can be tested using a variety of lyophilization parameters including: the primary drying shelf temperatures from –25° C. to +30° C., and secondary drying durations of 2 hours to 33 hours at 0° to +30° C. The temperature for secondary drying should be as high as possible, without causing degradation of the active pharmaceutical ingredient.

An excipient to be used in a formulation of this invention should preferably satisfy one or more of the following parameters: be pharmacologically inert; be compatible with processing requirements; be well tolerated by the patient; be non-damaging to the active material; provide a soluble, absorbable product; provide a shelf-stable product; and provide a commercially acceptable product.

Figure 1:
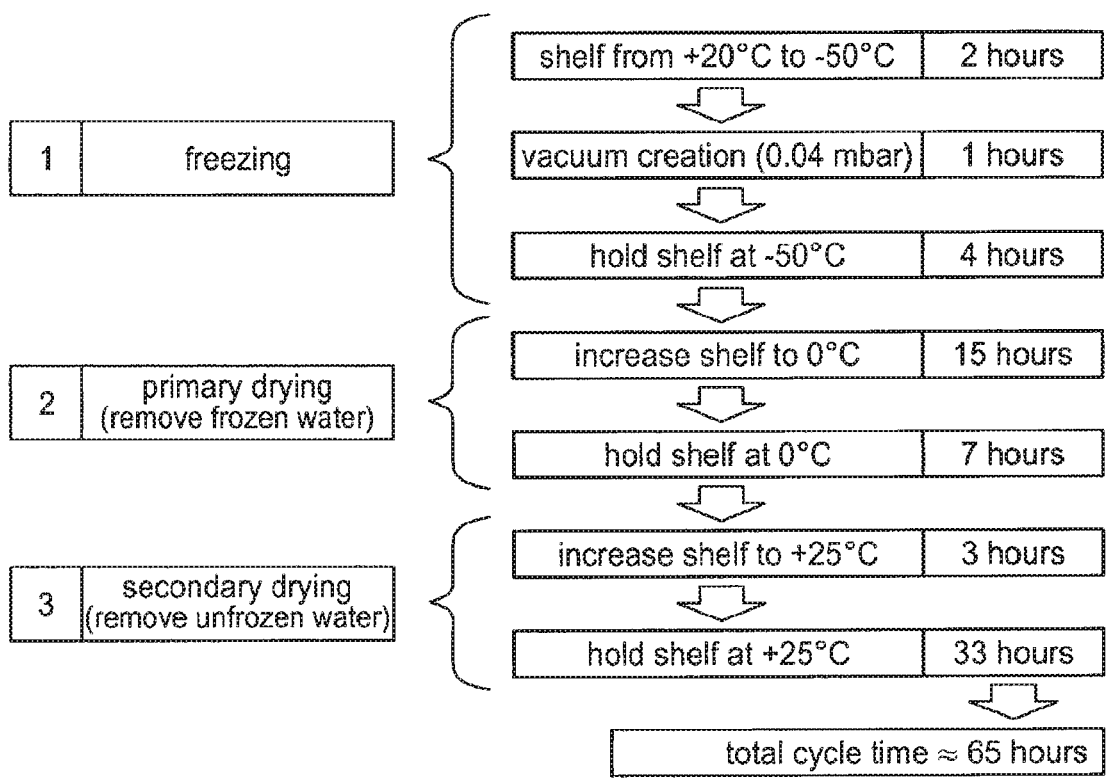
FIG. 1 Flow chart representing the different steps of the standard 65 h-lyophilization program performed for ALX-0081.

In an embodiment, the formulation of the present invention is prepared by freeze-drying, for instance as outlined in FIG. 1 or Table 14.

It was demonstrated that lyophilization of citrate/sucrose based formulations dramatically improves stability of the vWF-binders. In particular, the citrate/sucrose based formulations essentially prevent chemical modifications that occur in the liquid form, but with the exception of small quantities of pyroglutamate formation. Unexpectedly, lowering the citrate concentration and at the same time increasing the sucrose concentration improved chemical stability, e.g. decreased pyroglutamate formation. The vWF binder was demonstrated to be robust after lyophilization to extremes in product temperature. Indeed, the stability profile was identical for material that had been prepared using a variety of freeze-drying cycles.

In general, a lyophilization cycle can run from 10 hours to 100 hours, e.g., 20 hours to 80 hours, 30 hours to 70 hours, 40 hours to 60 hours, 45 hours to 50 hours, 50 hours to 66 hours.

In a non-limiting example, a formulation of 20 mM citrate, 7% sucrose, 0.01% Tween-80, pH 6.5, at a protein concentration of 12.5 mg/mL vWF-binder was formulated in bulk and lyophilized.

Non-limiting examples of the temperature range for storage of a formulation of the invention are about –20° C. to about +50° C., e.g., about –15° C. to about +40° C., about –15° C. to about +30° C., about –15° C. to about +20° C., about +5° C. to about +25° C., about +5° C. to about +20° C., about +5° C. to about +15° C., about +2° C. to about +12° C., about +2° C. to about +10° C., about +2° C. to about +8° C., about +2° C. to about +6° C., or about +2° C., +3° C., +4° C., +5° C., +6° C., +7° C., +8° C., +10° C., +15° C., +25° C., +30° C. or +40° C. Notwithstanding the storage temperatures, in certain cases, samples are stable under temperature changes that may transiently occur during storage and transportation conditions that can be anticipated for such compositions.

It has been established that by working with the formulations of the invention as defined herein, it is possible to obtain a resultant dried powder which exhibits a particle size suitable for comfortable retention and a fast dissolution of the active material. The dried formulation according to the invention comprises particles which remain stable and uniform throughout processing, final finishing, storage and distribution. The formulation is shelf-stable and free-flowing, presents no problems when dispensed into its final container and is simple to administer by the patient.

Spray-Drying

In some cases, a formulation is spray-dried and then stored. Spray-drying is conducted using methods known in the art, and can be modified to use liquid or frozen spray-drying (e.g., using methods such as those from Niro Inc. (Madison, WI), Upperton Particle Technologies (Nottingham, England), or U.S. Patent Publ. Nos. 2003/0072718 and 2003/0082276), or Buchi (Brinkman Instruments Inc., Westbury, NY).

Diluent

The lyophilized formulations as described herein may be reconstituted as needed by mixing the lyophilized form with a suitable diluent to resolubilize the original formulation components to a desired concentration. The term "diluent" as used herein refers to a pharmaceutically acceptable (safe and non-toxic for administration to a human) solvent for altering or achieving an appropriate concentration as described herein. Exemplary diluents include, but are not limited to, sterile water (e.g. WFI, Milli-Q water), saline, glucose, dextrose, Ringer and aqueous buffer solutions.

Pharmaceutical Compositions

The formulations of the present invention are preferably suitable for use in methods of therapy of the animal or human body. Hence, the invention pertains to pharmaceutical or diagnostic compositions comprising a formulation of the polypeptide according to any aspect of the invention or obtainable by any method or process of the invention.

The formulations of the invention are preferably pharmaceutical formulations. In particular, the formulations are suitable for parenteral administration to a human, e.g. subcutaneous, intravenous, intramuscular, intradermal or intraperitoneal administration, preferably intravenous or subcutaneous administration. Administration encompasses any way of administering a liquid formulation, in particular injection. Other forms of systemic administration, e.g. via implantable devices, micro-infusion pumps (optionally implantable), and/or (implantable) sustained release formulations, e.g. deposits, gels, biodegradable polymer formulations are also within the scope of the present invention. Pharmaceutical compositions are sterile and stable during manufacture and storage, as derivatives/degradation products of the vWF binders are undesired in a clinical setting. The composition will also be of high purity, e.g. exclude the presence of bacterial products such as LPS. The formulations can be sterilized by any suitable means, e.g. sterile filtration, irradiation and combinations thereof, etc. Preferably, the pharmaceutical compositions are adapted to parenteral (especially intravenous, intra-arterial or transdermal) administration. Intravenous administration is considered to be of particular importance. Preferably the vWF binder is in the form of a parenteral form, most preferably intravenous and subcutaneous forms.

To be suitable as a pharmaceutical formulation, the formulation of the invention will typically comprise the polypeptide of the invention (i.e. the active agent) in a suitable ratio to the volume. For example, for subcutaneous injection the concentration of active agent may be higher, in order to allow the necessary pharmaceutical dose to be administered in a smaller volume, as compared to a formulation for intravenous injection. However, in some embodiments the concentration of active agent will be identical for subcutaneous or intravenous injection, and can be in the exemplary ranges as defined herein.

In some embodiments, the formulations of the invention may comprise additional agents, e.g. additional active agents, excipients, stabilizers, preservatives such as antimicrobial agents, etc.

The formulations of the invention are preferably in a dose applied to a patient in need thereof. Nevertheless, the particular mode of administration and the dosage may be selected by the attending physician taking into account the particulars of the patient, especially age, weight, life style, activity level, and general medical condition as appropriate. More specifically, ALX-0081 is administered intravenously or subcutaneously in a 24 h dose interval. Even more preferably, ALX-0081, is administered intravenously or subcutaneously in a 24 h dose interval upon consideration of the aggregation activity, e.g. measured by RIPA, ristocetin induced platelet aggregation—(Favaloro E J. *Clin Haematol* 2001; 14: 299-319) and/or Ristocetin Cofactor Platelet Agglutination Assay—(Howard M A, Firkin B G. Ristocetin—a new tool in the investigation of platelet aggregation. Thrombosis et Diathesis Haemorrhagica 1971; 26: 362-9). For example, a further dose is not administered if the aggregation activity is estimated to stay below 10% measured by RIPA or stay below 20% measured by RICO for the next 6 hours (Clinically relevant inhibition).

However, in general the dosage of the vWF binders may depend on various factors, such as effectiveness and duration of action of the active ingredient, warm-blooded species, and/or sex, age, weight and individual condition of the warm-blooded animal.

Normally the dosage is such that a single dose of a vWF binder, is for instance estimated based on in vitro results, or for instance based on results from a dose escalating study to test subchronic toxicity in cynomolgus monkeys. Based on such a preclinical data set, a starting and subsequent escalating dose for a vWF binder can be determined. For instance a dose may be from 0.5-50 mg, especially 1-30 mg, and is administered to a warm-blooded animal weighing approximately 75 (+/−30) kg (but can be different as well to this norm). If desired, this dose may also be taken in several, optionally equal, partial doses ("mg" means mg drug per mammal—including human—to be treated).

The dose mentioned above—either administered as a single dose (which is one embodiment) or in several partial doses—may be repeated, as mentioned above for example once every six hours, once every 12 hours, or once daily. In other words, the pharmaceutical compositions may be administered in regimens ranging from continuous 6 hourly therapy to longer interval dosing therapy.

Preferably, the vWF binders are administered in doses which are in the same order of magnitude as those used in the adjunct treatment in patients in need for PCI as herein suggested for ALX-0081. For example, for the preferred 12A02H1-containing vWF binders, e.g. ALX-0081 and functional variants thereof, doses of vWF binders in the range from about 0.5 to about 40 mg, preferably from about 1 to about 35 mg, or from about 2 to about 30 mg, even more preferably from about 3 to about 25 mg or from about 4 to about 20 mg, or from about 5 to about 17.5 mg, or even from about 6 to about 16 mg, or from about 7.5 to about 15 mg, or even from about 10 to about 14 mg, more preferably about 10, about 12.5 or about 13.8 mg, may be used for acute treatment in human patients.

Formulations in single dose unit form contain preferably from about 0.5 to about 40 mg, preferably from about 1 to about 35 mg, or from about 2 to about 30 mg, even more preferably from about 3 to about 25 mg or from about 4 to about 20 mg, or from about 5 to about 17.5 mg, or even from about 6 to about 16 mg, or from about 7.5 to about 15 mg, or even from about 10 to about 14 mg, more preferably about 10, about 12.5 or about 13.8 mg and formulations not in single dose unit form contain preferably from about 0.5 to about 40 mg, preferably from about 1 to about 35 mg, or from about 2 to about 30 mg, even more preferably from about 3 to about 25 mg or from about 4 to about 20 mg, or from about 5 to about 17.5 mg, or even from about 6 to about 16 mg, or from about 7.5 to about 15 mg, or even from about 10 to about 14 mg, more preferably about 10, about 12.5 or about 13.8 mg of the active ingredient.

Pharmaceutical preparations for parenteral administration are, for example, those in dosage unit forms, such as ampoules. They are prepared in a manner known per se, for example by means of conventional mixing, dissolving or lyophilizing processes.

Parenteral formulations are especially injectable fluids that are effective in various manners, such as at site of PCI, intra-arterially, intramuscularly, intraperitoneally, intranasally, intradermally, subcutaneously or preferably intravenously. Such fluids are preferably isotonic aqueous solutions or suspensions which can be prepared before use, for example from lyophilized preparations or concentrate which contain the active ingredient alone or together with a pharmaceutically acceptable carrier. The pharmaceutical preparations may be sterilised and/or contain adjuncts, for example preservatives, stabilisers, wetting agents and/or emulsifiers, solubilisers, salts for regulating the osmotic pressure and/or buffers.

Suitable formulations for transdermal application include an effective amount of the active ingredient with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the active ingredient of the skin of the host at a controlled and predetermined rate over a prolonged period of time, and means to secure the device to the skin.

The following table provides some non-limiting examples of citrate and phosphate buffer based formulations of the present invention. All formulations can be adjusted to an osmolality of 290±60 mOsm/kg by adding a suitable excipient, if desired. The formulations can comprise any one or more of the polypeptides of the present invention, e.g. SEQ ID NOs: 1-19, particularly SEQ ID NO: 1.

| Buffer | Buffer conc (mM) | pH | Buffer | Buffer conc (mM) | pH |
|---|---|---|---|---|---|
| Citrate | 10 | 6.0 | phosphate | 10 | 6.5 |
| Citrate | 10 | 6.5 | phosphate | 10 | 7.0 |
| Citrate | 10 | 7.0 | phosphate | 10 | 7.5 |
| Citrate | 20 | 6.0 | phosphate | 20 | 6.5 |
| Citrate | 20 | 6.5 | phosphate | 20 | 7.0 |
| Citrate | 20 | 7.0 | phosphate | 20 | 7.5 |
| Citrate | 30 | 6.0 | phosphate | 30 | 6.5 |
| Citrate | 30 | 6.5 | phosphate | 30 | 7.0 |
| Citrate | 30 | 7.0 | phosphate | 30 | 7.5 |
| Citrate | 40 | 6.0 | phosphate | 40 | 6.5 |
| Citrate | 40 | 6.5 | phosphate | 40 | 7.0 |
| Citrate | 40 | 7.0 | phosphate | 40 | 7.5 |
| Citrate | 50 | 6.0 | phosphate | 50 | 6.5 |
| Citrate | 50 | 6.5 | phosphate | 50 | 7.0 |
| Citrate | 50 | 7.0 | phosphate | 50 | 7.5 |

The buffer concentrations in this table are understood to optionally encompass ±5 mM. The pH values are understood to optionally encompass ±0.2. Each of the above buffers can be combined with one or more excipients selected from e.g. NaCl at a concentration of e.g. 25, 30, 40, 50, 60, 70, 100, 150, 250 or 500 mM; mannitol at a concentration of e.g. 2, 3 or 4% (w/v); glycine at a concentration of e.g. 25, 30, 40, 50, 60, 70, 100, 150, 250 or 500 mM; trehalose at a concentration of e.g. 25, 30, 40, 50, 60, 70, 100, 150, 250 or 500 mM and sucrose at a concentration of e.g. 4, 5, 6, 7, 8 or 9% (w/v), and/or a surfactant, e.g. Tween-80 at a concentration of 0.001%, 0.002%, 0.003%, 0.004%, 0.005%, 0.01%, 0.015%, 0.02%, 0.025%, 0.03%, 0.035%, 0.04%, 0.045%, 0.05%, 0.1%, 0.2%, 0.3%, 0.4% or 0.5% (v/v).

Effects of the Invention

The invention provides stable formulations of the vWF binders, e.g. the immunoglobulin single variable domains as defined herein, e.g. SEQ ID NOs: 1-19, in particular SEQ ID NO: 1. "Stable" generally means that the immunoglobulin single variable domains do not suffer from significant physical or chemical changes upon storage for prolonged periods of time, e.g. 1 month to 36 months, even if exposed to one or more chemical or physical stresses such as elevated temperatures (equal to or higher than +25° C.), or physical stress such as shaking or stirring. More in particular, "stable" means that upon storage for prolonged periods (as defined) under conditions (as defined) there is only a limited formation (as defined) of one or more of degradation products, e.g. low molecular weight (LMW) derivatives (fragments) of the polypeptides of the invention; and/or chemical derivatives or modifications such as e.g. pyroglutamate variants; and/or high molecular weight (HMW) derivatives (oligomers or polymers) formed e.g. by aggregation.

The skilled person is well acquainted with techniques to assess protein size, e.g. size exclusion chromatography-HPLC or to assess the formation of chemical derivatives, e.g. reversed phase HPLC. The skilled person is also familiar with commonly used apparatuses and software tools for performing such analyses. For example, the skilled person knows commonly used software to analyse chromatographic runs e.g. in terms of relative peak area. Examples include (but are not limited to) Agilent 1200 HPLC system equipped with ChemStation software (Agilent Technologies, Palo Alto, USA, Rev B) or Dionex Ultimate 3000 HPLC system equipped with Chromeleon software (Dionex Corporation, Sunnyvale, CA, USA, V6.8).

General techniques that can be used to assess stability of a protein, e.g. an immunoglobulin single variable domain include static light scattering, tangential flow filtration, Fourier transform infrared spectroscopy, circular dichroism, urea induced protein unfolding, intrinsic tryptophan fluorescence and/or 1-anilin-8-naphtalenesulfonic acid protein binding. In addition, the formulation of the invention shows little or no loss of potency/biological activity in the course of storage and/or under influence of one or more stresses as defined herein. Biological activity and/or potency can be determined e.g. as described in WO2006/122825.
Thermal Stability The formulations of the present invention are characterized by providing a high thermal stability of the vWF binders, e.g. the immunoglobulin single variable domains as defined herein. Thermal stability can be evaluated e.g. by determining the melt temperature (Tm). Suitable techniques for determining the melt temperature are known and include e.g. a thermal shift assay (TSA) e.g. as described herein.

More specifically, the formulations of the present invention lead to an increase of Tm for the immunoglobulin single variable domains as determined by TSA in comparison to other formulations. This effect is exemplified in Table 1 of the experimental section.

As can be ascertained from the experimental section, high thermal stability, i.e. high Tm can be taken as an indication for storage stability.

According to the present invention, the formulations of the invention have a positive influence on Tm over a broad range of pH values, e.g. between 6.0 and 7.0 for citrate buffer, and 6.5 to 7.5 for phosphate buffer. The most advantageous effect on Tm can be observed for citrate buffer at pH 6-7, and in particular for pH 6.5±0.2 and phosphate buffer at pH 6.5 to 7.5, in particular pH 7.1±0.2.

The addition of excipients can have a further positive or negative effect on Tm (Table 1). For example, trehalose can increase Tm (in the context of a particular buffer) e.g. between 150 mM and 300 mM. Also mannitol or sucrose had a clear positive effect on Tm. These excipients can find use in particular embodiments of the invention, e.g. formulations where a bulking agent or lyoprotectants are advantageous. These exemplary embodiments do not preclude the use of further known lyoprotectants or bulking agents, either alone or in combination with mannitol or sucrose.

As evidenced by the experimental section of this description, Tm as determined by TSA serves as a valuable indicator for stability of the vWF binders, e.g. the immunoglobulin single variable domains of the invention.
Stability as Concerns Mechanical Stress The formulations of the invention are characterized by a high stability as concerns mechanical stress, such as stirring, shaking or shear stress. A possible assay to evaluate stability under mechanical stress is monitoring 500 nm scatter signal in a spectrofluorometer or via UV spectrophotometry e.g. at 340 nm. An increase in scatter or UV absorption reflects the formation of aggregates. When aggregates are formed (HMW), the increase over time follows a linear curve for which a slope (scatter intensity/time or absorbance units/s) can be determined. Preferably, the formulations of the present invention are characterized by a slope of less than 0.0006, e.g. less than 0.0005, e.g. between 0 and 0.0004 (cf. FIGS. 4 A and 4B).

The formulations comprising citrate buffers are particularly preferred and have a positive effect on protein recovery after e.g. stirring as defined above. For example, mass recovery is at least 90%, 95%, 98% or 100%. Protein recovery is determined in comparison to the total protein content before stressing the sample e.g. by stirring. The formulations comprising phosphate buffers result in a recovery of at least 75%, 80%, 85% or even more after stirring as defined above.

At an exemplary, non-limiting concentration of 5 mg/mL, the formulations of the invention only form reversible aggregates in response to stirring in the absence of Tween. Thus, the formulations of the invention prevent the formation of irreversible aggregates under mechanical stress. Accordingly, in a further embodiment of the invention, the formulations of the invention may comprise a non-ionic detergent as defined above, e.g. Tween-80, e.g. at a concentration as defined above, e.g. between 0.01% and 0.02% (v/v). The addition of the detergent can further improve physical stability of the formulation. For instance, at a non-limiting exemplary concentration of 5 mg/mL, the addition of the detergent can prevent the formation of aggregates (reversible and irreversible) as determined e.g.

by monitoring 500 nm scatter signal in a spectrofluorometer or by UV spectrophotometry (340 nm) (FIGS. 4A and 4B).

The physical stability of the formulations of the present invention can also be demonstrated by SE-HPLC. Different non-limiting formulations of immunoglobulin single variable domains of the present invention can withstand mechanical stress, e.g. stirring stress, without forming oligomers (HMW) or degradation products (LMW). The formulations of the invention remain stable without degradation or oligomerization, as determined e.g. after 1.5 hours of stirring by SE-HPLC analysis.

No oligomerization or degradation (e.g. as determined by RP-HPLC (only degradation) or SE-HPLC profile) is detected in any of the formulations. Thus, according to a preferred embodiment of the invention, the formulations comprise a citrate buffer and show a recovery of at least 70%, 75%, 80%, 85%, 90%, 95%, 98%, or even about 100%, e.g. under conditions as described above, wherein recovery is determined e.g. by RP-HPLC or SE-HPLC in comparison with a non-stressed sample. Advantageously, the excipient in the context of a citrate buffer can be sucrose, and recovery as defined above is at least 80%, 85%, 90%, 95%, 98%, or even about 100%.

Stability Testing of Liquid Formulations

Storage Stability

The liquid formulations of the invention provide for good stability when stored, e.g. at a temperature of −70° C., −20° C., +5° C., +25° C. or +40° C., e.g. for 1-36 months, such as 1, 1.5, 3, 6, 9, 12, 18, 24, 30 or 36 months. The most advantageous results can be obtained with citrate buffer based formulations as exemplified in Table 5.

The skilled person will further recognize that storage at +25° C., and more in particular +40° C. represent stressed storage conditions. Such conditions are expected to increase and accelerate any signs of instability, e.g. chemical or physical instability. Hence, relatively short storage at e.g. +25 or +40° C. provides a good indication for long term storage stability under milder conditions (e.g. +5° C. or frozen).

Storage Stability in Terms of Protein Recovery

For example, the formulations of the present invention provide for a protein recovery of at least 95%, e.g. at least 96, 97, 98, 99 or even about 100% after storage at a temperature between −70° C. and +40° C. Protein recovery can be determined by any known means to quantify proteins, e.g. by RP-HPLC or SE-HPLC, as exemplified in Table 5 as compared to a reference sample kept at −70° C. These results can be observed e.g. after storage at the indicated temperature of 1 month, 1.5 months, 3 months, 6 months, 9 months, 12 months, 18 months, 24 months, 30 months or even at 36 months.

Storage Stability in Terms of Chemical Derivatives/Degradation Products

Moreover, the formulations of the present invention minimize production of chemical derivatives, e.g. pyroglutamate variants, of less than 5.0% in peak size as determined e.g. by RP-HPLC (cf. Table 5). In this type of analysis, the area of a given peak is compared to the total area of the chromatogram, and a relative area is allocated to each peak. The skilled person knows suitable analyzing means, e.g. suitable software, to analyze the chromatograms (specific, non-limiting examples include Agilent 1200 HPLC system equipped with ChemStation software (Agilent Technologies, Palo Alto, USA, Rev B) or Dionex Ultimate 3000 HPLC system equipped with Chromeleon software (Dionex Corporation, Sunnyvale, CA, USA, V6.8). Thus, preferably, the pyroglutamate variant contributes to a peak area of less than 5%, preferably less than 4.6%, e.g. 4.5, 4.3, 4.2, 4.0 or even less than 3.8% as determined by RP-HPLC upon storage at temperatures between −70° C. and +40° C., e.g. +40° C., e.g. after storage for a duration as defined above, e.g. 1 month.

The formulations of the present invention also minimize oxidation, such as the formation of oxidized products (as determined e.g. by RP-HPLC) over a storage period as defined above, e.g. 1 month at a temperature between −70° C. and +40° C. (cf. Table 5). Thus, the formulations of the present invention result in oxidation variants with a peak area of less than 3%, preferably less than 2.7%, preferably less than 2.5%, e.g. less than 2.3%, 2.2%, e.g. 2.0, or even less such as 1.7% or 1.5% upon storage at temperatures between −70° C. and +40° C., e.g. +40° C., e.g. after storage for a duration as defined above, e.g. 1 month (as determined e.g. by RP-HPLC).

Storage Stability in Terms of Oligomerization

The formulations of the invention also provide for storage stability, such that no apparent soluble oligomeric material is formed (as defined e.g. by SE-HPLC) at storage temperatures between −70° C. and +40° C., after storage durations as defined above, e.g. 1 month; or less than 1%, preferably less than 0.5%, e.g. 0.3% soluble oligomeric material is formed (as defined e.g. by SE-HPLC) at storage temperatures between −70° C. and +40° C., e.g. +40° C., after storage durations as defined above, e.g. 1 month.

The present invention also has the effect of providing an aggregation index as determined by absorbance values $[(100 \times A340)/(A280-A340)]$ which remains below 0.15, preferably below 0.1 after storage at −70° C. or +40° C. for storage of a duration as defined above, e.g. 1 month.

Storage Stability as Reflected in Recovery of Main Product

The formulations of the invention have the effect that the main product peak area, as determined e.g. by RP-HPLC (cf. Table 5) is about 90% after storage between −70° C. and +40° C. after a storage duration as indicated above, e.g. 1 month; or the main product peak, as determined e.g. by RP-HPLC (cf. Table 5) is at least 85%, or more, such as 86%, 87% or 88%. More preferably, the main peak is 90%, 92% or 95%, e.g. at least 97%, more preferably 100% after storage between −70° C. and +40° C., e.g. +40° C. after a storage duration as indicated above, e.g. 1 month; or the main product peak, as determined e.g. by SE-HPLC is at least 85%, at least 90%, preferably at least 95%, e.g. at least 98% or even about 100% after storage between −70° C. and +40° C., e.g. +40° C., after a storage duration as indicated above, e.g. 1 month.

The formulations according to the present invention also have the effect that the main peak area as determined by RP-HPLC after storage e.g. at a concentration up to 20 mg/mL at between −70° C. and +25° C. for between 1 and 3 months remains unchanged as compared to the formulation prior to storage, and represents at least 90%, more preferably at least 95% of the total peaks, wherein the reference sample has a main peak of e.g. 95%. Upon storage at +40° C. for 1 month the formulation of the present invention retains the main peak as determined by RP-HPLC of at least 80%, 85% or 90%; after storage for 2 months of at least 80%, or 85%, and after storage for 3 months of at least 75% or 80%.

Moreover, as determined by cIEF, the formulation of the present invention has the effect of providing recovery of the main product after storage at a concentration of e.g. up to 20 mg/mL for between 1-3 months at a temperature between −70° C. and +40° C. that is comparable to the reference sample (formulation without storage, main peak is at least 98%), e.g. the main peak is at least 85%, or more, such as 86%, 87% or 88%. More preferably, the main peak is 90%, 92% or 95%, e.g. at least 97%, more preferably 100% after storage between −70° C. and +40° C.

Stability Under Freeze-Thaw Conditions

Apart from providing stability of the formulations under conditions of storage that remain constant over time (e.g. storage at +5° C.), or include a single FT cycle (e.g. storage at −20° C. or −70° C.), a further effect of the invention is stability under conditions of repeated FT cycles. Every transition between frozen and liquid state and vice versa imposes particularly stressful conditions upon the immunoglobulin single variable domains.

The formulations of the invention also have the effect of providing good stability under FT conditions. For example the formulations of the invention can be subjected to e.g. 10 FT cycles between −70° C. and room temperature (e.g. +25° C.), or −20° C. and room temperature. The immunoglobulin single variable domains comprised in the formulations will withstand these conditions without significant deterioration, as ascertained e.g. by RP-HPLC or SE-HPLC. The effect of repetitive FT cycles on different non-limiting embodiments of formulations of the invention were evaluated, and reveal that in all cases chemical and physical integrity of the vWF binders, e.g. immunoglobulin single variable domains has been preserved. Overall recovery was in the range between 95 and 100%, preferably at least 95, 98 or 99%. The relative proportion of the different peaks remained unchanged in comparison to a control subjected to only one FT cycle.

More specifically, at a concentration of between 5 mg/mL and 20 mg/mL, 10 FT cycles resulted in a recovery (as determined on the basis of e.g. total peak area, i.e. AU of polypeptide, as determined either by RP-HPLC or SE-HPLC that is at least 90%, 95%, 98% or 100%; wherein in a particular embodiment the RP-HPLC or SE-HPLC profile was unchanged as compared to a reference sample (1 FT cycle).

Stability in Terms of Potency

The skilled person knows various ways to determine potency of vWF binders, in particular immunoglobulin single variable domains, more specifically polypeptides according to any one of SEQ ID NOs: 1-19, e.g. SEQ ID NO: 1 (see, for example, experimental section of WO2006/122825, e.g. Examples 3-6, 18 and 19, or the experimental section of WO2009/115614).

In one embodiment, potency of the polypeptide of the present invention can be determined by binding to its antigen by a conventional assay, e.g. ELISA, Biacore, RIA, FACS, etc.

The potency of vWF binders remained acceptable in the formulations of the invention as tested under stressed conditions, i.e. 4 weeks storage at +40° C.

Stability in Terms of Compatibility

The formulations of the present invention also are compatible with a range of different diluents. For instance, the formulations can be mixed/diluted with such diluents, without affecting chemical and physical stability of the immunoglobulin single variable domains.

Thus, the formulations of the present invention also provide stability over a broad range of concentrations, as defined herein.

Summary of Stabilizing Effects

The formulations of the present invention have the effect of maintaining the chemical and physical integrity of the polypeptides of the present invention even after prolonged storage, e.g. for durations as defined above, at temperatures between −70° C. and +25° C.

Storage of immunoglobulin single variable domains as defined herein, in particular ALX-0081 at −70° C. for 1 month did not affect their physicochemical characteristics for any of the formulations of the invention, in particular the non-limiting examples of buffers tested in the experimental section. Storage did not have a significant effect on RP-HPLC, SE-HPLC or cIEF profiles.

Stability Testing of Lyophilized Formulations

In addition, the invention provides stable formulations of the vWF binders, e.g. the immunoglobulin single variable domains as defined herein, e.g. SEQ ID NOs: 1-19, preferably SEQ ID NO: 1, which are particularly useful for lyophilization. The formulations of the invention resulted in improved solubility and improved storage stability after lyophilization.

Storage Stability

The formulations of the invention may provide for good stability after lyophilization when stored, e.g. at a temperature of −70° C., −20° C., +5° C., +25° C. or +40° C., e.g. for 1-36 months, such as 1, 1.5, 3, 6, 9, 12, 18, 24, 30 or 36 months. The most advantageous results can be obtained with citrate buffer based formulations, e.g. formulations 3 and 7 as exemplified in the experimental section (e.g. good cake formation and no visuals signs of decay, FIGS. 6A and 6B). The skilled person can recognize that in the below discussion the preferred values reflect citrate buffer compositions, e.g. as exemplified in Table 8.

The skilled person will also recognize that storage at +25° C., and more in particular +40° C. represent stressed storage conditions. Such conditions are expected to increase and accelerate any signs of instability, e.g. chemical or physical instability. Hence, relatively short storage at e.g. +25° C. or +40° C. provides a good indication for extended storage stability under milder conditions (e.g. +5° C. or frozen).

Storage Stability in Terms of Protein Recovery

For example, the formulations of the present invention provide for a protein recovery after lyophilization of at least 95%, e.g. at least 96, 97, 98, 99 or even about 100% after storage at a temperature between −70° C. and +40° C. Protein recovery can be determined by any known means to quantify proteins, e.g. by content, RP-HPLC or SE-HPLC. These results can be observed e.g. after storage at the indicated temperature of 1-36 months, such as 1, 1.5, 3, 6, 9, 12, 18, 24, 30 or 36 months.

Storage Stability in Terms of Chemical Derivatives/Degradation Products

Moreover, the formulations of the present invention may prevent and minimize production of chemical derivatives after lyophilization, as confirmed by e.g. by SE-HPLC.

Storage Stability in Terms of Oliqomerisation

The formulations of the invention may also provide for storage stability after lyophilization, such that no apparent soluble oligomeric material is formed (as defined e.g. by SE-HPLC) at storage temperatures between −70° C. and +40° C., after storage durations as defined above, e.g. 1 month; or less than 1%, preferably less than 0.5%, e.g. 0.3% soluble oligomeric material is formed (as defined e.g. by SE-HPLC) at storage temperatures between −70° C. and +40° C., e.g. +40° C., after storage durations as defined above, e.g. 1-36 months, such as 1, 1.5, 3, 6, 9, 12, 18, 24, 30 or 36 months.

Storage Stability as Reflected in Recovery of Main Product

The formulations of the invention may also have the effect that after lyophilization the main product peak, as determined e.g. by SE-HPLC (cf. Table 18 and Tables 27-29) is about 100% after storage between −70° C. and +40° C. after a storage duration as indicated above, e.g. 1, 3, 6, 9, 12, 18 or 24 months; or the main product peak, as determined e.g. by SE-HPLC (cf. Table 18 and Tables 27-29) is at least 85%, or more, such as 86%, 87% or 88%. More preferably, the main peak is 90%, 92% or 95%, e.g. at least 97%, more preferably 100% after storage between −70° C. and +40° C., e.g. +25° C. after a storage duration as indicated above, e.g. 1, 3, 6, 9, 12, 18 or 24 months; or the main product peak, as determined e.g. by SE-HPLC is at least 85%, at least 90%, preferably at least 95%, e.g. at least 98% or even about 100% after storage between −70° C. and +40° C., e.g. +40° C., after a storage duration as indicated above, e.g. 1, 3, 6, 9, 12, 18 or 24 months.

The formulations according to the present invention also have the effect that after lyophilization the main peak as determined by RP-HPLC after storage e.g. at a concentration of 12.5 mg/mL at between −70° C. and +40° C. for between 1 and 12 months remains unchanged as compared to the formulation prior to storage, and represents at least 90%, more preferably at least 93% of the total peaks, wherein the reference sample has a main peak of e.g. 93% (cf. Table 15). Upon storage after lyophilization at +40° C. for up to 12 months the formulation of the present invention retains the main peak as determined by RP-HPLC of at least 91%, 92% or 93%.

Moreover, as determined by cIEF (cf. Tables 27-29), the formulations of the present invention have the effect of providing after lyophilization recovery of the main product after storage at a concentration of e.g. 12.7 mg/mL for between 1-24 months at a temperature between −70° C. and +40° C. that is comparable to the reference sample (formulation without storage, main peak is at least 96%), e.g. the main peak is at least 85%, or more, such as 86%, 87% or 88%. More preferably, the main peak is 90%, 92%, 93%, 94%, 95% or 96%, e.g. at least 97%, more preferably 100% after storage between −70° C. and +40° C.

Stability Under Freeze-Thaw Conditions

The formulations of the invention also have the effect of providing good stability after lyophilization under FT conditions. For example the formulations of the invention can be subjected to e.g. 5 FT cycles between −20° C. and room temperature (e.g. +25° C.). The immunoglobulin single variable domains comprised in the formulations will withstand these conditions without significant deterioration, as ascertained e.g. by RP-HPLC or SE-HPLC. In all cases chemical and physical integrity of the vWF binders, e.g. immunoglobulin single variable domains, has been preserved. Overall recovery was in the range between 95 and 100%, preferably at least 95, 98 or 99% compared to a liquid control sample stored at −70° C.

More specifically, at a concentration of 16 mg/mL, 5 FT cycles resulted in a recovery (as determined on the basis of e.g. total area, i.e. AU) of polypeptide, as determined either by RP-HPLC or SE-HPLC that is at least 90%, 95%, 98%, 99% or 100%; wherein in a particular embodiment the RP-HPLC or SE-HPLC profile was unchanged as compared to a reference sample (liquid control sample stored at −70° C.) (cf. Table 12).

Stability in Terms of Potency

The skilled person knows various ways to determine potency of vWF binders, in particular immunoglobulin single variable domains, more specifically polypeptides according to any one of SEQ ID NOs: 1-19, e.g. SEQ ID NO: 1 (see, for example, experimental section of WO2006/122825, e.g. Examples 3-6, 18 and 19, or the experimental section of WO2009/115614). The potency of the vWF binders after lyophilization was not affected after repeated FT cycles in the formulations. In particular, the potency of vWF binders remained stable in the formulations of the invention as tested under stressed conditions, i.e. up to 12 months storage at +40° C. (Table 23) and even up to 24 months storage at +40° C. (Table 29). In one embodiment, potency of the polypeptide of the present invention after lyophilization can be determined by binding to its antigen by a conventional assay, e.g. ELISA, Biacore, RIA, FACS, etc. More specifically, in the formulations of the present invention at least 80%, preferably at least 90%, more preferably at least 95% or even at least 99% of the vWF binder retains it binding activity after storage under the above stress conditions compared to the binding activity prior to storage.

In a further aspect, the formulations of the present invention exhibit almost no loss in biological activity when comparing the liquid formulation of ALX-0081 to the lyophilized formulation, as assessed by various immunological assays including, but not limited to Biacore assay, enzyme-linked immunosorbent assay (ELISA), ristocetin induced cofactor activity assay (RICO) and/or Gyrolab-based assay (see Section 7.13 and Table 24).

Summary of Stabilizing Effects

The formulations of the present invention have the effect after lyophilization of maintaining the chemical and physical integrity of the polypeptides of the present invention, in particular ALX-0081, i.e. even after prolonged storage, e.g. for durations as defined above, at temperatures between −70° C. and +40° C., the purity/impurity profile of the product is essentially not changing. For example, prolonged storage after lyophilization did not have a significant effect on RP-HPLC, SE-HPLC or cIEF profiles as supported by the experimental section.

Methods of the Invention

The vWF binders of the invention can be produced by any commonly used method. Typical examples include the recombinant expression in suitable host systems, e.g. bacteria or yeast. The vWF binders will undergo a suitable purification regimen prior to being formulated in accordance to the present invention.

The present invention encompasses methods of producing the formulations as defined herein.

The purification and formulation steps may coincide, e.g. when the vWF binders of the invention are eluted from a column using a buffer according to the present invention. Alternatively, the formulations of the invention can be prepared by exchanging a buffer by any suitable means, e.g. means widely used in the art such as dialyzing, ultrafiltration, etc.

In some embodiments the method of producing a formulation of the invention may also relate to the reconstitution of a lyophilized or spray-dried formulation, e.g. by addition of water or a suitable buffer (which may optionally comprise further excipients).

The methods for preparing a formulation according to the present invention may encompass further steps, such as filling it into vials suitable for clinical use, such as sealed containers and/or confectioning it in a dosage unit form. The methods may also comprise further steps such as spray-drying, lyophilization, or freezing, e.g. bulk freezing. The invention also encompasses the containers, dosage unit forms, or other products obtainable by any of the methods recited herein.

The formulations of the present invention can be used to store the vWF binders, e.g. ISVDs as defined herein. Thus, the invention encompasses a method of storage of a vWF binder as used herein, characterized by the use of a formulation as defined herein. More specifically, the invention encompasses methods for stabilizing a vWF binder as defined herein for storage, comprising e.g. the preparation of a formulation as described herein. Storage can be 1-36 months, such as 1, 1.5, 3, 6, 9, 12, 18, 24, 30 or 36 months, e.g. at least 12 or even 24 months, optionally at a temperature between −70° C. and +40° C., such as −70° C., −20° C., +5° C., +25° C. or +40° C., preferably a temperature between −70° C. and +25° C., more preferably at a temperature between −20° C. and +5° C. Thus, storage may encompass freezing, freeze-drying (lyophilization) and/or spray-drying. The storage methods may furthermore comprise the assessment of physical and chemical integrity of the vWF binders as defined herein.

The present invention also relates to methods for analyzing formulations comprising at least one of the vWF binders as defined herein. The formulations can be analyzed for any signs of chemical or physical instability of the vWF binders as defined herein. For example, the formulations can be assessed for the presence of degradation products, e.g. low molecular weight derivatives such as proteolytic fragments; and/or for chemical derivatives, e.g. pyroglutamate variants; and/or for high molecular weight derivatives such as aggregates, agglomerates, etc. The formulation can also be assessed for total protein content and/or potency. Each of the various assay methods as referred to herein can be used in the analysis method of the present invention.

Thus, the present invention also relates to a method for monitoring and/or assessing the quality and/or stability of a formulation, e.g. during one or more of manufacture, storage and use. The invention also relates to a method of quality control of a formulation, e.g. to assess that the formulation meets product specifications as further described herein. The invention in any of these aspects comprises one or more selected from the comparison with one or more reference samples, the analysis of batch to batch variation, and the ongoing monitoring of a production process.

The present invention relates to any product that is associated with the formulations of the present invention, e.g. by comprising them, or by being necessary for their production or confectioning, without any limitations.

For example, the present invention relates to an article of manufacture, e.g. a sealed container comprising one or more of the formulations according to the present invention. The invention also relates to a pharmaceutical unit dosage form, e.g. a dosage form suitable for parenteral administration to a patient, preferably a human patient, comprising one or more of the formulation according to any embodiment described herein. The dosage unit form can be e.g. in the format of a prefilled syringe, an ampoule, cartridge or a vial. The syringe, ampoule, cartridge or vial can be manufactured of any suitable material, such as glass or plastic and may include rubber materials, such as rubber stoppers for vials and rubber plungers and rubber seals for syringes and cartridges. The invention also relates to a kit comprising one or more of the formulations according to the present invention. The kit may further comprise instructions for use and/or a clinical package leaflet. In any embodiment of the products as defined herein, the invention also encompasses the presence of packaging material, instructions for use, and/or clinical package leaflets, e.g. as required by regulatory aspects.

DEFINITIONS

Identity

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two or more amino acid sequences may be calculated using a known computer algorithm for sequence alignment such as NCBI Blast v2.0. using standard settings.

Some other techniques, computer algorithms and settings for determining the degree of sequence identity are for example described in WO04/037999, EP0967284, EP1085089, WO00/55318, WO00/78972, WO98/49185 and GB2357768-A.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO04/037999, GB2357768-A, WO98/49185, WO00/46383 and WO01/09300; and (preferred) types and/or combinations of such substitutions may be selected on the basis of the pertinent teachings from WO04/037999 as well as WO98/49185 and from the further references cited therein. Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies® is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Nature Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

Abbreviations

API Active Pharmaceutical Ingredient
cIEF Capillary IsoElectric Focusing
DLS Dynamic Light Scattering
DOE Design of Experiments
DP Drug Product
DS Drug Substance
FT Freeze-Thaw
HMW High Molecular Weight
LMW Low Molecular Weight
MALS Multi-Angle Light Scattering
RH Relative Humidity
RPC Reverse Phase Chromatography
RP-HPLC Reverse Phase High Performance Liquid Chromatography
SE-HPLC Size Exclusion High Performance Liquid Chromatography
SOP Standard Operating Procedure
Tm Melting Temperature (° C.)
TSA Thermal Shift Assay
vWF von Willebrand Factor
WFI Water For Injection The invention will now be further described by means of the following non-limiting preferred aspects, examples and figures:

The entire contents of all of the references (including literature references, issued patents, published patent applications, and co pending patent applications) cited throughout this application are hereby expressly incorporated by reference, in particular for the teaching that is referenced hereinabove.

EXAMPLES

A set of experiments was designed in order to obtain an improved formulation buffer, intended to satisfy a broad range of different and seemingly incongruous objectives. In particular, exemplary formulations are provided herein which are capable of maintaining the stability, biological activity, purity and quality of ALX-0081 and this over an extended period of time, stable to various stresses such as freezing, lyophilization, heat and/or reconstitution.

Contemporaneous ALX-0081 DS has been presented as a liquid formulation containing 5 mg/mL of the active pharmaceutical ingredient (API) in a phosphate-based (D-PBS)

buffer containing 200 mM glycine and 0.02% Tween-80 (v/v), pH 7.1 (DS). Although this formulation has been applied during initial clinical trials, it may be improved in several manners. First, the relatively low concentration would probably necessitate multiple subcutaneous injections (assuming the volume per subcutaneous injection is restricted to about 1 mL) thus reducing patient usage friendliness. Secondly, the storage stability at 3-8° C. or room temperature of the current formulation of ALX-0081 is limited. The limited shelf-life in the present formulation is mainly determined by chemical modification (cf. Section 7.2). Chemical modifications may be linked with potency loss. Although a practicable shelf-life can be achieved by storing the product at −20° C., this is, however, not considered to be a favourable option for most practical purposes.

Methods

Samples were analyzed essentially according to standard operating procedures for assessing content, potency and purity, precipitation, concentration, degradation, aggregation and potency. In addition, all samples were visually inspected for turbidity or the presence of protein aggregates or precipitation. The residual moisture content of specific lyophilized samples was determined by means of Karl-Fischer titration.

Three different lyophilization programs were used in the present study to freeze-dry ALX-0081—a standard 65 h run (FIG. 1), a shortened 37 h run and a longer lyophilization cycle of 66 h optimized to reduce residual moisture content as described in Table 14.

Briefly, at the start of the shortened 37 h lyophilization process the shelf temperature was +20° C. and was brought to −50° C. in 2 hours. Next, a vacuum of 0.04 mbar was created in 1 hour. After reaching the vacuum of 0.04 mbar the shelf temperature was kept at −50° C. for 4 hours. After these 4 hours the temperature was gradually increased to 0° C. in 15 hours (i.e. primary drying step, removing frozen water). The shelf temperature of 0° C. was kept for 7 hours while keeping a vacuum of 0.04 mbar. After 7 hours the temperature was raised to +25° C. in 3 hours and subsequently kept at 25° C. for 5 hours (i.e. secondary drying step, removing unfrozen water). The vials were closed under a vacuum of ±0.400 mbar after which normal pressure was restored.

The same method was applied for the standard 65 h run and only differs in the second drying step which was prolonged with 28 h at +25° C. under vacuum resulting in a total cycle time of about 65 h. A schematic overview of the different steps in the standard 65 h lyophilization run is shown in FIG. 1. During the lyophilisation process, product temperature of three vials in strategic positions were monitored. Finally, the standard 65 h run was modified during the run according to the reading of the temperature probes resulting in a prolonged lyophilization cycles as described in Table 14.

Chemical Stability of Contemporaneous ALX-0081 Formulation

RP-HPLC is one of the most informative methods to assess the chemical stability of a drug substance (DS).

RP-HPLC resolved the ALX-0081 DS into a number of different species. In addition to the main peak, pre-peaks (substance eluting before the intact unmodified material) and a number of post-peaks could be discerned. In the batches produced so far, the pre-peaks and post-peak 1 consistently represented about 2% and 3.6% of the DS respectively, whereas the other post-peaks accounted for less than 1% of the DS.

Figure 2A:
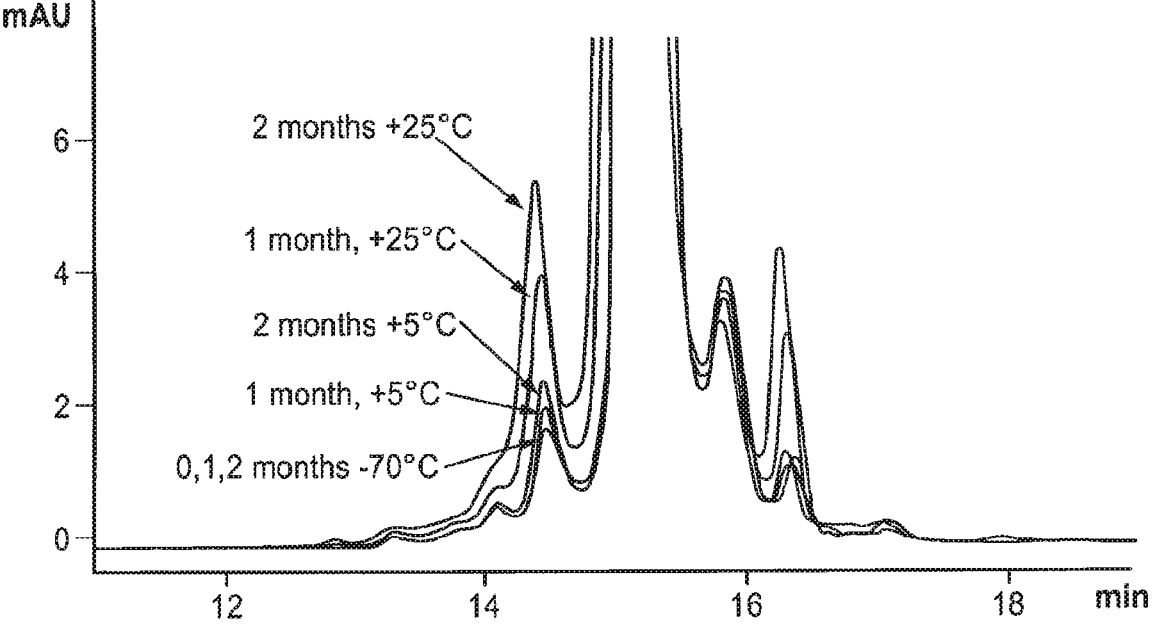
FIG. 2A Relevant part of the RP-HPLC chromatograms of ALX-0081 after 1 and 2 months storage at −70° C., +5° C. and +25° C.; mAU: milli absorbance unit.
Figure 2B:
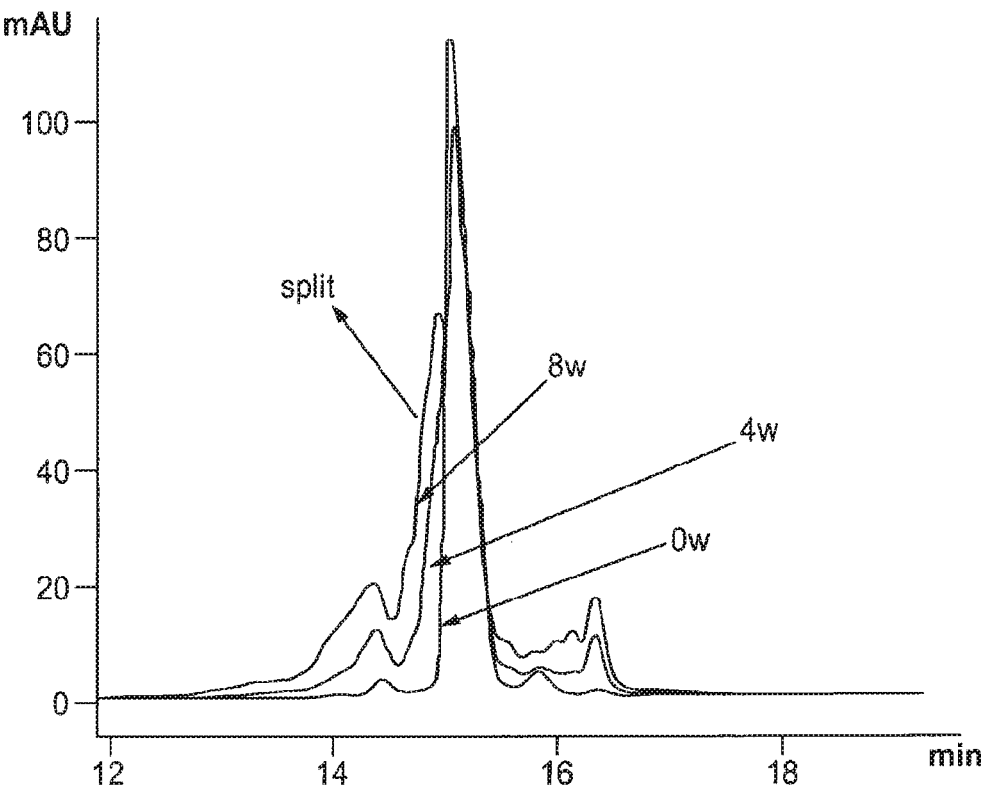
FIG. 2B Zoom of relevant part of the RP-HPLC chromatograms of ALX-0081 after 0, 4 and 8 weeks incubation at 37° C. Splitting of the RP-HPLC main peak is observed as a result of prolonged incubation at 37° C. (0, 4, 8w); mAU: milli absorbance unit.

During storage under accelerated (+5° C.) or stressed (+25° C. and +37° C./+40° C.) conditions however, the relative abundance of certain product related variants increased with time and temperature, as depicted in FIG. 2A. Additionally, the RP-HPLC main peak appears to divide into several different species upon prolonged incubation, especially at elevated temperatures (≥25° C.) (FIG. 2B). The data indicate that some earlier eluting new molecular species are generated during storage.

The most important modifications which were present in ALX-0081 DS at the time of manufacturing or which arose during storage are the following: (i) pre-peak 1 (oxidation); (ii) post-peak 1 (nor-leu variant); (iii) post-peak 2 (formation of pyroglutamate), and (iv) splitting of the main peak (isomerization). The modifications (i), (ii), and (iii) did not significantly affect the potency (data not shown). In contrast, the isomerization of the aspartic acid residues at position 105 and 236 of SEQ ID NO: 1, which are located in the CDR3 region, were shown to be the predominant molecular mechanism underlying a potential loss of potency of ALX-0081 (cf. (iv) above).

Some of the ALX-0081 product related variants, present at the time of manufacturing or arising during storage, could also be detected by cIEF. This was the case for the pyroglutamate modification which appeared as a post-peak (cf. (iii) above). Also, similar to what was observed in the RP-HPLC analysis, the isomerization events at position 105 in both 12A02H1 domains resulted in main peak broadening and eventually splitting of the main cIEF peak (cf. (iv) above).

Buffer and Excipient Screening

In order to further develop the formulation of vWF binders, a complex set of experiments was designed elaborating various parameters which all influence each other, including (i) different buffers, (ii) at different concentrations, (iii) each buffer at various pH; and (iv) each combined with different excipients.

Buffer systems should have an as low buffering capacity as feasible, so as not to significantly disturb the body's buffering system when injected. In addition, the buffer type and concentration on the activity of the active pharmaceutical ingredient (API) must be evaluated very carefully.

Generally, increased levels of protein stability have been attributed to high melting temperatures. Accordingly, thermal properties of ALX-0081 were monitored in the presence of various compositions. In particular, a TSA experiment was performed in 192 different isotonic formulations, for which the results were fed into a design of experiments (DOE) to evaluate the effect of buffer, concentration, ionic strength, pH and excipients on the thermal stability of ALX-0081. The read-out was the melting temperature (Tm) of ALX-0081 which is indicative for the thermal stability of the protein in the various tested compositions.

Briefly, the employed thermal shift assay (TSA) follows the signal changes of a fluorescence dye, such as Sypro Orange, while the protein undergoes thermal unfolding. When Sypro Orange is added to a properly folded protein solution, it cannot bind to any surface on the protein and its fluorescence signal is quenched. When the temperature rises, the protein undergoes thermal unfolding and exposes its hydrophobic core region. Sypro Orange then binds to the hydrophobic regions and unquenches, which results in the increase of the fluorescence signal. The assay was performed on solutions containing different formulations to be tested, ALX-0081 at 0.2 mg/mL and 10× Sypro Orange. The program consisted of the following steps: heat to 37° C. at a ramp rate of 4.4° C./s and hold for 10 s; heat to 90° C. at a continuous ramp rate of 0.02° C./s (20 acquisitions per ° C.); and cool to 37° C. at a ramp rate of 2.2° C./s and hold for 10 s.

The following set of buffers with varying concentrations (10-200 mM), pH values and excipients were herein explored:

| | |
|---|---|
| citrate | pH 6.0-6.5-7.0 |
| histidine | pH 5.5-6.0-6.5 |
| phosphate | pH 6.5-7.0-7.5 |
| Tris-HCl | pH 7.4-7.7-8.0 |
| NaCl | 0-140 mM concentration range |
| glycine | 0-270 mM concentration range |
| mannitol | 0-270 mM concentration range |
| sucrose | 0-270 mM concentration range |
| trehalose | 0-270 mM concentration range |

The obtained melting temperatures (Tm) were imported in the Design Expert program for analysis of the factorial screening experiment to predict 50 formulations resulting in the highest thermal stability (see Table 1).

The highest Tm values were predicted for phosphate (pH 7.0-7.5) and citrate (pH 6.2-7.0) containing trehalose, sucrose, mannitol or glycine. Wholly unexpectedly, the results of the study suggest that Tris-HCl (pH 7.8-8.0) and histidine-HCl (pH 6.5) based buffers return significantly lower melting temperatures, although they were previously elected as the buffer system of choice for controlling solution pH of immunoglobulin single variable domains as described in WO2010/077422.

Accordingly, it was concluded that phosphate and citrate formulations containing trehalose, sucrose, glycine or mannitol, performed especially well in stabilizing vWF binders, e.g. ALX-0081.

Solubility Testing

In order to evaluate whether the solubility of ALX-0081 could be further enhanced, an initial screening was performed in several formulations. ALX-0081 was buffer exchanged to the formulation of interest (excluding Tween-80) and further concentrated in a stirring cell (e.g. type Amicon) equipped with 5 kDa cut off filter. As soon as visible precipitation or turbidity occurred, the sample was filtered and the protein concentration was measured. Table 2 shows a summary of the obtained results.

Figure 3A:
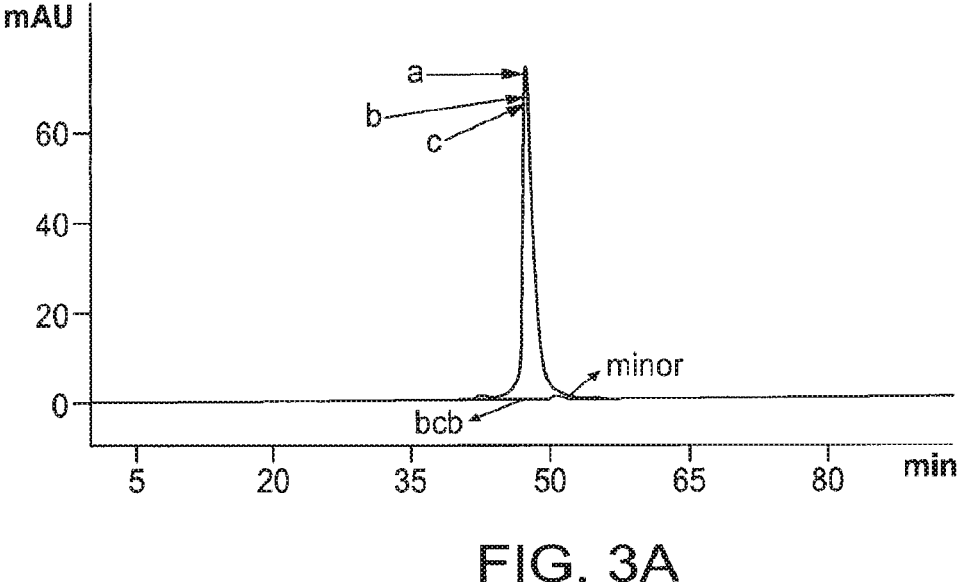
FIG. 3A Overlay of SE-HPLC profiles of blank citrate buffer (bcb) and ALX-0081 in 20 mM citrate pH 7.0 at 55.9 mg/mL before (a) and after 10 freeze-thaw (FT) cycles at −20° C. (c) and −70° C. (b) (λ=280 nm). A minor citrate peak was observed for samples pre-diluted in running buffer; mAU: milli absorbance unit.
Figure 3B:
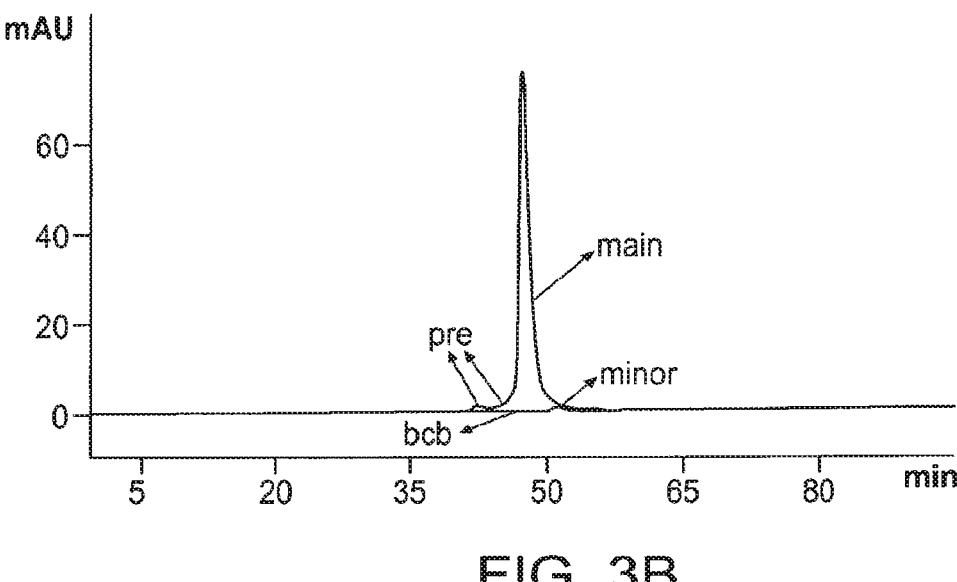
FIG. 3B Overlay of SE-HPLC profiles of blank citrate buffer (bcb) and ALX-0081 in 20 mM citrate pH 7.0 at 55.9 mg/mL after ±1 week storage at +4° C. (λ=280 nm). ALX-0081 was resolved into one main peak (97%) corresponding with intact, unmodified ALX-0081 and small pre peaks representing only 3% of the total surface area. A minor citrate peak was observed for ALX-0081 pre-diluted in 5 running buffer; mAU: milli absorbance unit.

Concentration in phosphate and histidine based buffers resulted in sample turbidity and formation of precipitation at relatively low protein concentrations (<10 mg/mL). In contrast, ALX-0081 remained physically stable in citrate buffer, even after reaching a concentration of ~56 mg/mL. In addition to the visual inspection, the absence of particulate matter or HMW species was confirmed by fluorescence microscopy (staining with Nile Red, by SE-HPLC and DLS). Furthermore, subjecting the ~56 mg/mL solution to either 10 FT cycles at −20° C. or −70° C., or storage at +4° C. for about 1 week did not appear to affect the physical stability of the molecule as evidenced by SE-HPLC analysis (see FIGS. 3A and 3B respectively).

The comparatively high solubility of ALX-0081 in the citrate buffer was corroborated by a PEG precipitation assay (data not shown).

Tween-80

In order to determine whether the non-ionic surfactant polysorbate, also designated Tween, (Polyoxyethylene (N) sorbitan monolaurate; wherein N=20, 40, 60, 65, 80 or 85)

is required in the formulation of ALX-0081, several stir stress experiments were performed in 50 mM citrate buffer at pH 6.0 and 6.5. The effect of different concentrations of Tween-80 (no Tween-80 vs. 0.01% vs. 0.02% (v/v)) on the physical stability of ALX-0081 was evaluated at 5 mg/mL by monitoring 500 nm scatter signal in a spectrofluorometer.

Tween-80 prevented an increase in the scatter signal in both buffers demonstrating its protective effect (FIGS. 4A and 4B). No significant differences were observed between samples containing 0.01% or 0.02% Tween-80 (v/v). Furthermore, the SE-HPLC profiles of samples before and after stirring did not show any differences: 95-100% recovery was achieved and no oligomerization or degradation could be detected.

Based on these results, it was decided to include 0.01% Tween-80 (v/v) in the formulation of vWF binders, e.g. ALX-0081.

Tween

In order to determine whether the other members in the polysorbate range, which differ by the length of the poly-oxyethylene chain and the fatty acid ester moiety, e.g. Tween-20, Tween-40, Tween-60, Tween-65 and Tween-85 are required in the formulation of anti-vWF binders, several stir stress experiments are performed in 50 mM citrate buffer at pH 6.0 and 6.5, essentially as described in Section 7.5 above. The effect of different concentrations of the various Tween-members (no Tween vs. 0.01% vs. 0.02% (v/v)) on the physical stability of the vWF binder is evaluated at 5 mg/mL by monitoring 500 nm scatter signal in a spectrofluorometer.

Tween-20, Tween-40, Tween-60, Tween-65 and Tween-85 give substantially the same beneficial result as Tween-80.

Stability Testing of Liquid Formulations

A more comprehensive study was performed to assess the stability of ALX-0081 in different citrate-based isotonic formulations at a concentration of 20 mg/mL. Table 3 gives an overview of the different formulations which were tested.

The main goal was to evaluate the effect of pH (6.0-6.5-7.0) and excipient type (NaCl, mannitol, sucrose or glycine) on the stability of the liquid product. For control and direct comparison purposes the study also included contemporaneous ALX-0081 formulated at 5 mg/mL in D-PBS and glycine (identical to current formulation, except for the lower Tween-80 concentration) as well as the previously mentioned different citrate-based isotonic ALX-0081 solutions but formulated at a concentration of 5 mg/mL instead of 20 mg/mL. Altogether, this resulted in 17 different liquid formulations (formulation no. 1-17) which were subjected to profound stability studies. In order to exclude the effect of differences in Tween concentration, all formulations contained 0.01% Tween-80 (v/v).

Freeze-Thaw Stability

The effect of repetitive FT cycles on the stability of ALX-0081 as a liquid formulation was evaluated. Aliquots of the different formulations (0.5 mL/tube) were subjected to up to 10 FT cycles at −70° C. or −20° C. One cycle included freezing for ±20 min followed by thawing during 5 min in a water bath at +25° C. After this treatment, all formulations remained visibly clear. RP-HPLC analyses showed good recovery (95-100%) and no significant difference in profile could be detected suggesting that the quality of vWF binders, e.g. ALX-0081 is not affected by repeated freeze-thawing in the 17 different liquid formulations tested.

Storage Stability

The stability of the 17 different formulations was also assessed by storing aliquots (0.5 mL/tube) under stressed conditions, i.e. +40° C.; the −70° C. long term storage condition was included as reference. The analyses focused on RP-HPLC because this method is generally known as a particularly informative method for revealing chemical modifications that occur during storage (see Table 4). This section gives an overview of the data obtained after 1 month storage; the results confirm the findings at the earlier time points, i.e. after 1 week and 2 weeks.

(a) RP-HPLC

As previously indicated in Section 7.2 above, RP-HPLC analysis resolved contemporaneous ALX-0081 DS (D-PBS/glycine formulation) into some product related variants and impurities. Briefly, under stressed conditions (e.g. +40° C.), the purity (% main peak) decreased concomitantly with an increase in some of the existing pre/post-peaks as well as the formation of additional ones.

The RP-HPLC data obtained in the present study are summarized in Table 5.

Overall, the obtained results indicated that essentially the same modifications took place in the different citrate buffers as observed in the present formulation buffer (i.e. D-PBS/glycine), although some differences in relative peak area could be observed. In particular, the increase in pre-peak area (oxidation) was slower in the citrate formulations (especially at pH 6.0) compared to the D-PBS/glycine formulation. With respect to this pre-peak build up, glycine appeared to be the least favorable amongst the different excipients. The profile of the different post-peaks after storage for 1 month at +40° C. was comparable for all formulations, although the second post peak (i.e. the pyro-glutamate variant) appeared to be more pronounced at pH 7.0 than at pH 6.0-6.5. The extent of broadening/splitting of the main peak—the result of asp isomerization—is difficult to quantify due to poor resolution; the area percentage of the shoulder peak could not be accurately estimated and was therefore included in the relative surface area reported in Table 5 for the main peak. Nonetheless, the corresponding RP-HPLC chromatograms (data not shown) allowed making a qualitative assessment; these data suggest that the extent of isomerization is quite similar in the various formulations.

(b) cIEF

Similar to RP-HPLC, the cIEF method permits the detection of certain product variants that occur during storage under stressed conditions (see Section 7.2 for details). This is exemplified in FIG. 5, comparing the electropherograms of contemporaneous ALX-0081 after storage during one month at −70° C. and +40° C.

The cIEF data obtained in the present study (data not shown) basically confirm the conclusions reached by the RP-HPLC analysis, i.e. the same type of modifications take place to roughly the same extent in the different citrate buffers as observed in the present formulation buffer, represented herein by formulation 17 as depicted in FIG. 5 (i.e. D-PBS/glycine). However, some differences in relative peak area could be observed. In particular, the post peak (i.e. the pyroglutamate variant) appeared to be more pronounced at pH 7.0 than at pH 6.0-6.5, which is in agreement with the findings by RP-HPLC as previously summarized in Table 5.

(c) SE-HPLC

SE-HPLC analysis was performed to examine the physical stability of ALX-0081, i.e. to detect HMW species and/or degradation products that could have formed during storage under stressed conditions. For all of the formulations which were tested here, the stress test did not appear to have a significant effect on the SE-HPLC chromatograms.

(d) Conclusion

A summary of the most important findings regarding the storage stability of the different liquid ALX-0081 formulations is shown in Table 5. Only the most informative data based on RP-HPLC analysis were listed. These data suggest a higher chemical stability in 50 mM citrate at pH 6.0-6.5. With the exception of glycine, the type of excipient did not have a significant effect on stability. With respect to the physical stability, no differences could be observed between the different formulations. The latter was evidenced by the ±100% recovery observed for all samples in the various HPLC analyses as well as by the SE-HPLC chromatograms demonstrating the absence of aggregation/degradation. Based on the above results, it was decided to further explore the potential of the citrate/sucrose formulations at pH 6.0-6.5.

Stability Testing of Lyophilized Formulations

The effect of lyophilization was assessed by comparing the storage stability of ALX-0081 in liquid and lyophilized citrate/sucrose formulations (20 mg/mL API at pH 6.0-6.5). An overview of the formulations tested is given in Table 6. The prior art D-PBS/glycine based formulation (5 mg/mL API) was included for comparison. Liquid (i.e. prior to lyophilization) and lyophilized ALX-0081 were kept frozen (−70° C. for the liquid samples and −20° C. for the lyophilized formulations) as well as at +5° C., +25° C. and +40° C. and samples were analyzed after 2 weeks and 1.5 months storage.

FIG. 6A shows a picture of the vials after the lyophilization process using the standard 65 h run as depicted in FIG. 1. Lyophilization of the formulations containing citrate/sucrose resulted in good cake formation, whereas samples formulated in D-PBS/glycine did not produce a decent cake. All samples could readily be resolubilized with Milli-Q water and solutions were clear and colorless (FIG. 6B).

Evaluation of Product Before and After Lyophilization

RP-HPLC and SE-HPLC analysis revealed no significant differences in terms of physicochemical characteristics between the liquid starting product (kept at ≤−70° C.) and the product after lyophilization and reconstitution for any of the tested formulations. Furthermore, full sample recovery was demonstrated for all formulations (Table 7).

Evaluation of Lyophilized Product After 1.5 Month Storage (a) Visual Inspection and Content The cake of the lyophilized samples showed no visual signs of decay after 1.5 month storage at −20° C., +5° C., +25° C. or +40° C.

Samples were clear and colorless after reconstitution with Milli-Q water. Also, storage did not have a significant effect on content, measured after reconstitution (Table 8).

(b) RP-HPLC

The profiles of the 3 different lyophilized formulations (no 3, 7 and 17) were compared after 1.5 months storage at −20° C., +5° C., +25° C. and +40° C. respectively. A comparison at the most strenuous conditions (+40° C.) best reveals the impact of the lyophilization on the chemical stability. Corresponding results are summarized in Table 8. As can be seen, storage in the frozen form does not appear to affect ALX-0081 in any of the formulations tested in the present study.

Overall, the prevailing conclusion from the obtained data is that lyophilization of a citrate/sucrose based formulation essentially prevents the chemical modifications that occur in the liquid form, with the exception of some minor amounts of pyroglutamate modification. In these lyophilized formulations, there was neither an increase in the area percentage of the pre-peaks nor a sign of main peak broadening/splitting. In contrast, lyophilization of the D-PBS/glycine based formulation did not result in a significant improvement of the chemical stability. The pyroglutamate formation in the citrate/sucrose lyophilized formulation appeared to be slightly more pronounced at pH 6.0 than at pH 6.5. This is substantiated by the data at +25° C., at which temperature the rate of pyroglutamate formation is lower but shows the same pH dependence. As expected, storage for up to 1.5 months at −20° C. or +5° C. did not cause any detectable deterioration of lyophilized ALX-0081 (data not shown).

Surprisingly, at +40° C. improved stability was obtained in the citrate/sucrose based formulations compared to the formulation based on D-PBS/glycine, the latter showing significantly higher susceptibility to chemical modifications.

For the liquid formulations, storage of up to 1.5 months at −70° C., +5° C. and +25° C. did not have a significant effect on ALX-0081 (data not shown). The deterioration observed after 1.5 months of storage at +40° C., is roughly in agreement with earlier observations (see Section 7.7.2).

(c) cIEF

The results obtained by cIEF analysis are in agreement with those of RP-HPLC. Most notably, lyophilization of a citrate/sucrose based formulation is not able to prevent the pyroglutamate modification completely. Indeed, storing the lyophilized product at +40° C. for 1.5 months resulted in an increase in the post peak. Again, faster pyroglutamate formation was observed in citrate/sucrose at pH 6.0 than at pH 6.5.

(d) SE-HPLC/MALS/DLS

Storage for up to 1.5 months at −70° C./−20° C., +5° C. and +25° C. did not have an effect on the SE-HPLC profiles of lyophilized or liquid formulations of ALX-0081 (data not shown). However, at +40° C. peak broadening and formation of shoulder peaks could be observed in all liquid formulations. MALS analysis showed that these shoulder peaks correspond to monomeric ALX-0081 (data not shown). The data hint at a conformational change in a subpopulation of ALX-0081 as a result of the stressed storage. Surprisingly, the SE-HPLC profile of lyophilized citrate/sucrose formulations was not affected by the +40° C. stress test indicating that these lyophilized formulations also improve the physical stability of ALX-0081. This however was not the case for the lyophilized D-PBS/glycine formulation; stressing this formulation at +40° C. not only resulted in a shoulder peak but apparently also in some higher molecular weight species, visible as a broad pre-peak (Table 8). DLS analysis did not detect any large oligomeric species in any of the formulations (data not shown).

(e) Conclusion

A summary of the most important findings regarding the storage stability of the tested lyophilized ALX-0081 formulations is shown in Table 8. Overall, only limited differences in stability were observed between the citrate/sucrose formulations, although unexpectedly ALX-0081 appeared to be less prone to pyroglutamate formation at pH 6.5 than at pH 6.0. Therefore, further reformulation work for ALX-0081 was focused on citrate/sucrose based formulations at pH 6.5.

Further Optimization of the Citrate/Sucrose Based Formulation

The data collected so far show that a citrate/sucrose based formulation improves the solubility and that lyophilization of this formulation dramatically improves the storage stability of ALX-0081. However, storage of lyophilized ALX-0081 at higher temperatures, albeit limited, still results in pyroglutamate formation. It is reasonable to assume that this modification may limit the shelf-life of the lyophilized product (even when stored at +5° C.). It remains to be elucidated why lyophilization was not able to prevent this modification.

It was hypothesized that water remaining in the freeze-dried product plays a key role.

If this hypothesis would be true, then the remaining water may be minimized by optimizing the physical lyophilization parameters, such as drying time, temperatures, vacuum etc., as listed above, but at the same time the other parameters of the vWF binder should remain constant. Another approach is modifying the formulation, but again at the same time the other parameters of the vWF binder should remain constant. In addition, adjusting the physical lyophilization parameters in combination with modifying the formulation may be used.

Optimizing Lyophilization Parameters

Optimizing the physical lyophilization parameters, including (i) drying time times, (ii) temperatures of the different steps, (iii), vacuum, and a combination of (i)-(iii) was not satisfactory, i.e. no or inadequate effect on residual moisture content or affecting the parameters of the vWF binders.

Optimizing Formulation for Lyophilization

The effect of moisture content on the chemical stability of the lyophilized product was investigated by adjusting the concentrations of the citrate buffer and the sucrose excipient. In addition, a secondary drying time during the lyophilization program was investigated.

Effect of Moisture Content on Stability of Lyophilized Product

Three different isotonic formulations of ALX-0081 with varying citrate and sucrose concentrations (all three at pH 6.5) were subjected to two different lyophilization programs: the standard 65 h run on the one hand and a shortened 37 h run on the other hand. An overview of the formulations tested is given in Table 9. FIG. 7 shows the vials obtained after lyophilization. Lyophilization resulted in good cake formation for all formulations.

Lyophilized samples of ALX-0081 were analyzed after 2 and 4 weeks of storage at both −20° C. and +40° C. In the present experiment, it was decided to perform an exhaustive testing so as to further substantiate the usefulness of the formulations.

First, during storage at +40° C. for up to 4 weeks the cake of the lyophilized samples remained intact and reconstitution yielded clear solutions. The lyophilization cycle appeared to have no significant effect on content (measured spectrophometrically at 277 nm) or osmolality. In agreement with earlier experiments, 4 weeks storage at +40° C. did not have an effect on the physical stability of ALX-0081, based on SE-HPLC, MALS, and DLS analyses (data not shown). Additionally, it was found that the potency of ALX-0081 as determined by the Biacore-based assay was unaffected by the lyophilization process and the subsequent storage (data not shown). However, the RP-HPLC analyses demonstrated that storage did again result in the formation of—albeit minor—quantities of the pyroglutamate variant. This was slightly more pronounced for the formulation containing the highest concentration of citrate and lowest concentration of sucrose (Table 10). In addition, for each lyophilized formulation, the total moisture content was determined by means of Karl Fisher titration. A summary of these data together with the amount of pyroglutamate detected in the corresponding stressed samples is shown in Table 10. It appears from the data obtained for each lyophilization program separately that a higher moisture content results in a higher susceptibility to pyroglutamate formation. This suggests that residual water present in the lyophilized product promotes chemical modifications.

In conclusion, the results indicate that reducing the moisture content of lyophilized vWF binders, e.g. ALX-0081, is beneficial for its chemical stability.

Effect of Reducing Buffer Strength and Increasing Sucrose Content

The data obtained in the previous section show that reducing the citrate concentration while increasing the sucrose concentration (thereby maintaining an isotonic solution) is beneficial for the stability of the lyophilized product. At the same time, evidence was obtained that ALX-0081 required a sufficiently high concentration of citrate to obtain improved solubility. It was therefore decided to assess the effect of the citrate and sucrose concentrations on the appearance of the solution during storage at +5° C. and +25° C., and to re-evaluate the freeze-thaw stability in the presence of lower concentrations of citrate.

Assessing Impact of Citrate/Sucrose Concentration

In a first experiment, 12 different formulations of ALX-0081 were stored at +5° C. and +25° C. for up to 4 days. Samples were inspected on a regular basis for turbidity or presence of precipitate. Pictures taken of the samples after 4 days of storage are shown in FIGS. 8A, 8B, 9A and 9B. An overview of the different formulations and corresponding results is presented in Table 11. After 4 days of storage at +25° C. all samples remained clear and colorless (FIG. 8A). In contrast, at +5° C. most citrate formulations without excipients became hazy (FIG. 8B). Clearly, the degree of haziness is inversely proportional to the citrate concentration, with the formulation of 50 mM citrate remaining clear. Also, sample recovery for the sample containing 15 mM citrate was 68% (based on A277 after 20 h storage), while other recoveries varied from 90 to 100% (data not shown). Adding sucrose to the 15 mM citrate formulation prevented sample haziness, although at the lowest concentration of sucrose (i.e. 5%) some minor turbidity was detected at +5° C. (FIG. 9B).

The observations confirm the importance of a sufficiently high concentration of citrate in maintaining ALX-0081 soluble, particularly at low temperature. Nevertheless, increasing the citrate concentration resulted in increased moisture content. Unexpectedly, reducing the citrate concentration can be compensated for by the addition of sucrose. No effect of Tween-80 on solubility was observed.

Assessing FT Stability

A follow-up experiment focused on the FT stability of several citrate/sucrose based formulations. Nine different formulations of ALX-0081 were subjected to 5 consecutive FT cycles at −20° C. An overview of the tested formulations and corresponding results is shown in Table 12. All samples remained clear and FT cycles did not affect the physical stability of vWF binders, e.g. ALX-0081, based on content analysis and the SE-HPLC data.

Optimizing Sucrose and Citrate Concentration in View of Isotonicity

Based on the above mentioned storage and FT results the optimal concentration of citrate buffer was selected as 20 mM. A final experiment was performed on three formulations differing in sucrose concentration. The aim of this experiment was to establish the optimal sucrose concentration for achieving an isotonic formula and to confirm FT stability of ALX-0081 at 20 mg/mL. In addition to 5 consecutive FT cycles, each formulation was also subjected to 1 FT cycle followed by 24 h storage at +25° C. and an additional FT cycle in order to mimic the handling steps during manufacturing.

A summary of the results is given in Table 13. All tested formulations were clear and the various handlings did not have an effect on content/recovery or osmolality. Based on the osmolality values it seems that a concentration of 7% sucrose is optimal to obtain an isotonic solution.

Stability Study of Lyophilized ALX-0081 Formulations Stored at Various Temperatures for Up to 12 Months ALX-0081 formulated at 12.5 mg/mL in 20 mM citrate buffer pH 6.5, 7% sucrose (w/v) and 0.01% Tween-80 (v/v) was lyophilized according to the conditions set out in Table 14. Samples were subsequently stored at –20° C. (±5° C.), +5° C. (±3° C.), +25° C. (±2° C./60±5% RH) and +40° C. (±2° C./75±5% RH).

The stability of the lyophilized formulations was assessed at different timepoints, i.e. initial, 1 month, 3 months, 6 months, 9 months and 12 months, and was evaluated for purity, appearance, physicochemical properties and potency.

Detailed sample characterization data are provided in Tables 15 to 23.

Purity of the samples was assessed by RP-HPLC in which the percentage of mean peak area was determined as well as the percentage of pre-and post-peak areas. The protein concentration was determined by UV absorbance.

Further, the lyophilized samples were visually inspected, reconstituted, and the reconstituted formulation was visually inspected. The pH of the samples after reconstitution was measured and the moisture content of the lyophilized powder was determined by coulometric titration (Karl Fischer). Particulate matter count measurements were performed to count particles ≥10 μm and 25 μm. The samples were further characterized for biological function using a biacore-based assay. Potency was expressed as percent relative potency of reference material.

The obtained stability data show that the characteristics of the lyophilized ALX-0081 product are not significantly affected by 12 months storage at either –20° C. or +5° C. The data collected throughout the stability study at those temperatures were found to be comparable to those generated at time zero.

Several minor changes were observed for samples stored at +25° C. or +40° C. which can be attributed to the accelerated or stressed storage conditions. The main observations were:

At +25° C. and at +40° C. an increase in post peak 2 was observed on RP-HPLC during the 12 months storage, corresponding with the formation of the pyroglutamate variant from 0.7% to 1.1% or to 2.4% respectively.

At +40° C. an increase in moisture content from 0.7% to 2.1% (w/w) after 12 months storage was noted. This could potentially be attributed to intake of moisture from the storage environment (i.e. 75% RH) by the stopper, with the subsequent gradual diffusion to the product.

The results obtained under stressed conditions suggest a correlation between the moisture content and the chemical stability of the product; this corresponds with the data previously reported under Section 7.10.

Hence, these data indicate the importance of controlling the moisture content of the DP product during storage.

Considering that +40° C. storage can be regarded predictive for the long term stability at +25° C., the 12-month stability data included herein provide a good indication for long term storage stability at room temperature (such as 18, 24, 30 or 36 months) and even prolonged stabilities when stored under milder conditions (e.g. +5° C. or frozen).

In Vitro Comparability Study on the Biological Activity of the Liquid and Lyophilized Drug Product Formulation of the Anti-vWF Nanobody Caplacizumab (ALX-0081)

Objective

A number of assays were used to evaluate the in vitro comparability of contemporaneous ALX-0081 DP [liquid formulation containing 5 mg/mL of the active pharmaceutical ingredient (API) in a phosphate-based (D-PBS) buffer containing 200 mM glycine and 0.02% Tween-80 (v/v), pH 7.1] and the lyophilized ALX-0081 DP formulation as presented above [formulated at 12.5 mg/mL in 20 mM citrate buffer pH 6.5, 7% sucrose (w/v) and 0.01% Tween-80 (v/v)] with regard to biological activity and target binding:

a) Biacore-based potency assay b) ELISA-based potency assay c) Ristocetin Induced Cofactor Activity (RICO) pharmacodynamic biomarker assay d) Gyrolab-based affinity determination These assays allowed a side-by-side comparison of the liquid and lyophilized drug product of ALX-0081 (caplacizumab). Predefined comparability criteria were used to evaluate comparability for each assay, and are listed in Table 24.

Methods a) The Biacore assay is based on the surface plasmon resonance (SPR) technology, and measures avid binding of ALX-0081 to human vWF A1-domain immobilized on a sensor chip. The assay has been selected for potency testing at release and on stability.

b) The ELISA-based potency assay is an orthogonal method for potency testing of ALX-0081 that has been developed for further characterisation of the target neutralisation capacity of caplacizumab. This assay measures the inhibition of ristocetin-induced binding of von Willebrand Factor (vWF) to bound platelet by caplacizumab.

c) The RICO assay is used as pharmacodynamics marker for the pharmacological activity of caplacizumab. The assay measures the rate and degree to which human lyophilized platelets form aggregates after the addition of the antibiotic ristocetin, which mimics shear-induced activation of vWF.

d) Gyrolab-based assay analyses the kinetic interactions of caplacizumab with its multimeric target vWF and determines the affinity constant of caplacizumab to human multimeric vWF. Briefly, affinity determination on the Gyroloab platform was established as follows: Gyrolab Bioaffy 1000 CDs were used. As capture tool, 3000 nM in-house biotinylated purified vWF (purified HaemateP using size-exclusion chromatography) was applied on the columns which were pre-packed with streptavidin-coated beads. Filter-sterilized D-PBS containing 0.01% Tween-20 was used for dilution of the capture tool. A 1/3 dilution series of purified vWF HaemateP was pre-incubated for 24 hours at RT (+20° C.) in a 96-well plate on a rotor at 600 rpm with a fixed concentration of caplacizumab (5 pM) in AD1 buffer (Assay Diluent buffer for dose response curve). After 24 hours, the plate was centrifuged for 1 min at 200 g. 70 μL of the pre-incubation mixture, containing the free caplacizumab molecules, was brought into a deep well PCR plate. Then, this mixture was flowed over the column so that free caplacizumab could bind to biotinylated vWF immobilized on the column. The Gyrolab system automatically transferred the mixture in triplicate to the CDs. Free caplacizumab was detected with 50 nM AlexaFluor647-labeled anti-caplacizumab monoclonal antibody diluted in Rexxip F buffer (commercially available detection buffer). Three independent experiments were performed to determine final KD. The fluorochromes were excited by the red laser so fluorescent signals were obtained and amplified by a photo multiplier tube (PMT). The amplification level of this assay was 1% PMT. An unknown ligand analysis model was used for the KD-determination of caplacizumab. Analysis was performed with the XL fit software of the Gyrolab workstation.

Results a) The relative potency of the liquid and lyophilized ALX-0081 test samples was measured in a Biacore potency assay, relative to the ALX-0081 reference material used in the potency assay, also designated master reference standard 2 (MRS-2). The relative potency was 102.8% and 102.9%, respectively, indicating full comparability with regard to biological potency determined via Biacore (see Table 24).

b) The relative potency of the liquid and lyophilized ALX-0081 test samples was determined in the ELISA-based potency assay, relative to MRS-2. The relative potency values were 99.4% and 109.5%, respectively, and thus well within the comparability criteria (see Table 24). Therefore, these results indicate that both formulations are comparable with respect to potency determined via ELISA.

c) RICO-activity of the liquid and lyophilized ALX-0081 test samples was measured in a side-by-side comparison, and the concentration to completely block RICO activity (<20%) was determined. The concentration to completely block RICO activity (<20%) was 0.4 µg/mL for both formulations. These results are well within comparability criteria (see Table 24) and indicate full comparability with respect to pharmacodynamic activity of both formulations.

d) The affinity constant ($K_D$-value) of the liquid and lyophilized ALX-0081 test samples was also determined in a side-by-side comparison in the Gyrolab-based assay. $K_D$-values were 6.84 pM and 4.46 pM, respectively, with overlapping confidence intervals. Therefore, these results indicate full comparability of both formulations with respect to affinity for the multimeric target vWF (see Table 24).

Conclusion

The objective of this study was to evaluate the in vitro comparability of the liquid and lyophilized drug product of ALX-0081 (caplacizumab) by means of four assays, capable of assessing in vitro biological activity and target binding:

a) Biacore-based potency assay
b) ELISA-based potency assay
c) Ristocetin Induced Cofactor Activity (RICO) pharmacodynamic biomarker assay
d) Gyrolab-based affinity determination All in vitro assays met predefined acceptance criteria and showed that both formulations of ALX-0081 are comparable in terms of biological activity and target binding (see Table 24). The tested liquid and lyophilized ALX-0081 DP formulations showed:

a similar relative potency determined via Biacore and ELISA assay a comparable pharmacodynamic activity in vitro (target neutralization) via RICO assay a comparable target affinity via Gyrolab assay.

Accelerated and Long-Term Stability Testing of Liquid and Lyophilized ALX-0081 Formulations Supplementary to Example 7.12, independent stability experiments were conducted using a different batch of ALX-0081 of the same formulation [20 mM citrate buffer pH 6.5, 7% sucrose (w/v) and 0.01% Tween-80 (v/v)].

The stability of both the lyophilized and the liquid formulation was tested at different temperatures:

The liquid formulation of 13.8 mg/mL ALX-0081 in 20 mM citrate buffer pH 6.5, 7% sucrose (w/v) and 0.01% Tween-80 (v/v) was stored at temperatures ≤−60° C. and +5° C. (±3° C.) and tested for stability at different time points, i.e. initial, 9 months, 12 months, 18 months and 24 months.

The lyophilized formulation of 12.7 mg/mL ALX-0081 in 20 mM citrate buffer pH 6.5, 7% sucrose (w/v) and 0.01% Tween-80 (v/v) was stored at +5° C. (±3° C.), +25° C. (±2° C./60±5% RH) and +40° C. (±2° C./75±5% RH). Similar to the liquid formulation, stability of the lyophilized formulation was determined at 0, 9, 12, 18 and 24 months.

At each time point the chemical and physical stability of the samples was monitored using a number of analytical techniques, including cIEF, RP-HPLC, SE-HPLC, visual appearance, pH and UV absorption. Moisture content of the lyophilized powder was determined by coulometric titration. Relative potency of the liquid and lyophilized samples was measured in Biacore relative to an in-house ALX-0081 reference standard.

Detailed sample characterization data for the liquid and lyophilized formulations are provided in Tables 25 to 26 and Tables 27 to 29, respectively. Samples that fulfilled the criteria as set out in column 2 of each of the aforementioned Tables were considered to be within the product specifications.

The obtained data demonstrates that the invented formulation is highly stable for at least 24 months. The physico-chemical characteristics as well as the biological activity of lyophilized ALX-0081 were not significantly affected by 24 months storage at either +5° C. or +25° C. When stressing ALX-0081 for 24 months at +40° C. an increase in post-peak 2 was observed, corresponding with the formation of the pyroglutamate variant from 1.1% in the starting material to 2.8%, 3.2%, 4.2% and 6.2% after 9, 12, 18 and 24 months, respectively.

Storing liquid ALX-0081 formulations for at least 24 months at temperatures −60° C. or at +5° C., did not significantly affect its physicochemical stability: content values were stable, samples remained clear and cIEF, RP-HPLC and SE-HPLC profiles of the initial material were comparable with those of the stability samples.

The changes reported for lyophilized samples stored at +40° C. can be attributed to the stressed storage conditions and provide a good indication for long term storage stability under milder conditions.

Long-Term Stability Prediction

The current drug product specifications states that the allowed percentage of pyroglutamate is 4%. Based on this specification and the current stability data, the Arrhenius equation was employed to predict the shelf life of the lyophilized drug product at +5° C. and +25° C. The Arrhenius equation is an accurate formula describing the temperature dependence of reaction rates which is commonly used in the pharmaceutical industry. As shown in FIGS. 10 and 11, the lyophilized drug product is expected to remain within specifications for at least 500 months when stored at +5° C. and for at least 60 months when stored at +25° C.

General Conclusion

The reformulation invention for vWF binders, and especially ALX-0081 described herein rendered a new citrate/sucrose based formulation with improved solubility (up to 80 mg/mL) and significantly improved liquid storage stability (e.g. less oxidation compared to its original formulation). Also, in the lyophilized form, essentially no oxidation or asp-isomerisation could be detected after 12 or even 24 months storage at +40° C. Further optimization of the citrate and sucrose concentration resulted in a reduction of the moisture content of the lyophilized product, thereby minimizing the rate of pyroglutamate formation. It was shown that each physicochemical characteristic of the vWF binder was differently influenced by the different constituents, physical as well as chemical, of the formulation, such as buffer choice, pH, concentration, excipient, etc. Various formulations are provided herein optimized for remedying or preventing different chemical and/or physical stresses.

One formulation buffer was designed that met most critical criteria: 20 mM citrate pH 6.5+7.0% sucrose (w/v)+ 0.01% Tween-80 (v/v). Using this formulation, ALX-0081 was shown to be stable for at least 12 or even 24 months at −20° C., +5° C., +25° C. and +40° C. These data clearly point to a considerably longer shelf-life at +5° C. than the current liquid formulation.

In addition the inventors have extensively shown that the contemporaneous formulation of ALX-0081 which has been used in clinical studies to date is comparable to the newly optimized lyophilized ALX-0081 formulation presented herein in terms of in vitro biological activity and target binding.

| | | Table A-1 |
| | | Examples of vWF binders |

| Name | SEQ ID NO | Sequence |
|---|---|---|
| 12A02H1-3a-<br>12A02H1<br>(ALX-0081) | 1 | EVQLVESGGGLVQPGGSLRLSCAASGRTFSYNPMGWFRQAPGKGRELVA<br>AISRTGGSTYYPDSVEGRFTISRDNAKRMVYLQMNSLRAEDTAVYYCAA<br>AGVRAEDGRVRTLPSEYTFWGQGTQVTVSSAAAEVQLVESGGGLVQPGG<br>SLRLSCAASGRTFSYNPMGWFRQAPGKGRELVAAISRTGGSTYYPDSVE<br>GRFTISRDNAKRMVYLQMNSLRAEDTAVYYCAAAGVRAEDGRVRTLPSE<br>YTFWGQGTQVTVSS |
| 12A02-3a-12A02 | 2 | QVKLEESGGGLVQAGGALRLSCAASGRTFSYNPMGWFRQAPGKERDLVA<br>AISRTGGSTYYPDSVEGRFTISRDNAKRMVYLQMNNLKPEDTAVYYCAA<br>AGVRAEDGRVRTLPSEYTFWGQGTQVTVSSAAAEVQLVESGGGLVQAGG<br>ALRLSCAASGRTFSYNPMGWFRQAPGKERDLVAAISRTGGSTYYPDSVE<br>GRFTISRDNAKRMVYLQMNNLKPEDTAVYYCAAAGVRAEDGRVRTLPSE<br>YTFWGQGTQVTVSS |
| 12A02-GS9-12A02 | 3 | QVKLEESGGGLVQAGGALRLSCAASGRTFSYNPMGWFRQAPGKERDLVA<br>AISRTGGSTYYPDSVEGRFTISRDNAKRMVYLQMNNLKPEDTAVYYCAA<br>AGVRAEDGRVRTLPSEYTFWGQGTQVTVSSGGGGSGGGSEVQLVESGGG<br>LVQAGGALRLSCAASGRTFSYNPMGWFRQAPGKERDLVAAISRTGGSTY<br>YPDSVEGRFTISRDNAKRMVYLQMNNLKPEDTAVYYCAAAGVRAEDGRV<br>RTLPSEYTFWGQGTQVTVSS |
| 12A02-GS30-<br>12A02 | 4 | QVKLEESGGGLVQAGGALRLSCAASGRTFSYNPMGWFRQAPGKERDLVA<br>AISRTGGSTYYPDSVEGRFTISRDNAKRMVYLQMNNLKPEDTAVYYCAA<br>AGVRAEDGRVRTLPSEYTFWGQGTQVTVSSGGGGSGGGGSGGGGSGGGG<br>SGGGGSGGGGSEVQLVESGGGLVQAGGALRLSCAASGRTFSYNPMGWFR<br>QAPGKERDLVAAISRTGGSTYYPDSVEGRFTISRDNAKRMVYLQMNNLK<br>PEGTAVYYCAAAGVRAEDGRVRTLPSEYTFWGQGTQVTVSS |
| 12A05-3a-12A05 | 5 | AVQLVESGGGLVQPGGSLRLSCLASGRIFSIGAMGMYRQAPGKQRELVA<br>TITSGGSTNYADPVKGRFTISRDGPKNTVYLQMNSLKPEDTAVYYCYAN<br>LKQGSYGYRFNDYWGQGTQVTVSSAAAEVQLVESGGGLVQPGGSLRLSC<br>LASGRIFSIGAMGMYRQAPGKQRELVATITSGGSTNYADPVKGRFTISR<br>DGPKNTVYLQMNSLKPEDTAVYYCYANLKQGSYGYRFNDYWGQGTQVTV<br>SS |
| 12A05-GS9-12A05 | 6 | AVQLVESGGGLVQPGGSLRLSCLASGRIFSIGAMGMYRQAPGKQRELVA<br>TITSGGSTNYADPVKGRFTISRDGPKNTVYLQMNSLKPEDTAVYYCYAN<br>LKQGSYGYRFNDYWGQGTQVTVSSGGGGSGGGSEVQLVESGGGLVQPGG<br>SLRLSCLASGRIFSIGAMGMYRQAPGKQRELVATITSGGSTNYADPVKG<br>RFTISRDGPKNTVYLQMNSLKPEDTAVYYCYANLKQGSYGYRFNDYWGQ<br>GTQVTVSS |
| 12A05-GS30-<br>12A05 | 7 | AVQLVESGGGLVQPGGSLRLSCLASGRIFSIGAMGMYRQAPGKQRELVA<br>TITSGGSTNYADPVKGRFTISRDGPKNTVYLQMNSLKPEDTAVYYCYAN<br>LKQGSYGYRFNDYWGQGTQVTVSSGGGGSGGGGSGGGGSGGGGSGGGGS<br>GGGGSEVQLVESGGGLVQPGGSLRLSCLASGRIFSIGAMGMYRQAPGKQ<br>RELVATITSGGSTNYADPVKGRFTISRDGPKNTVYLQMNSLKPEDTAVY<br>YCYANLKQGSYGYRFNDYWGQGTQVTVSS |
| 12B06-3a-12B06 | 8 | QVQLVESGGGLVQAGGALRLSCAASGRTFSYNPMGWFRQAPGKERDVVA<br>AISRTGGSTYYARSVEGRFTISRDNAKRMVYLQMNALKPEDTAVYYCAA<br>AGVRAEDGRVRTLPSEYNFWGQGTQVTVSSAAAEVQLVESGGGLVQAGG<br>ALRLSCAASGRTFSYNPMGWFRQAPGKERDVVAAISRTGGSTYYARSVE<br>GRFTISRDNAKRMVYLQMNALKPEDTAVYYCAAAGVRAEDGRVRTLPSE<br>YNFWGQGTQVTVSS |

-continued

| 12B06-GS9-12B06 | 9 | QVQLVESGGGLVQAGGALRLSCAASGRTFSYNPMGWFRQAPGKERDVVA<br>AISRTGGSTYYARSVEGRFTISRDNAKRMVYLQMNALKPEDTAVYYCAA<br>AGVRAEDGRVRTLPSEYNFWGQGTQVTVSSGGGGSGGGGSEVQLVESGGG<br>LVQAGGALRLSCAASGRTFSYNPMGWFRQAPGKERDVVAAISRTGGSTY<br>YARSVEGRFTISRDNAKRMVYLQMNALKPEDTAVYYCAAAGVRAEDGRV<br>RTLPSEYNFWGQGTQVTVSS |
|---|---|---|
| 12B06-GS30-12B06 | 10 | QVQLVESGGGLVQAGGALRLSCAASGRTFSYNPMGWFRQAPGKERDVVA<br>AISRTGGSTYYARSVEGRFTISRDNAKRMVYLQMNALKPEDTAVYYCAA<br>AGVRAEDGRVRTLPSEYNFWGQGTQVTVSSGGGGSGGGGSGGGGSGGGG<br>SGGGGSGGGGSEVQLVESGGGLVQAGGALRLSCAASGRTFSYNPMGWFR<br>QAPGKERDVVAAISRTGGSTYYARSVEGRFTISRDNAKRMVYLQMNALK<br>PEDTAVYYCAAAGVRAEDGRVRTLPSEYNFWGQGTQVTVSS |
| 12A02H4-3a-12A02H4 | 11 | EVQLVESGGGLVQPGGSLRLSCAASGRTFSYNPMGWFRQAPGKGRELVA<br>AISRTGGSTYYPDSVEGRFTISRDNAKRSVYLQMNSLRAEDTAVYYCAA<br>AGVRAEDGRVRTLPSEYTFWGQGTQVTVSSAAAEVQLVESGGGLVQPGG<br>SLRLSCAASGRTFSYNPMGWFRQAPGKGRELVAAISRTGGSTYYPDSVE<br>GRFTISRDNAKRSVYLQMNSLRAEDTAVYYCAAAGVRAEDGRVRTLPSE<br>YTFWGQGTQVTVSS |
| 12B06H2-3a-12B06H2 | 12 | EVQLVESGGGLVQPGGSLRLSCAASGRTFSYNPMGWFRQAPGKGREVVA<br>AISRTGGSTYYARSVEGRFTISRDNAKRMVYLQMNSLRAEDTAVYYCAA<br>AGVRAEDGRVRTLPSEYNFWGQGTQVTVSSAAAEVQLVESGGGLVQPGG<br>SLRLSCAASGRTFSYNPMGWFRQAPGKGREVVAAISRTGGSTYYARSVE<br>GRFTISRDNAKRMVYLQMNSLRAEDTAVYYCAAAGVRAEDGRVRTLPSE<br>YNFWGQGTQVTVSS |
| 12A02H1-GS9-12A02H1 | 13 | EVQLVESGGGLVQPGGSLRLSCAASGRTFSYNPMGWFRQAPGKGRELVA<br>AISRTGGSTYYPDSVEGRFTISRDNAKRMVYLQMNSLRAEDTAVYYCAA<br>AGVRAEDGRVRTLPSEYTFWGQGTQVTVSSGGGGSGGGGSEVQLVESGGG<br>LVQPGGSLRLSCAASGRTFSYNPMGWFRQAPGKGRELVAAISRTGGSTY<br>YPDSVEGRFTISRDNAKRMVYLQMNSLRAEDTAVYYCAAAGVRAEDGRV<br>RTLPSEYTFWGQGTQVTVSS |
| 12A02H4-GS9-12A02H4 | 14 | EVQLVESGGGLVQPGGSLRLSCAASGRTFSYNPMGWFRQAPGKGRELVA<br>AISRTGGSTYYPDSVEGRFTISRDNAKRSVYLQMNSLRAEDTAVYYCAA<br>AGVRAEDGRVRTLPSEYTFWGQGTQVTVSSGGGGSGGGGSEVQLVESGGG<br>LVQPGGSLRLSCAASGRTFSYNPMGWFRQAPGKGRELVAAISRTGGSTY<br>YPDSVEGRFTISRDNAKRSVYLQMNSLRAEDTAVYYCAAAGVRAEDGRV<br>RTLPSEYTFWGQGTQVTVSS |
| 12B06H2-GS9-12B06H2 | 15 | EVQLVESGGGLVQPGGSLRLSCAASGRTFSYNPMGWFRQAPGKGREVVA<br>AISRTGGSTYYARSVEGRFTISRDNAKRMVYLQMNSLRAEDTAVYYCAA<br>AGVRAEDGRVRTLPSEYNFWGQGTQVTVSSGGGGSGGGGSEVQLVESGGG<br>LVQPGGSLRLSCAASGRTFSYNPMGWFRQAPGKGREVVAAISRTGGSTY<br>YARSVEGRFTISRDNAKRMVYLQMNSLRAEDTAVYYCAAAGVRAEDGRV<br>RTLPSEYNFWGQGTQVTVSS |
| 12A02H1-GS30-12A02H1 | 16 | EVQLVESGGGLVQPGGSLRLSCAASGRTFSYNPMGWFRQAPGKGRELVA<br>AISRTGGSTYYPDSVEGRFTISRDNAKRMVYLQMNSLRAEDTAVYYCAA<br>AGVRAEDGRVRTLPSEYTFWGQGTQVTVSSGGGGSGGGGSGGGGSGGGG<br>SGGGGSGGGGSEVQLVESGGGLVQPGGSLRLSCAASGRTFSYNPMGWFR<br>QAPGKGRELVAAISRTGGSTYYPDSVEGRFTISRDNAKRMVYLQMNSLR<br>AEDTAVYYCAAAGVRAEDGRVRTLPSEYTFWGQGTQVTVSS |
| 12A02H4-GS30-12A02H4 | 17 | EVQLVESGGGLVQPGGSLRLSCAASGRTFSYNPMGWFRQAPGKGRELVA<br>AISRTGGSTYYPDSVEGRFTISRDNAKRSVYLQMNSLRAEDTAVYYCAA<br>AGVRAEDGRVRTLPSEYTFWGQGTQVTVSSGGGGSGGGGSGGGGSGGGG<br>SGGGGSGGGGSEVQLVESGGGLVQPGGSLRLSCAASGRTFSYNPMGWFR<br>QAPGKGRELVAAISRTGGSTYYPDSVEGRFTISRDNAKRSVYLQMNSLR<br>AEDTAVYYCAAAGVRAEDGRVRTLPSEYTFWGQGTQVTVSS |
| 12B06H2-GS30-12B06H2 | 18 | EVQLVESGGGLVQPGGSLRLSCAASGRTFSYNPMGWFRQAPGKGREVVA<br>AISRTGGSTYYARSVEGRFTISRDNAKRMVYLQMNSLRAEDTAVYYCAA<br>AGVRAEDGRVRTLPSEYNFWGQGTQVTVSSGGGGSGGGGSGGGGSGGGG<br>SGGGGSGGGGSEVQLVESGGGLVQPGGSLRLSCAASGRTFSYNPMGWFR<br>QAPGKGREVVAAISRTGGSTYYARSVEGRFTISRDNAKRMVYLQMNSLR<br>AEDTAVYYCAAAGVRAEDGRVRTLPSEYNFWGQGTQVTVSS |
| 12A02H1 | 19 | EVQLVESGGGLVQPGGSLRLSCAASGRTFSYNPMGWFRQAPGKGRELVA<br>AiSRTGGSTYYPDSVEGRFTISRDNAKRMVYLQMNSLRAEDTAVYYCAA<br>AGVRAEDGRVRTLPSEYTFWGQGTQVTVSS |

-continued

Table A-2

| Name | SEQ ID NO | Sequence |
|------|-----------|----------|
| Human vWF | 20 | MIPARFAGVLLALALILPGTLCAEGTRGRSSTARCSLFGSDFVNTFDGSMYSFAG<br>YCSYLLAGGCQKRSFSIIGDFQNGKRVSLSVYLGEFFDIHLFVNGTVTQGDQRVS<br>MPYASKGLYLETEAGYYKLSGEAYGFVARIDGSGNFQVLLSDRYFNKTCGLCGNF<br>NIFAEDDFMTQEGTLTSDPYDFANSWALSSGEQWCERASPPSSSCNISSGEMQKG<br>LWEQCQLLKSTSVFARCHPLVDPEPFVALCEKTLCECAGGLECACPALLEYARTC<br>AQEGMVLYGWTDHSACSPVCPAGMEYRQCVSPCARTCQSLHINEMCQERCVDGCS<br>CPEGQLLDEGLCVESTECPCVHSGKRYPPGTSLSRDCNTCICRNSQWICSNEECP<br>GECLVTGQSHFKSFDNRYFTFSGICQYLLARDCQDHSFSIVIETVQCADDRDAVC<br>TRSVTVRLPGLHNSLVKLKHGAGVAMDGQDIQLPLLKGDLRIQHTVTASVRLSYG<br>EDLQMDWDGRGRLLVKLSPVYAGKTCGLCGNYNGNQGDDFLTPSGLAEPRVEDFG<br>NAWKLHGDCQDLQKQHSDPCALNPRMTRFSEEACAVLTSPTFEACHRAVSPLPYL<br>RNCRYDVCSCSDGRECLCGALASYAAACAGRGVRVAWREPGRCELNCPKGQVYLQ<br>CGTPCNLTCRSLSYPDEECNEACLEGCFCPPGLYMDERGDCVPKAQCPCYYDGEI<br>FQPEDIFSDHHTMCYCEDGFMHCTMSGVPGSLLPDAVLSSPLSHRSKRSLSCRPP<br>MVKLVCPADNLRAEGLECTKTCQNYDLECMSMGCVSGCLCPPGMVRHENRCVALE<br>RCPCFHQGKEYAPGETVKIGCNTCVCRDRKWNCTDHVCDATCSTIGMAHYLTFDG<br>LKYLFPGECQYVLVQDYCGSNPGTFRILVGNKGCSHPSVKCKKRVTILVEGGEIE<br>LFDGEVNVKRPMKDETHFEVVESGRYIILLLGKALSVVWDRHLSISVVLKQTYQE<br>KVCGLCGNFDGIQNNDLTSSNLQVEEDPVDFGNSWKVSSQCADTRKVPLDSSPAT<br>CHNNIMKQTMVDSSCRILTSDVFQDCNKLVDPEPYLDVCIYDTCSCESIGDCACF<br>CDTIAAYAHVCAQHGKVVTWRTATLCPQSCEERNLRENGYECEWRYNSCAPACQV<br>TCQHPEPLACPVQCVEGCHACPPGKILDELLQTCVDPEDCPVCEVAGRRFASGK<br>KVTLNPSDPEHCQICHCDVVNLTCEACQEPGGLVVPPTDAPVSPTTLYVEDISEP<br>PLHDFYCSRLLDLVFLLDGSSRLSEAEFEVLKAFVVDMMERLRISQKWVRVAVVE<br>YHDGSHAYIGLKDRKRPSELRRIASQVKYAGSQVASTSEVLKYTLFQIFSKIDRP<br>EASRIALLLMASQEPQRMSRNFVRYVQGLKKKKVIVIPVGIGPHANLKQIRLIEK<br>QAPENKAFVLSSVDELEQQRDEIVSYLCDLAPEAPPPTLPPHMAQVTVGPGLRNS<br>MVLDVAFVLEGSDKIGEADFNRSKEFMEEVIQRMDVGQDSIHVTVLQYSYMVTVE<br>YPFSEAQSKGDILQRVREIRYQGGNRTNTGLALRYLSDHSFLVSQGDREQAPNLV<br>YMVTGNPASDEIKRLPGDIQVVPIGVGPNANVQELERIGWPNAPILIQDFETLPR<br>EAPDLVLQRCCSGEGLQIPTLSPAPDCSQPLDVILLLDGSSSFPASYFDEMKSFA<br>KAFISKANIGPRLTQVSVLQYGSITTIDVPWNVVPEKAHLLSLVDVMQREGGPSQ<br>IGDALGFAVRYLTSEMHGARPGASKAVVILVTDVSVDSVDAAADAARSNRVTVFP<br>IGIGDRYDAAQLRILAGPAGDSNVVKLQRIEDLPTMVTLGNSFLHKLCSGFVRIC<br>MDEDGNEKRPGDVWTLPDQCHTVTCQPDGQTLLKSHRVNCDRGLRPSCPNSQSPV<br>KVEETCGCRWTCPCVCTGSSTRHIVTFDGQNFKLTGSCSYVLFQNKEQDLEVILH<br>NGACSPGARQGCMKSIEVKHSALSVELHSDMEVTVNGRLVSVPYVGGNMEVNVYG<br>AIMHEVRFNHLGHIFTFTPQNNEFQLQLSPKTFASKTYGLCGICDENGANDFMLR<br>DGTVTTDWKTLVQEWTVQRPGQTCQPILEEQCLVPDSSHCQVLLLPLFAECHKVL<br>APATFYAICQQDSCHQEQVCEVIASYAHLCRTNGVCVDWRTPDFCAMSCPPSLVY<br>NHCEHGCPRHCDGNVSSCGDHPSEGCFCPPDKVMLEGSCVPEEACTQCIGEDGVQ<br>HQFLEAWVPDHQPCQICTCLSGRKVNCTTQPCPTAKAPTCGLCEVARLRQNADQC<br>CPEYECVCDPVSCDLPPVPHCERGLQPTLTNPGECRPNFTCACRKEECKRVSPPS<br>CPPHRLPTLRKTQCCDEYECACNCVNSTVSCPLGYLASTATNDCGCTTTTCLPDK<br>VCVHRSTIYPVGQFWEEGCDVCTCTDMEDAVMGLRVAQCSQKPCEDSCRSGFTYV<br>LHEGECCGRCLPSACEVVTGSPRGDSQSSWKSVGSQWASPENPCLINECVRVKEE<br>VFIQQRNVSCPQLEVPVCPSGFQLSCKTSACCPSCRCERMEACMLNGTVIGPGKT<br>VMIDVCTTCRCMVQVGVISGFKLECRKTTCNPCPLGYKEENNTGECCGRCLPTAC<br>TIQLRGGQIMTLKRDETLQDGCDTHFCKVNERGEYFWEKRVTGCPPFDEHKCLAE<br>GGKIMKIPGTCCDTCEEPECNDITARLQYVKVGSCKSEVEVDIHYCQGKCASKAM<br>YSIDINDVQDQCSCCSPTRTEPMQVALHCTNGSVVYHEVLNAMECKCSPRKCSK |

TABLE 1

Overview of 50 different buffer/excipient combinations predicted by the
Design Expert program to yield the highest melting temperatures for ALX-
0081. The buffer/excipient combinations are ranked according to the Tm
value. Different buffer types are shown as different symbols.

| | | Buffer | | Excipient 1 | | Glycine | NaCl | |
|-----|------|--------|------|-------------|------|---------|------|------|
| Run | Name | Conc (mM) | Name | | Conc (mM) | Conc (mM) | Conc (mM) | Tm ° C. |
| Δ 1 | Phosphate pH 6.92 | 17.24 | Trehalose | | 239.25 | 0.00 | 0.00 | 77.2772 |
| Δ 2 | Phosphate pH 6.98 | 16.29 | Trehalose | | 242.04 | 0.00 | 0.00 | 77.2742 |
| Δ 3 | Phosphate pH 6.95 | 9.47 | Trehalose | | 262.12 | 0.00 | 0.00 | 77.2641 |
| Δ 4 | Phosphate pH 7.50 | 9.47 | Mannitol | | 0.00 | 273.04 | 0.00 | 77.2096 |
| Δ 5 | Phosphate pH 7.50 | 25.19 | Mannitol | | 0.00 | 224.82 | 0.00 | 77.1483 |
| Δ 6 | Phosphate pH 7.50 | 9.47 | Sucrose | | 0.00 | 273.04 | 0.00 | 77.1399 |
| Δ 7 | Phosphate pH 7.50 | 28.79 | Mannitol | | 0.00 | 213.78 | 0.00 | 77.1262 |

TABLE 1-continued

Overview of 50 different buffer/excipient combinations predicted by the
Design Expert program to yield the highest melting temperatures for ALX-
0081. The buffer/excipient combinations are ranked according to the Tm
value. Different buffer types are shown as different symbols.

| | | Buffer | | Excipient 1 | | Glycine | NaCl | |
| Run | Name | Conc (mM) | Name | Conc (mM) | Conc (mM) | Conc (mM) | Conc (mM) | Tm ° C. |
|---|---|---|---|---|---|---|---|---|
| Δ 8 | Phosphate pH 7.50 | 30.88 | Mannitol | 0.00 | 207.39 | 0.00 | 77.1117 |
| Δ 9 | Phosphate pH 7.50 | 32.96 | Mannitol | 0.00 | 201.00 | 0.00 | 77.0953 |
| ¤ 10 | Citrate pH 6.23 | 48.16 | Trehalose | 162.85 | 0.00 | 0.00 | 77.0307 |
| ¤ 11 | Citrate pH 6.22 | 48.38 | Trehalose | 162.29 | 0.00 | 0.00 | 77.0307 |
| Δ 12 | Phosphate pH 6.87 | 19.89 | Mannitol | 231.44 | 0.00 | 0.00 | 76.9832 |
| Δ 13 | Phosphate pH 7.50 | 9.47 | Trehalose | 0.00 | 273.04 | 0.00 | 76.9483 |
| ¤ 14 | Citrate pH 7.00 | 60.84 | Sucrose | 129.38 | 0.00 | 0.00 | 76.9338 |
| ¤ 15 | Citrate pH 7.00 | 57.67 | Sucrose | 137.75 | 0.00 | 0.00 | 76.9312 |
| Δ 16 | Phosphate pH 7.50 | 50.01 | Mannitol | 0.00 | 148.72 | 0.00 | 76.9295 |
| ¤ 17 | Citrate pH 7.00 | 84.92 | Sucrose | 65.25 | 0.00 | 0.00 | 76.7979 |
| Δ 18 | Phosphate pH 7.06 | 36.18 | Sucrose | 183.48 | 0.00 | 0.00 | 76.7972 |
| ¤ 19 | Citrate pH 6.44 | 10.56 | Trehalose | 262.12 | 0.00 | 0.00 | 76.7449 |
| ¤ 20 | Citrate pH 7.00 | 77.11 | Mannitol | 0.00 | 90.04 | 0.00 | 76.7297 |
| ¤ 21 | Citrate pH 7.00 | 75.42 | Mannitol | 0.00 | 94.69 | 0.00 | 76.7291 |
| ¤ 22 | Citrate pH 7.00 | 79.01 | Mannitol | 0.00 | 81.42 | 0.00 | 76.6192 |
| ¤ 23 | Citrate pH 6.17 | 53.45 | Mannitol | 146.67 | 2.90 | 0.00 | 76.5956 |
| ¤ 24 | Citrate pH 6.18 | 53.23 | Mannitol | 149.46 | 0.00 | 0.00 | 76.5955 |
| ¤ 25 | Citrate pH 6.18 | 53.23 | Mannitol | 149.46 | 0.00 | 0.00 | 76.5955 |
| ¤ 26 | Citrate pH 6.16 | 53.66 | Mannitol | 148.35 | 0.00 | 0.00 | 76.5955 |
| † 27 | Tris pH 7.77 | 17.13 | Trehalose | 134.96 | 0.00 | 69.29 | 76.1017 |
| † 28 | Tris pH 8.00 | 89.75 | Mannitol | 0.00 | 15.10 | 70.51 | 76.0374 |
| † 29 | Tris pH 8.00 | 92.83 | Mannitol | 0.00 | 16.27 | 67.17 | 76.0343 |
| † 30 | Tris pH 8.00 | 93.86 | Mannitol | 0.00 | 0.00 | 74.76 | 76.0322 |
| † 31 | Tris pH 7.83 | 17.13 | Sucrose | 142.77 | 0.00 | 65.04 | 76.0321 |
| † 32 | Tris pH 7.82 | 17.13 | Sucrose | 142.21 | 0.00 | 65.34 | 76.0321 |
| † 33 | Tris pH 8.00 | 82.56 | Mannitol | 0.00 | 31.37 | 68.38 | 76.0298 |
| † 34 | Tris pH 8.00 | 97.63 | Mannitol | 0.00 | 0.00 | 71.42 | 76.0285 |
| † 35 | Tris pH 8.00 | 95.23 | Sucrose | 0.00 | 0.00 | 73.55 | 75.9714 |
| † 36 | Tris pH 8.00 | 97.63 | Sucrose | 0.00 | 0.00 | 71.42 | 75.97 |
| † 37 | Tris pH 7.77 | 17.13 | Mannitol | 121.58 | 0.00 | 76.59 | 75.5801 |
| † 38 | Tris pH 8.00 | 61.32 | Trehalose | 0.00 | 53.45 | 75.37 | 75.3047 |
| † 39 | Tris pH 8.00 | 67.14 | Trehalose | 0.00 | 47.06 | 73.85 | 75.3027 |
| † 40 | Tris pH 7.81 | 17.13 | Trehalose | 0.00 | 140.00 | 69.60 | 75.2196 |
| ◇ 41 | Histidine pH 6.50 | 20.03 | Sucrose | 0.00 | 142.33 | 68.38 | 74.9111 |
| ◇ 42 | Histidine pH 6.50 | 20.03 | Sucrose | 0.00 | 136.52 | 71.42 | 74.91 |
| ◇ 43 | Histidine pH 6.50 | 20.03 | Sucrose | 0.00 | 124.90 | 77.50 | 74.9012 |
| ◇ 44 | Histidine pH 6.50 | 20.03 | Mannitol | 0.00 | 127.22 | 76.28 | 74.8582 |
| ◇ 45 | Histidine pH 6.50 | 20.03 | Mannitol | 0.00 | 131.29 | 74.16 | 74.8576 |
| ◇ 46 | Histidine pH 6.50 | 20.03 | Mannitol | 0.00 | 118.51 | 80.84 | 74.8558 |
| ◇ 47 | Histidine pH 6.50 | 20.03 | Mannitol | 0.00 | 136.52 | 71.42 | 74.8553 |
| ◇ 48 | Histidine pH 6.50 | 20.83 | Mannitol | 0.00 | 109.21 | 85.10 | 74.8397 |
| ◇ 49 | Histidine pH 6.49 | 20.03 | Mannitol | 0.00 | 146.98 | 65.95 | 74.8281 |
| ◇ 50 | Histidine pH 6.50 | 20.03 | Trehalose | 0.00 | 144.07 | 67.47 | 74.4053 |

TABLE 2

Solubility testing of ALX-0081 in different formulation buffers.

| formulation | pH | visual | measured conc. (mg/mL) | recovery (%) |
|---|---|---|---|---|
| D-PBS + 200 mM glycine | 7.4 | turbid + small particles | 8.1 | 88.6 |
| 10 mM phosphate + 200 mM glycine | 7.4 | turbid + small particles | 8.7 | 88.3 |
| 20 mM phosphate | 7.4 | turbid + particles | 4.9 | 96.4 |
| 20 mM histidine | 6.5 | turbid + particles | <3.4 | N.D. |
| 20 mM citrate | 7.0 | clear | 55.9 | 97.6 |

N.D. = not determined

TABLE 3

Overview of liquid ALX-0081 formulations evaluated in a storage and
FT stability trial, together with measured pH and osmolality values.

| formulation no. | conc. (mg/mL) | buffer type | buffer pH | excipient strength | excipient type | Tween-80 (v/v) | pH measured | osmolality mOsm/kg |
|---|---|---|---|---|---|---|---|---|
| 1 | 20 | 50 mM citrate | 6.0 | 75 mM | NaCl | 0.01% | 5.9 | 281 |
| 2 | | | | 2.0% | mannitol | | 6.0 | 253 |
| 3 | | | | 4.0% | sucrose | | 6.0 | 272 |
| 4 | | | | 140 mM | glycine | | 6.0 | 273 |
| 5 | | | 6.5 | 75 mM | NaCl | | 6.5 | 288 |
| 6 | | | | 2.0% | mannitol | | 6.5 | 266 |
| 7 | | | | 4.0% | sucrose | | 6.6 | 280 |
| 8 | | | | 140 mM | glycine | | 6.6 | 280 |
| 9 | | | 7.0 | 75 mM | NaCl | | 6.9 | 279 |
| 10 | | | | 2.0% | mannitol | | 7.0 | 259 |
| 11 | | | | 4.0% | sucrose | | 7.1 | 271 |
| 12 | | | | 140 mM | glycine | | 7.0 | 278 |
| 13 | 5 | | | 75 mM | NaCl | | 6.9 | 274 |
| 14 | | | | 2.0% | mannitol | | 7.0 | 254 |
| 15 | | | | 4.0% | sucrose | | 7.0 | 267 |
| 16 | | | | 140 mM | glycine | | 7.0 | 274 |
| 17 | | D-PBS | 7.1 | 137/200 mM | NaCl/glycine | | 7.2 | 470 |

TABLE 4

Overview of the storage stability study of different ALX-0081 formulations.
Time points, storage temperatures and methods are indicated.

| time point | temperature −70° C. | temperature +40° C. | formulation no. as indicated in Table 3 | methods RP-HPLC | methods cIEF | methods SE-HPLC |
|---|---|---|---|---|---|---|
| 1 week | X | X | 1-17 | X | | |
| 2 weeks | X | X | 1-17 | X | | |
| 1 month | X | X | 1-17 | X | X | X |

TABLE 5

Storage stability data for the different liquid ALX-0081 formulations. The relative surface
areas of the most relevant RP-HPLC peaks after 1 month storage at +40° C. are shown.

| formulation no. | conc. (mg/mL) | buffer type | buffer pH | excipient strength | excipient type | Tween-80 (v/v) | % peak area RP-HPLC oxidation | % peak area RP-HPLC main | % peak area RP-HPLC pyro |
|---|---|---|---|---|---|---|---|---|---|
| 1 | 20 | 50 mM citrate | 6.0 | 75 mM | NaCl | 0.01% | ◊ 1.5 | Δ 88.6 | Δ 3.7 |
| 2 | | | | 2.0% | mannitol | | ◊ 1.7 | Δ 88.1 | Δ 4.3 |
| 3 | | | | 4.0% | sucrose | | ◊ 1.7 | Δ 88.1 | Δ 4.6 |
| 4 | | | | 140 mM | glycine | | Δ 2.2 | Δ 88.3 | Δ 3.9 |
| 5 | | | 6.5 | 75 mM | NaCl | | Δ 2.5 | Δ 88.5 | Δ 3.6 |
| 6 | | | | 2.0% | mannitol | | Δ 2.7 | Δ 87.5 | Δ 4.5 |
| 7 | | | | 4.0% | sucrose | | Δ 2.3 | Δ 88.0 | Δ 4.2 |
| 8 | | | | 140 mM | glycine | | † 4.6 | Δ 85.2 | Δ 4.3 |
| 9 | | | 7.0 | 75 mM | NaCl | | Δ 2.4 | Δ 86.8 | † 5.2 |
| 10 | | | | 2.0% | mannitol | | Δ 2.6 | Δ 86.0 | † 5.9 |
| 11 | | | | 4.0% | sucrose | | Δ 2.8 | Δ 85.9 | •● 6.1 |
| 12 | | | | 140 mM | glycine | | † 4.7 | † 82.8 | ● 6.2 |
| 13 | 5 | | | 75 mM | NaCl | | Δ 2.3 | Δ 86.8 | † 5.2 |
| 14 | | | | 2.0% | mannitol | | Δ 2.4 | Δ 86.5 | † 5.8 |
| 15 | | | | 4.0% | sucrose | | Δ 2.1 | Δ 87.7 | † 5.2 |
| 16 | | | | 140 mM | glycine | | † 5.0 | † 83.1 | ● 6.4 |
| 17 | | D-PBS | 7.1 | 137/200 mM | NaCl/glycine | | ● 9.0 | ● 75.2 | ● 6.4 |

Pyro = pyroglutamate, main = main peak (including the shoulder peak, when present), oxidation = pre-peaks collectively.
Symbols indicate the relative sample purity: highest purity ◊, intermediate purity Δ and †, and lowest purity ●.
Recovery was ±100% for all samples.

TABLE 6

Overview of lyophilized/liquid ALX-0081 formulations evaluated in a storage stability trial.

| formu-lation | conc. | buffer | | excipient | | Tween-80 |
|---|---|---|---|---|---|---|
| no. | (mg/mL) | type | pH | strength | type | (v/v) |
| 3 | 20 | 50 mM citrate | 6.0 | 4.0% (w/v) | sucrose | 0.01% |
| 7 | | | 6.5 | 4.0% (w/v) | sucrose | |
| 17 | 5 | D-PBS | 7.1 | 137/200 mM | NaCl/ glycine | |

TABLE 7

Recovery of ALX-0081 in different formulations after lyophilization and reconstitution based on total areas reported by RP-HPLC and SE-HPLC.

| recovery after lyophilization/ reconstitution (%) | citrate pH 6.0 + sucrose (formulation 3) | citrate pH 6.5 + sucrose (formulation 7) | D-PBS + glycine (formulation 17) |
|---|---|---|---|
| RP-HPLC | 104.3 | 105.4 | 103.2 |
| SE-HPLC | 101.3 | 99.6 | 102.8 |

TABLE 8

Overview of storage stability data of the different lyophilized ALX-0081 formulations (1.5 months storage at −20° C., +5° C., +25 C. and +40° C.).

| | | citrate pH 6.0 + sucrose (formulation 3) | | | | citrate pH 6.5 + sucrose (formulation 7) 1.5 months storage | | | | D-PBS + glycine (formulation 17) | | | |
|---|---|---|---|---|---|---|---|---|---|---|---|---|---|
| | | −20° C. | +5° C. | +25° C. | +40° C. | −20° C. | +5° C. | +25° C. | +40° C. | −20° C. | +5° C. | +25° C. | +40° C. |
| | visual | cake not affected by storage + reconstitution with Milli-Q water renders clear solution in all samples | | | | | | | | | | | |
| content | conc. (mg/mL) | N.T. | N.T. | N.T. | 21.1 | N.T. | N.T. | N.T. | 21.2 | N.T. | N.T. | N.T. | 4.89 |
| | recovery* (%) | N.T. | N.T. | N.T. | 106 | N.T. | N.T. | N.T. | 105 | N.T. | N.T. | N.T. | 101 |
| | pH | N.T. | N.T. | N.T. | 6.1 | N.T. | N.T. | N.T. | 6.6 | N.T. | N.T. | N.T. | 7.0 |
| | osmolality (mOsm/kg) | N.T. | N.T. | N.T. | 289 | N.T. | N.T. | N.T. | 295 | N.T. | N.T. | N.T. | 487 |
| RP-HPLC | area % main peak | 92.9 | 92.9 | 92.3 | ○89.7 | 93.0 | 92.9 | 92.8 | □91.4 | 92.3 | 92.1 | Δ88.9 | ●65.8 |
| | area % pre peaks | 2.4 | 2.2 | 2.2 | 2.5 | 2.3 | 2.3 | 2.2 | 2.4 | 2.8 | ○3.0 | Δ4.3 | ●16.1 |
| | area % pyro | 0.9 | 1.0 | ○1.6 | Δ3.9 | 0.8 | 0.9 | □1.2 | ○2.2 | □1.0 | □1.1 | Δ2.8 | ●12.6 |
| | recovery* (%) | 104 | 102 | 113 | 100 | 105 | 102 | 103 | 102 | 103 | 105 | 112 | 96.5 |
| cIEF | area % pyro | N.T. | N.T. | N.T. | Δ3.6 | N.T. | N.T. | N.T. | ○1.1 | N.T. | N.T. | N.T. | ●12.7 |
| SE-HPLC | area % main peak | 99.9 | 99.9 | 99.9 | 99.8 | 99.9 | 99.9 | 99.9 | 99.9 | 99.9 | 100 | 99.9 | ●95.8 |
| | area % pre peaks (HMWs) | 0.1 | 0.1 | 0.1 | 0.2 | 0.1 | 0.1 | 0.1 | 0.1 | 0.1 | 0.0 | 0.1 | ●4.2 |
| | recovery* (%) | 101 | 98.4 | 108 | 100 | 99.7 | 95.0 | 96.2 | 99.0 | 103 | 98.1 | 101 | ●89.6 |

The symbols represent a qualitative assessment of the sample stability, ranging from no symbol to □ to ○ to Δ ●.
N.T. = not tested.
(*compared to liquid control sample kept at −70° C.)

TABLE 9

Overview of ALX-0081 formulations evaluated in a storage stability trial.

| conc. (mg/mL) | lyo cycle time (hours) | citrate buffer | | | Tween-80 (v/v) |
|---|---|---|---|---|---|
| | | strength (mM) | pH | sucrose | |
| 20 | ±65 | 50 | 6.5 | 4.0% | 0.01% |
| | | 32 | | 5.5% | |
| | | 15 | | 7.0% | |

TABLE 9-continued

Overview of ALX-0081 formulations evaluated in a storage stability trial.

| conc. (mg/mL) | lyo cycle time (hours) | citrate buffer | | | Tween-80 (v/v) |
|---|---|---|---|---|---|
| | | strength (mM) | pH | sucrose | |
| | ±37 | 50 | | 4.0% | |
| | | 32 | | 5.5% | |
| | | 15 | | 7.0% | |

TABLE 10

Moisture content of lyophilized ALX-0081 samples and relative amounts
of pyroglutamate detected on RP-HPLC after 4 weeks storage at +40° C.

| conc. (mg/mL) | lyo cycle time (hours) | citrate buffer Strength (mM) | pH | sucrose | Tween-80 (v/v) | moisture content | RP-HPLC pyro |
|---|---|---|---|---|---|---|---|
| 20 | ±65 | 50 | 6.5 | 4.0% | 0.01% | 4.87% | 1.7% |
| | | 32 | | 5.5% | | 2.32% | 1.4% |
| | | 15 | | 7.0% | | 1.27% | 1.2% |
| | ±37 | 50 | | 4.0% | | 4.40% | 1.6% |
| | | 32 | | 5.5% | | not available | 1.3% |
| | | 15 | | 7.0% | | 2.43% | 1.1% |

TABLE 11

Results of visual inspection of ALX-0081 formulation during storage at +5° C. and +25° C.

| conc. (mg/mL) | citrate pH 6.5 (mM) | sucrose w/v (%) | Tween-80 v/v (%) | storage at +5° C. 1 h | 2 h | 19 h | 24 h | 4 d | storage at +25° C. 1 h | 2 h | 19 h | 24 h | 4 d |
|---|---|---|---|---|---|---|---|---|---|---|---|---|---|
| 28 | 15 | — | — | − | − | − | − | − | + | + | + | + | + |
| | 20 | — | — | + | + | + | − | − | + | + | + | + | + |
| | 25 | — | — | + | + | + | − | − | + | + | + | + | + |
| | 30 | — | — | + | + | + | − | − | + | + | + | + | + |
| | 40 | — | — | + | + | + | − | − | + | + | + | + | + |
| | 50 | — | — | + | + | + | + | + | + | + | + | + | + |
| 20 | 15 | 5.0 | — | + | + | + | + | +/− | + | + | + | + | + |
| | 15 | 6.0 | — | + | + | + | + | + | + | + | + | + | + |
| | 15 | 7.0 | — | + | + | + | + | + | + | + | + | + | + |
| | 15 | 5.0 | 0.01 | + | + | + | + | +/− | + | + | + | + | + |
| | 15 | 6.0 | 0.01 | + | + | + | + | + | + | + | + | + | + |
| | 15 | 7.0 | 0.01 | + | + | + | + | + | + | + | + | + | + |

"+" = clear, "+/−" = slightly turbid, "−" = hazy "h" = hour, "d" = days.

TABLE 12

Results of visual inspection, content and SE-HPLC analysis of ALX-0081 formulations
after 5 consecutive FT cycles at −20° C.

| conc. (mg/mL) | citrate pH 6.5 (mM) | sucrose w/v (%) | Tween-80 (v/v) (%) | 5 FT cycles at −20° C. visual | content recovery (%)* | SE-HPLC profile | recovery (%)* |
|---|---|---|---|---|---|---|---|
| 16 | 20 | 5.0 | 0.01 | clear | 100 | no effect | 105.3 |
| | | 6.0 | | | 102 | | 99.4 |
| | | 7.0 | | | 99.0 | | 103.4 |
| | 25 | 5.0 | | | 101 | | 103.9 |
| | | 6.0 | | | 102 | | 98.5 |
| | | 7.0 | | | 100 | | 98.4 |
| | 30 | 5.0 | | | 97.2 | | 98.8 |
| | | 6.0 | | | 103 | | 99.3 |
| | | 7.0 | | | 97.5 | | 102.8 |

(*compared to liquid control sample kept at ≤−70° C.).

TABLE 13

Results of visual inspection, recovery and osmolality measurements of ALX-0081
formulations after 5 consecutive FT cycles at −20° C. or after 1 FT cycle +24 h storage +1 FT cycle
(*compared to liquid control sample kept at ≤−70° C.).

| formulation | | | | 5 FT cycles at −20° C. | | | 1 FT cycle + 24 h at 25° C. + 1 FT cycle | | |
| conc. | citrate | sucrose | Tween- | | | | | | |
| (mg/ mL) | pH 6.5 (mM) | w/v (%) | 80 (v/v) (%) | visual | recovery (%)* | osmolality (mOsm/kg) | visual | recovery (%) | osmolality (mOsm/kg) |
|---|---|---|---|---|---|---|---|---|---|
| 20 | 20 | 5.0 | 0.01 | clear | 103 | 236 | clear | 101 | 236 |
| | | 6.0 | | | 104 | 273 | | 101 | 271 |
| | | 7.0 | | | 103 | 304 | | 99.4 | 306 |

TABLE 14

Lyophilization parameters.

| Step No | Description | Temperature (° C.) | Pressure | Time (hh:mm) |
|---|---|---|---|---|
| 1 | Load | 20 | Atmospheric | N.A |
| 2 | Freezing | 20 → −50 | Atmospheric | 02:00 |
| 3 | Freezing | −50 | Atmospheric | 02:00 |
| 4 | Evacuation | −50 | 0.130 mbar | 00:10 |
| 5 | Primary drying | −50 → −20 | 0.130 mbar | 1:00 |
| 6 | Primary drying | −20 | 0.130 mbar | 19:00 |
| 7 | Primary drying | −20 → 5 | 0.130 mbar | 00:50 |
| 8 | Primary drying | 5 | 0.130 mbar | 05:00 |
| 7 | Primary drying | 5 → 25 | 0.130 mbar | 03:00 |
| 7 | Secondary drying | 25 | 0.130 mbar | 33:00 |
| 9 | Pre-Aeration with nitrogen | 15 | 0.8 bar | N.A. |
| 10 | Stoppering | 15 | 0.8 bar | N.A. |
| 11 | Aeration with nitrogen | 15 | Atmospheric | N.A. |
| | Total length (without stoppering) | | | 66:00 |

TABLE 15

RP-HPLC analysis main peak (purity) ALX-0081 formulation
[12.5 mg/mL API, 0.01% Tween-80 (v/v) and 7% sucrose (w/v)
in 20 mM citrate buffer at pH 6.5].

| Time point (months) | Storage condition | Avg. purity (% area main peak) |
|---|---|---|
| Initial | — | 93.3 |
| 1 | −20° C. | 93.0 |
| | +5° C. | 93.0 |
| | +25° C./60% RH | 93.0 |
| | +40° C./75% RH | 92.7 |
| 3 | −20° C. | 93.3 |
| | +5° C. | 93.3 |
| | +25° C./60% RH | 93.1 |
| | +40° C./75% RH | 92.6 |
| 6 | −20° C. | 93.2 |
| | +5° C. | 93.3 |
| | +25° C./60% RH | 93.0 |
| | +40° C./75% RH | 92.4 |
| 9 | −20° C. | 93.4 |
| | +5° C. | 93.3 |
| | +25° C./60% RH | 93.1 |
| | +40° C./75% RH | 91.8 |
| 12 | −20° C. | 93.2 |
| | +5° C. | 93.1 |
| | +25° C./60% RH | 92.8 |
| | +40° C./75% RH | 91.3 |

TABLE 16

RPC pre en post peak analysis of ALX-0081 formulation [12.5 mg/mL API, 0.01% Tween-80
(v/v) and 7% sucrose (w/v) in 20 mM citrate buffer at pH 6.5].

| Time point (months) | Storage Condition | Replicate | Pre-peaks (% area) | | | | Post-peaks (% area) | | | | |
| | | | 3 | 2 | 1 | Avg. 1 + 2 + 3 | Avg. 1 | Avg. 2 | Avg. 3 | Avg. 4 | Avg. 3 + 4 |
|---|---|---|---|---|---|---|---|---|---|---|---|
| Initial | — | 01 | 0.07 | 0.47 | 1.86 | 2.34 | 3.54 | 0.70 | 0.09 | 0.19 | 0.19 |
| | | 02 | 0.08 | 0.47 | 1.88 | | | | | | |
| 1 | −20° C. | 01 | 0.09 | 0.58 | 1.78 | 2.37 | 3.67 | 0.85 | 0.11 | 0.21 | 0.11 |
| | | 02 | 0.09 | 0.60 | 1.77 | | | | | | |
| | +5° C. | 01 | 0.09 | 0.60 | 1.79 | 2.39 | 3.64 | 0.84 | 0.11 | 0.22 | 0.11 |
| | | 02 | 0.09 | 0.59 | 1.80 | | | | | | |
| | +25° C./60% RH | 01 | 0.09 | 0.60 | 1.77 | 2.40 | 3.66 | 0.91 | 0.11 | 0.22 | 0.11 |
| | | 02 | 0.08 | 0.60 | 1.83 | | | | | | |
| | +40° C./75% RH | 01 | 0.09 | 0.56 | 1.88 | 2.45 | 3.68 | 1.11 | 0.11 | 0.23 | 0.11 |
| | | 02 | 0.09 | 0.63 | 1.83 | | | | | | |
| 3 | −20° C. | 01 | 0.09 | 0.51 | 1.91 | 2.37 | 3.45 | 0.72 | 0.09 | 0.26 | 0.26 |
| | | 02 | 0.09 | 0.49 | 1.82 | | | | | | |
| | +5° C. | 01 | 0.09 | 0.51 | 1.83 | 2.35 | 3.41 | 0.73 | 0.09 | 0.28 | 0.28 |
| | | 02 | 0.09 | 0.50 | 1.85 | | | | | | |
| | +25° C./60% RH | 01 | 0.09 | 0.49 | 1.86 | 2.38 | 3.47 | 0.84 | 0.09 | 0.27 | 0.27 |
| | | 02 | 0.09 | 0.53 | 1.87 | | | | | | |
| | +40° C./75% RH | 01 | 0.09 | 0.53 | 1.89 | 2.41 | 3.44 | 1.32 | 0.09 | 0.31 | 0.31 |
| | | 02 | 0.09 | 0.51 | 1.88 | | | | | | |

TABLE 16-continued

RPC pre en post peak analysis of ALX-0081 formulation [12.5 mg/mL API, 0.01% Tween-80 (v/v) and 7% sucrose (w/v) in 20 mM citrate buffer at pH 6.5].

| Time point (months) | Storage Condition | Replicate | Pre-peaks (% area) | | | | Post-peaks (% area) | | | | |
| | | | 3 | 2 | 1 | Avg. 1 + 2 + 3 | Avg. 1 | Avg. 2 | Avg. 3 | Avg. 4 | Avg. 3 + 4 |
|---|---|---|---|---|---|---|---|---|---|---|---|
| 6 | −20° C. | 01 | 0.07 | 0.52 | 1.85 | 2.40 | 3.49 | 0.71 | 0.08 | 0.21 | 0.21 |
| | | 02 | 0.07 | 0.54 | 1.89 | | | | | | |
| | +5° C. | 01 | 0.06 | 0.53 | 1.79 | 2.33 | 3.47 | 0.72 | 0.09 | 0.22 | 0.22 |
| | | 02 | 0.07 | 0.54 | 1.80 | | | | | | |
| | +25° C./60% RH | 01 | 0.07 | 0.54 | 1.82 | 2.40 | 3.50 | 0.93 | 0.09 | 0.22 | 0.22 |
| | | 02 | 0.06 | 0.53 | 1.91 | | | | | | |
| | +40° C./75% RH | 01 | 0.07 | 0.54 | 1.84 | 2.43 | 3.47 | 1.62 | 0.11 | 0.21 | 0.32 |
| | | 02 | 0.07 | 0.55 | 1.92 | | | | | | |
| 9 | −20° C. | 01 | 0.07 | 0.47 | 1.83 | 2.30 | 3.43 | 0.70 | 0.09 | 0.22 | 0.22 |
| | | 02 | 0.07 | 0.47 | 1.83 | | | | | | |
| | +5° C. | 01 | 0.07 | 0.45 | 1.87 | 2.31 | 3.45 | 0.69 | 0.09 | 0.22 | 0.22 |
| | | 02 | 0.07 | 0.47 | 1.83 | | | | | | |
| | +25° C./60% RH | 01 | 0.08 | 0.50 | 1.89 | 2.44 | 3.42 | 0.73 | 0.11 | 0.21 | 0.32 |
| | | 02 | 0.07 | 0.51 | 1.97 | | | | | | |
| | +40° C./75% RH | 01 | 0.07 | 0.49 | 1.84 | 2.32 | 3.46 | 2.07 | 0.13 | 0.24 | 0.37 |
| | | 02 | 0.08 | 0.47 | 1.84 | | | | | | |
| 12 | −20° C. | 01 | 0.07 | 0.50 | 1.66 | 216 | 3.64 | 0.70 | 0.10 | 0.25 | 0.35 |
| | | 02 | 0.07 | 0.49 | 1.66 | | | | | | |
| | +5° C. | 01 | 0.08 | 0.47 | 1.69 | 2.19 | 3.64 | 0.74 | 0.11 | 0.25 | 0.36 |
| | | 02 | 0.06 | 0.49 | 1.72 | | | | | | |
| | +25° C./60% RH | 01 | 0.08 | 0.48 | 1.74 | 2.21 | 3.55 | 1.07 | 0.12 | 0.26 | 0.38 |
| | | 02 | 0.09 | 0.47 | 1.73 | | | | | | |
| | +40° C./75% RH | 01 | 0.09 | 0.46 | 1.78 | 2.26 | 3.63 | 2.37 | 0.16 | 0.29 | 0.44 |
| | | 02 | 0.09 | 0.48 | 1.79 | | | | | | |

TABLE 17

Protein concentration results by UV for ALX-0081 formulation [12.5 mg/mL API, 0.01% Tween-80 (v/v) and 7% sucrose (w/v) in 20 mM citrate buffer at pH 6.5].

| Time point (months) | Storage Condition | Avg Conc of diluted sample (mg/mL) | Avg Conc Corrected by dilution factor (mg/vial) |
|---|---|---|---|
| Initial | — | 0.534 | 13.4 |
| 1 | −20° C. | 0.532 | 13.3 |
| | +5° C. | 0.530 | 13.3 |
| | +25° C./60% RH | 0.525 | 13.1 |
| | +40° C./75% RH | 0.516 | 12.9 |
| 3 | −20° C. | 0.501 | 12.5 |
| | +5° C. | 0.524 | 13.1 |
| | +25° C./60% RH | 0.530 | 13.3 |
| | +40° C./75% RH | 0.534 | 13.4 |
| 6 | −20° C. | 0.530 | 13.3 |
| | +5° C. | 0.528 | 13.2 |
| | +25° C./60% RH | 0.531 | 13.3 |
| | +40° C./75% RH | 0.523 | 13.1 |
| 9 | −20° C. | 0.505 | 12.6 |
| | +5° C. | 0.504 | 12.6 |
| | +25° C./60% RH | 0.511 | 12.8 |
| | +40° C./75% RH | 0.519 | 13.0 |
| 12 | −20° C. | 0.504 | 12.6 |
| | +5° C. | 0.505 | 12.6 |
| | +25° C./60% RH | 0.497 | 12.4 |
| | +40° C./75% RH | 0.510 | 12.7 |

TABLE 18

SE-HPLC analysis of ALX-0081 formulation [12.5 mg/mL API, 0.01% Tween-80 (v/v) and 7% sucrose (w/v) in 20 mM citrate buffer at pH 6.5].

| Time point (months) | Storage condition | Avg. Pre Peak (% Area) | Avg. Main Peak (% Area) |
|---|---|---|---|
| Initial | — | 0.55 | 99.5 |
| 1 | −20° C. | 0.51 | 99.5 |
| | +5° C. | 0.53 | 99.5 |
| | +25° C./60% RH | 0.55 | 99.4 |
| | +40° C./75% RH | 0.56 | 99.5 |
| 3 | −20° C. | 0.47 | 99.6 |
| | +5° C. | 0.47 | 99.5 |
| | +25° C./60% RH | 0.47 | 99.5 |
| | +40° C./75% RH | 0.48 | 99.5 |
| 6 | −20° C. | 0.60 | 99.4 |
| | +5° C. | 0.63 | 99.4 |
| | +25° C./60% RH | 0.65 | 99.4 |
| | +40° C./75% RH | 0.68 | 99.3 |
| 12 | −20° C. | 0.66 | 99.4 |
| | +5° C. | 0.68 | 99.3 |
| | +25° C./60% RH | 0.67 | 99.3 |
| | +40° C./75% RH | 0.71 | 99.3 |

TABLE 19

Results physical tests on lyophilized ALX-0081 stored at −20° C. [12.5 mg/mL API, 0.01%
Tween-80 (v/v) and 7% sucrose (w/v) in 20 mM citrate buffer at pH 6.5].

| Test | Unit | initial | 1M | 3M | 6M | 9M | 12M |
|---|---|---|---|---|---|---|---|
| Appearance of the lyophilisate | — | White cake with no dark particles | White cake with no dark particles | White cake with no dark particles | White cake with no dark particles | White cake with no dark particles | White cake with no dark particles |
| Appearance of the reconstituted solution | — | Clear colorless solution free of visible particles | Clear colorless solution free of visible particles | Clear colorless solution free of visible particles | Clear colorless solution free of visible particles | Clear colorless solution free of visible particles | Clear colorless solution free of visible particles |
| Reconstitution time (reconstitute with 1 mL of WFI) | seconds | 50 | 60 | 50 | 48 | 41 | 41 |
| Osmolality | mOsm/kg | 298 | 298 | 297 | 280 | — | 296 |
| pH of the reconstituted solution | — | 6.8 | 6.6 | 6.8 | 6.7 | — | 6.6 |
| Moisture content | % w/w | 0.65 | 0.72 | 0.83 | 0.74 | 0.62 | 0.63 |
| Subvisible particles by | particles/mL | 105 part/mL ø ≥ 10 μm; | 73 part/mL ø ≥ 10 μm; | 79 part/mL ø ≥ 10 μm; | 50 part/mL ø ≥ 10 μm; | — | — |
| HIAC | particles/mL | 3 part/mL ø ≥ 25 μm | 3 part/mL ø ≥ 25 μm | 7 part/mL ø ≥ 25 μm | 4 part/mL ø ≥ 25 μm | — | — |

TABLE 20

Results physical tests on lyophilized ALX-0081 stored at +5° C. [12.5 mg/mL API, 0.01%
Tween-80 (v/v) and 7% sucrose (w/v) in 20 mM citrate buffer at pH 6.5].

| Test | Unit | initial | 1M | 3M | 6M | 9M | 12M |
|---|---|---|---|---|---|---|---|
| Appearance of the lyophilisate | — | White cake with no dark particles | White cake with no dark particles | White cake with no dark particles | White cake with no dark particles | White cake with no dark particles | White cake with no dark particles |
| Appearance of the reconstituted solution | — | Clear colorless solution free of visible particles | Clear colorless solution free of visible particles | Clear colorless solution free of visible particles | Clear colorless solution free of visible particles | Clear colorless solution free of visible particles | Clear colorless solution free of visible particles |
| Reconstitution time (reconstitute with 1 mL of WFI) | seconds | 50 | 60 | 55 | 50 | 43 | 43 |
| Osmolality | mOsm/kg | 298 | 298 | 294 | 279 | — | 293 |
| pH of the reconstituted solution | — | 6.8 | 6.6 | 6.8 | 6.7 | — | 6.6 |
| Moisture content | % w/w | 0.65 | 0.76 | 0.72 | 0.72 | 0.80 | 0.68 |
| Subvisible particles by | particles/mL | 105 part/mL ø ≥ 10 μm; | 88 part/mL ø ≥ 10 μm; | 49 part/mL ø ≥ 10 μm; | 109 part/mL ø ≥ 10 μm; | — | — |
| HIAC | particles/mL | 3 part/mL ø ≥ 25 μm | 5 part/mL ø ≥ 25 μm | 4 part/mL ø ≥ 25 μm | 7 part/mL ø ≥ 25 μm | — | — |

TABLE 21

Results physical tests on lyophilized ALX-0081 stored at +25° C./60% RH [12.5 mg/mL API,
0.01% Tween-80 (v/v) and 7% sucrose (w/v) in 20 mM citrate buffer at pH 6.5].

| Test | Unit | initial | 1M | 3M | 6M | 9M | 12M |
|---|---|---|---|---|---|---|---|
| Appearance of the lyophilisate | — | White cake with no dark particles | White cake with no dark particles | White cake with no dark particles | White cake with no dark particles | White cake with no dark particles | White cake with no dark particles |
| Appearance of the reconstituted | — | Clear colorless solution free | Clear colorless solution free | Clear colorless solution free | Clear colorless solution free | Clear colorless solution free | Clear colorless solution free |

TABLE 21-continued

Results physical tests on lyophilized ALX-0081 stored at +25° C./60% RH [12.5 mg/mL API, 0.01% Tween-80 (v/v) and 7% sucrose (w/v) in 20 mM citrate buffer at pH 6.5].

| Test | Unit | initial | 1M | 3M | 6M | 9M | 12M |
|---|---|---|---|---|---|---|---|
| solution | | of visible particles | of visible particles | of visible particles | of visible particles | of visible particles | of visible particles |
| Reconstitution time (reconstitute with 1 mL of WFI) | seconds | 50 | 70 | 52 | 50 | 40 | 40 |
| Osmolality | mOsm/kg | 298 | 300 | 299 | 280 | — | 302 |
| pH of the reconstituted solution | — | 6.8 | 6.6 | 6.8 | 6.7 | — | 6.6 |
| Moisture content | % w/w | 0.65 | 0.83 | 0.68 | 0.93 | 0.99 | 0.89* |
| Subvisible particles by | particles/mL | 105 part/mL ⌀ ≥ 10 μm; | 58 part/mL ⌀ ≥ 10 μm; | 34 part/mL ⌀ ≥ 10 μm; | 45 part/mL ⌀ ≥ 10 μm; | — | — |
| HIAC | particles/mL | 3 part/mL ⌀ ≥ 25 μm | 3 part/mL ⌀ ≥ 25 μm | 4 part/mL ⌀ ≥ 25 μm | 0 part/mL ⌀ ≥ 25 μm | — | — |

Note:
*Average value of 2 instead of 3 independent measurements

TABLE 22

Results physical tests on lyophilized ALX-0081 stored at +40° C./75% RH [12.5 mg/mL API, 0.01% Tween-80 (v/v) and 7% sucrose (w/v) in 20 mM citrate buffer at pH 6.5].

| Test | Unit | initial | 1M | 3M | 6M | 9M | 12M |
|---|---|---|---|---|---|---|---|
| Appearance of the lyophilisate | — | White cake with no dark particles | White cake with no dark particles | White cake with no dark particles | White cake with no dark particles | White cake with no dark particles | White cake with no dark particles |
| Appearance of the reconstituted solution | — | Clear colorless solution free of visible particles | Clear colorless solution free of visible particles | Clear colorless solution free of visible particles | Clear colorless solution free of visible particles | Clear colorless solution free of visible particles | Clear colorless solution free of visible particles |
| Reconstitution time (reconstitute with 1 mL of WFI) | seconds | 50 | 70 | 50 | 52 | 44 | 43 |
| Osmolality | mOsm/kg | 298 | 300 | 299 | 279 | — | 292 |
| pH of the reconstituted solution | — | 6.8 | 6.7 | 6.8 | 6.7 | — | 6.6 |
| Moisture content | % w/w | 0.65 | 0.83 | 1.13 | 1.48 | 1.83 | 2.09* |
| Subvisible particles by | particles/mL | 105 part/mL ⌀ ≥ 10 μm; | 35 part/mL ⌀ ≥ 10 μm; | 94 part/mL ⌀ ≥ 10 μm; | 52 part/mL ⌀ ≥ 10 μm; | — | — |
| HIAC | particles/mL | 3 part/mL ⌀ ≥ 25 μm | 3 part/mL ⌀ ≥ 25 μm | 20 part/mL ⌀ ≥ 25 μm | 2 part/mL ⌀ ≥ 25 μm | — | — |

Note:
*Average value of 2 instead of 3 independent measurements

TABLE 23

Potency results ALX-0081 formulation [12.5 mg/mL API, 0.01% Tween-80 (v/v) and 7% sucrose (w/v) in 20 mM citrate buffer at pH 6.5].

| Time point (months) | Storage condition | Potency result (%)* | Lower limit (%)** | Upper limit (%)*⁻* | Pass/ Fail | Accept- ance criteria |
|---|---|---|---|---|---|---|
| Initial | — | 91.4 | 88.1 | 94.8 | Pass | 80%- |
| 1 | −20° C. | 94.8 | 91.5 | 98.2 | Pass | 120% |
| | +5° ± 3° C. | 94.5 | 90.3 | 98.8 | | (com- |
| | +25° C./60% RH | 97.4 | 94.2 | 100.7 | | pared |
| | +40° C./75% RH | 97.7 | 94.0 | 101.6 | | to |
| 3 | −20° C. | 105.5 | 101.7 | 109.5 | Pass | refer- |
| | +5° ± 3° C. | 99.3 | 95.3 | 103.4 | | ence) |
| | +25° C./60% RH | 97.0 | 93.1 | 101.1 | | |
| | +40° C./75% RH | 97.8 | 94.4 | 101.3 | | |

TABLE 23-continued

Potency results ALX-0081 formulation [12.5 mg/mL API, 0.01% Tween-80 (v/v) and 7% sucrose (w/v) in 20 mM citrate buffer at pH 6.5].

| Time point (months) | Storage condition | Potency result (%)* | Lower limit (%)** | Upper limit (%)*⁻* | Pass/ Fail | Accept- ance criteria |
|---|---|---|---|---|---|---|
| 6 | −20° C. | 93.2 | 90.2 | 96.2 | Pass | |
| | +5° ± 3° C. | 93.1 | 90.0 | 96.2 | | |
| | +25° C./60% RH | 97.5 | 94.1 | 101.0 | | |
| | +40° C./75% RH | 100.2 | 96.9 | 103.6 | | |
| 9 | −20° C. | 101.0 | 95.2 | 107.2 | Pass | |
| | +5° ± 3° C. | 101.1 | 94.8 | 107.7 | | |
| | +25° C./60% RH | 101.6 | 96.2 | 107.3 | | |
| | +40° C./75% RH | 98.7 | 93.8 | 103.9 | | |

TABLE 23-continued

Potency results ALX-0081 formulation [12.5 mg/mL API, 0.01%
Tween-80 (v/v) and 7% sucrose (w/v)
in 20 mM citrate buffer at pH 6.5].

| Time point (months) | Storage condition | Potency result (%)* | Lower limit (%)** | Upper limit (%)*⁻* | Pass/ Fail | Acceptance criteria |
|---|---|---|---|---|---|---|
| 12 | −20° C. | 101.3 | 98.7 | 103.9 | Pass | |
| | +5° ± 3° C. | 101.2 | 98.3 | 104.2 | | |
| | +25° C./60% RH | 105.7 | 103.0 | 108.5 | | |
| | +40° C./75% RH | 100.4 | 95.5 | 105.5 | | |

TABLE 24

In vitro comparability results of caplacizumab.

| Study type | Method | Criterion for comparability | Contemporaneous ALX-0081 | Lyophilized ALX-0081 |
|---|---|---|---|---|
| Biological activity (potency) | Surface plasmon resonance (Biacore) | Relative potency of 80-120% (compared to Master Reference Standard) | 102.8% | 102.9% |
| Biological activity (potency) | vWF neutralising ELISA | Relative potency of 80-120% (compared to Master Reference Standard) | 99.4% | 109.5% |
| Biological activity (biomarker) | RICO | Concentrations of both formulations needed to completely block RICO (<20%) do not differ by a factor > 5 | 0.4 µg/mL | 0.4 µg/mL |
| Affinity | Gyrolab | $K_D$ values of both formulations do not statistically differ (by means of 95% CI around $K_D$ estimation) | 6.84 pM (2.74-10.95) | 4.46 pM (−0.18-9.10) |

TABLE 25

Stability results on liquid ALX-0081 stored at ≤−60° C. [13.8 mg/mL API, 0.01% Tween-80
(v/v) and 7% sucrose (w/v) in 20 mM citrate buffer at pH 6.5].

| Test | Acceptance criteria | Initial | 9M | 12M | 18M | 24M |
|---|---|---|---|---|---|---|
| Content | 12.5 ± 2.5 mg/mL | 13.8 mg/mL | 13.4 mg/mL | 13.8 mg/mL | 13.4 mg/mL | 14.1 mg/mL |
| Purity cIEF | ≥90% main peak | 97% main peak | 98% main peak | 98% main peak | 98% main peak | 98% main peak |
| Purity RP-HPLC | ≥85% main peak | 91% main peak | 91.2% main peak | 91.4% main peak | 90.8% main peak | 91.2% main peak |
| | ≤10% pre-peaks 1 + 2 + 3 | 2% pre-peaks 1 + 2 + 3 | 2.1% pre-peaks 1 + 2 + 3 | 1.8% pre-peaks 1 + 2 + 3 | 2.4% pre-peaks 1 + 2 + 3 | 2.2% pre-peaks 1 + 2 + 3 |
| | ≤6% post-peak 1 | 6% post-peak 1 | (1.2% pre-peak 1) | (1.2% pre-peak 1) | (1.6% pre-peak 1) | (1.4% pre-peak 1) |
| | ≤4% post-peak 2 | 1% post-peak 2 | 5.4% post-peak 1 | 5.5% post-peak 1 | 5.3% post-peak 1 | 5.4% post-peak 1 |
| | | | 1.0% post-peak 2 | 1.0% post-peak 2 | 1.1% post-peak 2 | 1.1% post-peak 2 |
| Purity (monomer) SE-HPLC | ≥95% main peak | 99% main peak | 99.8% main peak | 99.7% main peak | 99.6% main peak | 99.6% main peak |
| pH | 6.5 ± 0.5 | 6.5 | 6.5 | 6.5 | 6.5 | 6.5 |
| Appearance | Clear, less opalescent than or equal to reference I, colorless | Clear, less opalescent or than or equal to reference I, colorless | Clear, as opalescent as reference I, colorless | Clear, less opalescent than reference I, colorless | Clear, less opalescent than reference I, colorless | Clear, less opalescent than or equal to reference I, colorless |

TABLE 25-continued

Stability results on liquid ALX-0081 stored at ≤−60° C. [13.8 mg/mL API, 0.01% Tween-80
(v/v) and 7% sucrose (w/v) in 20 mM citrate buffer at pH 6.5].

| Test | Acceptance criteria | Initial | 9M | 12M | 18M | 24M |
|---|---|---|---|---|---|---|
| Potency (Biacore) [CI: 95%] | $80 \times 10^3$- $120 \times 10^3$ U/mg | $93 \times 10^3$ U/mg | $96 \times 10^3$ U/mg [$91 \times 10^3$- $101 \times 10^3$ U/mg] | $100 \times 10^3$ U/mg [$97 \times 10^3$- $104 \times 10^3$ U/mg] | $99 \times 10^3$ U/mg [$97 \times 10^3$- $101 \times 10^3$ U/mg] | $94 \times 10^3$ U/mg [$93 \times 10^3$- $95 \times 10^3$ U/mg] |

TABLE 26

Stability results on liquid ALX-0081 stored at +5° C. ± 3° C. [13.8 mg/mL API, 0.01% Tween-80
(v/v) and 7% sucrose (w/v) in 20 mM citrate buffer at pH 6.5].

| Test | Acceptance criteria | Initial | 9M | 12M | 18M | 24M |
|---|---|---|---|---|---|---|
| Content | 12.5 ± 2.5 mg/mL | 13.8 mg/mL | 13.5 mg/mL | 13.9 mg/mL | 13.6 mg/mL | 13.1 mg/mL |
| Purity cIEF | ≥90% main peak | 97% main peak | 98% main peak | 98% main peak | 98% main peak | 97% main peak |
| Purity RP-HPLC | ≥85% main peak ≤10% pre-peaks 1 + 2 + 3 ≤6% post-peak 1 ≤4% post-peak 2 | 91% main peak 2% pre-peaks 1 + 2 + 3 6% post-peak 1 1% post-peak 2 | 90.5% main peak 2.6% pre-peaks 1 + 2 + 3 (1.7% pre-peak 1) 5.3% post-peak 1 1.4% post-peak 2 | 90.7% main peak 2.5% pre-peaks 1 + 2 + 3 (1.8% pre-peak 1) 5.4% post-peak 1 1.3% post-peak 2 | 90.2% main peak 2.9% pre-peaks 1 + 2 + 3 (2.1% pre-peak 1) 5.2% post-peak 1 1.5% post-peak 2 | 90.2% main peak 2.8% pre-peaks 1 + 2 + 3 (2.1% pre-peak 1) 5.2% post-peak 1 1.5% post-peak 2 |
| Purity (monomer) SE-HPLC | ≥95% main peak | 99% main peak | 99.8% main peak | 99.8% main peak | 99.6% main peak | 99.7% main peak |
| pH | 6.5 ± 0.5 | 6.5 | 6.5 | 6.5 | 6.5 | 6.5 |
| Appearance | Clear, less opalescent than or equal to reference I, colorless | Clear, less opalescent than or equal to reference I, colorless | Clear, as opalescent as reference I, colorless | Clear, less opalescent than reference I, colorless | Clear, less opalescent than reference I, colorless | Clear, less opalescent than or equal to reference I, colorless |
| Potency (BIAcore) [CI: 95%] | $80 \times 10^3$- $120 \times 10^3$ U/mg | $93 \times 10^3$ U/mg] | $100 \times 10^3$ U/mg [$95 \times 10^3$- $105 \times 10^3$ U/mg] | $96 \times 10^3$ U/mg [$93 \times 10^3$- $100 \times 10^3$ U/mg | $100 \times 10^3$ U/mg [$97 \times 10^3$- $103 \times 10^3$ U/mg] | $100 \times 10^3$ U/mg [$98 \times 10^3$- $102 \times 10^3$ U/mg] |

TABLE 27

Stability results on lyophilized ALX-0081 stored at +5° C. ± 3° C. [12.7 mg/mL API, 0.01%
Tween-80 (v/v) and 7% sucrose (w/v) in 20 mM citrate buffer at pH 6.5].

| Test | Acceptance criteria | Initial | 9M | 12M | 18M | 24M |
|---|---|---|---|---|---|---|
| Appearance lyophilisate | White cake essentially free of foreign matter | White cake with no dark particles | White cake essentially free of foreign matter | White cake essentially free of foreign matter | White cake essentially free of foreign matter | White cake essentially free of foreign matter |
| Appearance reconstituted solution | Clear, less opalescent than or equal to reference I, colorless and free of visible particles | Clear, less opalescent than or equal to reference I, colorless and free of visible particles | Clear, as opalescent as reference I, colorless and free of visible particles | Clear, less opalescent than reference I, colorless and free of visible particles | Clear, less opalescent than reference I, colorless and free of visible particles | Clear, less opalescent than or equal to reference I, colorless and free of visible particles |

TABLE 27-continued

Stability results on lyophilized ALX-0081 stored at +5° C. ± 3° C. [12.7 mg/mL API, 0.01% Tween-80 (v/v) and 7% sucrose (w/v) in 20 mM citrate buffer at pH 6.5].

| Test | Acceptance criteria | Initial | 9M | 12M | 18M | 24M |
|---|---|---|---|---|---|---|
| Content | 12.5 ± 2.5 mg/vial | 12.7 mg/vial | 12.7 mg/vial | 12.6 mg/vial | 12.4 mg/vial | 12.7 mg/vial |
| Purity cIEF | ≥90% main peak | 96% main peak | 97% main peak | 98% main peak | 98% main peak | 97% main peak |
| Purity RP-HPLC | ≥85% main peak | 90.8% main peak | 91.0% main peak | 91.3% main peak | 91.0% main peak | 91.1% main peak |
|  | ≤10% pre peaks 1 + 2 + 3 | 2.3% pre peaks 1 + 2 + 3 | 2.2% pre-peaks 1 + 2 + 3 (1.4% pre-peak 1) | 2.1% pre-peaks 1 + 2 + 3 (1.4% pre-peak 1) | 2.3% pre-peaks 1 + 2 + 3 (1.5% pre-peak 1) | 2.3% pre-peaks 1 + 2 + 3 (1.5% pre-peak 1) |
|  | ≤6% post peak 1 | 5.5% post-peak 1 | 5.2% post-peak 1 | 5.3% post-peak 1 | 5.3% post-peak 1 | 5.2% post-peak 1 |
|  | ≤4% post peak 2 | 1.1% post-peak 2 | 1.2% post-peak 2 | 1.1% post-peak 2 | 1.2% post-peak 2 | 1.2% post-peak 2 |
| Purity (monomer) SE-HPLC | ≥95% main peak | 99.6% main peak | 99.8% main peak | 99.8% main peak | 99.6% main peak | 99.6% main peak |
| pH | 6.5 ± 0.5 | 6.6 | 6.5 | 6.5 | 6.5 | 6.5 |
| Residual moisture | | 0.9% | 0.69% | 0.74% | 0.76% | 0.85% |
| Sub-visible particles by PAMAS | Particles ≥10 μm: ≤6000/vial Particles ≥25 μm: ≤600/vial | 14 ≥ 10 μm 0 ≥ 25 μm | | 359 ≥ 10 μm 13 ≥ 25 μm | | 6 ≥ 10 μm 0 ≥ 25 μm |
| Potency (BIAcore) [CI: 95%] | $80 \times 10^3$- $120 \times 10^3$ U/mg | $96 \times 10^3$ U/mg | $100 \times 10^3$ U/mg] [$95 \times 10^3$- $105 \times 10^3$ U/mg] | $107 \times 10^3$ U/mg [$104 \times 10^3$- $110 \times 10^3$ U/mg] | $101 \times 10^3$ U/mg [$100 \times 10^3$- $103 \times 10^3$ U/mg] | $96 \times 10^3$ U/mg [$93 \times 10^3$- $99 \times 10^3$ U/mg] |

TABLE 28

Stability results on lyophilized ALX-0081 stored at +25° C. (±2° C./60 ± 5% RH) [12.7 mg/mL API, 0.01% Tween-80 (v/v) and 7% sucrose (w/v) in 20 mM citrate buffer at pH 6.5].

| Test | Acceptance criteria | Initial | 9M | 12M | 18M |
|---|---|---|---|---|---|
| Appearance lyophilisate | White cake essentially free of foreign matter | White cake with no dark particles | White cake essentially free of foreign matter | White cake essentially free of foreign matter | White cake essentially free of foreign matter | White cake essentially free of foreign matter |
| Appearance reconstituted solution | Clear, less opalescent than or equal to reference I, colorless and free of visible particles | Clear, less opalescent than or equal to reference I, colorless and free of visible particles | Clear, as opalescent as reference I, colorless and free of visible particles | Clear, less opalescent than reference I, colorless and free of visible particles | Clear, less opalescent than reference I, colorless and free of visible particles | Clear, less opalescent than or equal to reference I, colorless and free of visible particles |
| Content | 12.5 ± 2.5 mg/vial | 12.7 mg/vial | 12.6 mg/vial | 12.6 mg/vial | 12.3 mg/vial | 13.1 mg/vial |
| Purity cIEF | ≥90% main peak | 96% main peak | 97% main peak | 98% main peak | 97% main peak | 97% main peak |
| Purity RP-HPLC | ≥85% main peak | 90.8% main peak | 90.7% main peak | 90.8% main peak | 90.5% main peak | 90.4% main peak |
|  | ≤10% pre peaks 1 + 2 + 3 | 2.3% pre peaks 1 + 2 + 3 | 2.3% pre-peaks 1 + 2 + 3 (1.5% pre-peak 1) | 2.1% pre-peaks 1 + 2 + 3 (1.4% pre-peak 1) | 2.4% pre-peaks 1 + 2 + 3 (1.6% pre-peak 1) | 2.4% pre-peaks 1 + 2 + 3 (1.6% pre-peak 1) |
|  | ≤6% post peak 1 | 5.5% post-peak 1 | 5.2% post-peak 1 | 5.2% post-peak 1 | 5.2% post-peak 1 | 5.2% post-peak 1 |
|  | ≤4% post peak 2 | 1.1% post-peak 2 | 1.5% post-peak 2 | 1.6% post-peak 2 | 1.8% post-peak 2 | 1.7% post-peak 2 |

TABLE 28-continued

Stability results on lyophilized ALX-0081 stored at +25° C. (±2° C./60 ± 5% RH) [12.7 mg/mL API, 0.01% Tween-80 (v/v) and 7% sucrose (w/v) in 20 mM citrate buffer at pH 6.5].

| Test | Acceptance criteria | Initial | 9M | 12M | 18M | |
|------|--------|---------|-----|-----|-----|---|
| Purity (monomer) SE-HPLC | ≥95% main peak | 99.6% main peak | 99.8% main peak | 99.8% main peak | 99.7% main peak | 99.7% main peak |
| pH | 6.5 ± 0.5 | 6.6 | 6.5 | 6.5 | 6.5 | 6.5 |
| Residual moisture | | 0.9% | 0.86% | 1.04% | 1.03% | 1.30% |
| Sub-visible particles by PAMAS | Particles ≥10 μm: ≤6000/vial Particles ≥25 μm: ≤600/vial | 14 ≥ 10 μm 0 ≤ 25 μm | | 389 ≥ 10 μm 12 ≥ 25 μm | | 13 ≥ 10 μm 1 ≥ 25 μm |
| Potency (BIAcore) [CI: 95%] | $80 \times 10^3$- $120 \times 10^3$ U/mg | $96 \times 10^3$ U/mg | $100 \times 10^3$ U/mg [$95 \times 10^3$- $106 \times 10^3$ U/mg] | $102 \times 10^3$ U/mg [$99 \times 10^3$- $105 \times 10^3$ U/mg] | $103 \times 10^3$ U/mg [$101 \times 10^3$- $104 \times 10^3$ U/mg] | $90 \times 10^3$ U/mg [$87 \times 10^3$- $94 \times 10^3$ U/mg] |

TABLE 29

Stability results on lyophilized ALX-0081 stored at +40° C. (±2° C./75 ± 5% RH) [12.7 mg/mL API, 0.01% Tween-80 (v/v) and 7% sucrose (w/v) in 20 mM citrate buffer at pH 6.5].

| Test | Acceptance criteria | Initial | 9M | 12M | 18M | 24M |
|------|--------|---------|-----|-----|-----|-----|
| Appearance lyophilisate | White cake essentially free of foreign matter | White cake with no dark particles | White cake essentially free of foreign matter | White cake essentially free of foreign matter | White cake essentially free of foreign matter | White cake essentially free of foreign matter |
| Appearance reconstituted solution | Clear, less opalescent than or equal to reference I, colorless and free of visible particles | Clear, as opalescent than or equal to reference I, colorless and free of visible particles | Clear, as opalescent as reference I, colorless and free of visible particles | Clear, less opalescent than reference I, colorless and free of visible particles | Clear, less opalescent than reference I, colorless and free of visible particles | Clear, less opalescent than or equal to reference I, colorless and free of visible particles |
| Content | 12.5 ± 2.5 mg/vial | 12.7 mg/vial | 12.5 mg/vial | 13.1 mg/vial | 12.1 mg/vial | 13.0 mg/vial |
| Purity cIEF | ≥90% main peak | 96% main peak | 94% main peak | 96% main peak | 93% main peak | 93% main peak |
| Purity RP-HPLC | ≥85% main peak ≤10% pre peaks 1 + 2 + 3 ≤6% post peak 1 ≤4% post peak 2 | 90.8% main peak 2.3% pre peaks 1 + 2 + 3 5.5% post-peak 1 1.1% post-peak 2 | 89.2% main peak 2.3% pre-peaks 1 + 2 + 3 (1.4% pre-peak 1) 5.2% post-peak 1 2.8% post-peak 2 | 89.1% main peak 2.2% pre-peaks 1 + 2 + 3 (1.4% pre-peak 1) 5.2% post-peak 1 3.2% post-peak 2 | 87.8% main peak 2.4% pre-peaks 1 + 2 + 3 (1.6% pre-peak 1) 5.2% post-peak 1 4.2% post-peak 2 | 85.5% main peak 2.4% pre-peaks 1 + 2 + 3 (1.7% pre-peak 1) 5.3% post-peak 1 6.2% post-peak 2 |
| Purity (monomer) SE-HPLC | ≥95% main peak | 99.6% main peak | 99.8% main peak | 99.8% main peak | 99.6% main peak | 99.7% main peak |
| pH | 6.5 ± 0.5 | 6.6 | 6.5 | 6.5 | 6.5 | 6.5 |
| Residual moisture | | 0.9% | 1.59% | 2.09% | 2.56% | 3.34% |
| Sub-visible particles by PAMAS | Particles ≥10 μm: ≤6000/vial Particles ≥25 μm: ≤600/vial | 14 ≥ 10 μm 0 ≥ 25 μm | | 873 ≥ 10 μm 18 ≥ 25 μm | | 4 ≥ 10 μm 0 ≥ 25 μm |

TABLE 29-continued

Stability results on lyophilized ALX-0081 stored at +40° C. (±2° C./75 ± 5% RH) [12.7 mg/mL API, 0.01% Tween-80 (v/v) and 7% sucrose (w/v) in 20 mM citrate buffer at pH 6.5].

| Test | Acceptance criteria | Initial | 9M | 12M | 18M | 24M |
|---|---|---|---|---|---|---|
| Potency (BIAcore) [CI: 95%] | $80 \times 10^3$- $120 \times 10^3$ U/mg | $96 \times 10^3$ U/mg | $100 \times 10^3$ U/mg] [$96 \times 10^3$- $104 \times 10^3$ U/mg] | $97 \times 10^3$ U/mg [$94 \times 10^3$- $101 \times 10^3$ U/mg] | $108 \times 10^3$ U/mg [$106 \times 10^3$- $111 \times 10^3$ U/mg] | $93 \times 10^3$ U/mg [$91 \times 10^3$ - $95 \times 10^3$ U/mg |

Equivalents

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. A formulation comprising a von Willebrand Factor (vWF) binder, a citrate buffer, an excipient, and polysorbate 80, wherein:

(a) the vWF binder has a concentration from about 0.1 mg/mL to about 80 mg/mL;

(b) the excipient is sucrose at a concentration of about 5% to about 15% (w/v), wherein the sucrose is not at a concentration of about 7% (w/v);

(c) the polysorbate 80 has a concentration of about 0.001% to 0.5% (v/v); and (d) the citrate buffer has a concentration of about 5 mM to about 200 mM such that the pH of the formulation is about 6.0 to about 7.0, wherein said vWF binder comprises at least one of SEQ ID NOs: 1-19.

2. The formulation according to claim 1, which has:

(i) less than 5% of high molecular weight (HMW) species after storage for at least 12 months at 5° C.; and/or (ii) less than 5% of low molecular weight (LMW) species after storage for at least 12 months at 5° C.

3. The formulation according to claim 1, which is a liquid or reconstituted lyophilized formulation.

4. The formulation according to claim 1, which is in a lyophilized, spray-dried, or frozen form.

5. The formulation according to claim 1, wherein said vWF binder comprises an amino acid sequence which is at least 90% identical to SEQ ID NO: 1.

6. The formulation according to claim 1, wherein the vWF binder in the formulation retains at least 80% of its stability after storage for at least 12 months at 5° C.

7. The formulation according to claim 1, wherein at least 90% of the vWF binder retains its binding activity after storage compared to the binding activity prior to storage, said binding activity as measured by ELISA and/or surface plasmon resonance.

8. The formulation according to claim 1, wherein at least 95% of the vWF binder retains its binding activity after storage compared to the binding activity prior to storage, said binding activity as measured by ELISA and/or surface plasmon resonance.

9. The formulation according to claim 1, wherein at least 99% of the vWF binder retains its binding activity after storage compared to the binding activity prior to storage, said binding activity as measured by ELISA and/or surface plasmon resonance.

10. The formulation according to claim 1, wherein said vWF binder comprises an amino acid sequence which is identical to SEQ ID NO: 1.

11. An article of manufacture comprising a container comprising the formulation according to claim 1, which is a bulk storage formulation, wherein the container is suitable for storing at least 100 liters of the formulation at below freezing conditions.

12. A kit or an article of manufacture, comprising a container containing the formulation of claim 1, and instructions for use.

13. The kit or article of manufacture of claim 12, wherein the formulation is present in a vial or an injectable syringe.

14. A formulation comprising a von Willebrand Factor (vWF) binder, a citrate buffer, an excipient, and polysorbate 80, wherein:
  (a) the vWF binder has a concentration from about 0.1 mg/mL to about 80 mg/mL;
  (b) the excipient is sucrose at a concentration of about 5% to about 15% (w/v);
  (c) the polysorbate 80 has a concentration of about 0.001% to 0.5% (v/v), wherein the polysorbate 80 does not have a concentration of about 0.01% (w/v); and
  (d) the citrate buffer has a concentration of about 5 mM to about 200 mM such that the pH of the formulation is about 6.0 to about 7.0,
  wherein said vWF binder comprises at least one of SEQ ID NOs: 1-19.

15. The formulation of claim 14, wherein said vWF binder comprises the amino acid sequence of SEQ ID NO: 1.

16. The formulation according to claim 14, which is a liquid or reconstituted lyophilized formulation.

17. A formulation comprising a von Willebrand Factor (vWF) binder, a citrate buffer, an excipient, and polysorbate 80, wherein:
  (a) the vWF binder has a concentration from about 0.1 mg/mL to about 80 mg/mL;
  (b) the excipient is sucrose at a concentration of about 5% to about 15% (w/v);
  (c) the polysorbate 80 has a concentration of about 0.001% to 0.5% (v/v); and
  (d) the citrate buffer has a concentration of about 5 mM to about 200 mM such that the pH of the formulation is about 6.0 to about 7.0, wherein the citrate buffer does not have a concentration of about 20 mM,
  wherein said vWF binder comprises at least one of SEQ ID NOs: 1-19.

18. The formulation of claim 17, wherein said vWF binder comprises the amino acid sequence of SEQ ID NO: 1.

19. The formulation according to claim 17, which is a liquid or reconstituted lyophilized formulation.

* * * * *